(12) United States Patent
Raz et al.

(10) Patent No.: US 7,560,436 B2
(45) Date of Patent: Jul. 14, 2009

(54) METHODS OF TREATING GASTROINTESTINAL INFLAMMATION

(75) Inventors: Eyal Raz, Del Mar, CA (US); Kyoko Katakura, San Diego, CA (US); Jongdae Lee, San Diego, CA (US); Daniel Rachmilewitz, Tel Aviv (IL)

(73) Assignee: The Regents of the University of California, Oakland, CA (US)

( * ) Notice: Subject to any disclaimer, the term of this patent is extended or adjusted under 35 U.S.C. 154(b) by 116 days.

(21) Appl. No.: 11/359,945

(22) Filed: Feb. 21, 2006

(65) Prior Publication Data

US 2007/0004654 A1 Jan. 4, 2007

Related U.S. Application Data

(60) Provisional application No. 60/655,455, filed on Feb. 22, 2005.

(51) Int. Cl.
*A01N 43/04* (2006.01)
*A61K 31/70* (2006.01)

(52) U.S. Cl. .............................. 514/43; 514/2; 514/42; 514/44

(58) Field of Classification Search .................. None
See application file for complete search history.

(56) References Cited

U.S. PATENT DOCUMENTS

| | | | |
|---|---|---|---|
| 6,399,773 B1 * | 6/2002 | Liu et al. | 544/106 |
| 6,613,751 B2 | 9/2003 | Raz et al. | |
| 6,930,093 B2 * | 8/2005 | Brantl | 514/43 |
| 7,176,213 B2 * | 2/2007 | Aranyi et al. | 514/292 |
| 2003/0139364 A1 | 7/2003 | Krieg | |
| 2004/0009949 A1 | 1/2004 | Krieg | |
| 2004/0162309 A1 | 8/2004 | Gorden et al. | |
| 2004/0171086 A1 | 9/2004 | Fink et al. | |
| 2005/0004144 A1 | 1/2005 | Carson et al. | |
| 2005/0009766 A1 | 1/2005 | Brantl | |

FOREIGN PATENT DOCUMENTS

| | | |
|---|---|---|
| WO | WO0162207 | 8/2001 |
| WO | WO2005007672 | 1/2005 |
| WO | WO2005067959 | 7/2005 |
| WO | WO2005076824 | 8/2005 |

OTHER PUBLICATIONS

Shanahan The Lancet (2002), vol. 359, pp. 62-69.*
Vollmer et al. (2004) *Antimicrobial. Agents and Chemotherapy* 48:2314-2317.
Blumberg et al. (1999) *Curr Opin Immunol* 6:648-56.
Papadakis et al. (2000) *Annu Rev Med* 51:289-98.
Blumberg (2001) *JAMA* 285(5):643-647.
Nagura et al. (2001) *Digestion* 63 Suppl S1:12-21.
Bhan et al. (1999) *Immunol Rev* 169:195-207.
Neurath et al. (200) *Int Rev Immunol* 19:51-6.
Dieleman et al. (1998) *Clin Exp Immunol* 114:385-91.
MacDonald (1997) *Eur J Gastroenterol Hepatol* (1997).
Podolsky (1999) *Am J Physiol* 277:G495-9.
Hyams (2000) Curr Opin Pediatr 12(5):451-5.
Pohl et al. (2000) *Hepatogastroenterology* 47(31):57-70.
Barton and Mezhitov (2002) *Curr. Top. Microbiol. Immunol.* 270:81-92.
Rakoff-Nahoum et al. (2004) *Cell* 118:229-241.
Uematsu S., et al. "Therapeutic targeting of toll-like receptors." Drug Discovery Today: Therapeutic Strategies, Elsevier, 2004, vol. 1, No. 3, pp. 299-304.
Rachmilewitz D., et al. "Immunostimulatory DNA ameliorates experimental and sprontaneous murine colitis." Gastroenterology, Elsevier, 2002, vol. 122, No. 5, pp. 1428-1441.
Rachmilewitz D., et al. "Toll-like receptor 9 signaling mediates the anti-inflammatory effects of probiotics in murine experimental colitis." Gastroenterology, Elsevier, 2004, vol. 126, No. 2, pp. 520-528.
Netea et al. "NOD2 mediates anti-flammatory signals induced by TRL2 ligands: implications for crohn's disease." Eur. J. Immunol., 2004, vol. 34, pp. 2052-2059.
Jurk et al. "Human TLR7 and TLR8 independently confer responsiveness to the antiviral compound R-848." Nature immonology, 2002, vol. 3, No. 6, p. 499.
Cario et al. "Differential alteration in intestinal epithelial cell expression of toll-like receptor 3 (TLR3) and TLR4 in inflammatory bowel disease." Infection and Immunity, 2000, vol. 68, No. 12, pp. 7010-7017.
Karlsson, et al. "Intra-colonic administration of the TLR7 agonist R-848 induces an acute local and systemic inflammation in mice." Biochem. Biophys. Res. Comm., 2008, vol. 367, pp. 242-248.

* cited by examiner

*Primary Examiner*—Patrick T Lewis
(74) *Attorney, Agent, or Firm*—Paula A. Borden; Bozicevic, Field & Francis LLP

(57) ABSTRACT

The present invention provides methods of treating gastrointestinal inflammation, methods of treating inflammatory bowel disease, methods of treating Crohn's Disease, and methods of treating ulcerative colitis in an individual. The methods generally involve administering an effective amount of an agent that increases the level of a Type I interferon and/or that activates a Type I interferon signaling pathway in the individual.

24 Claims, 4 Drawing Sheets

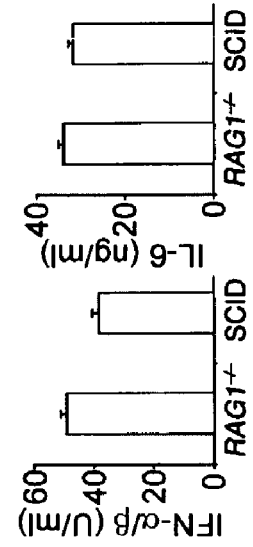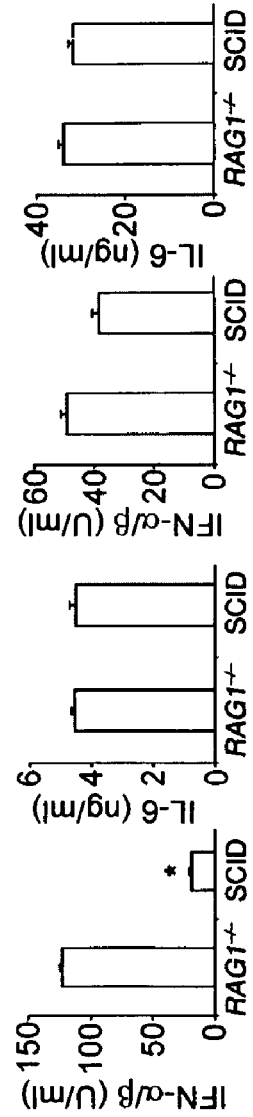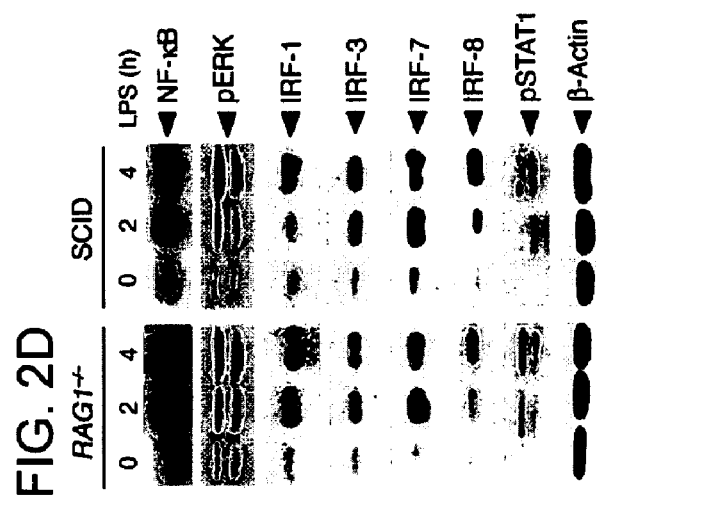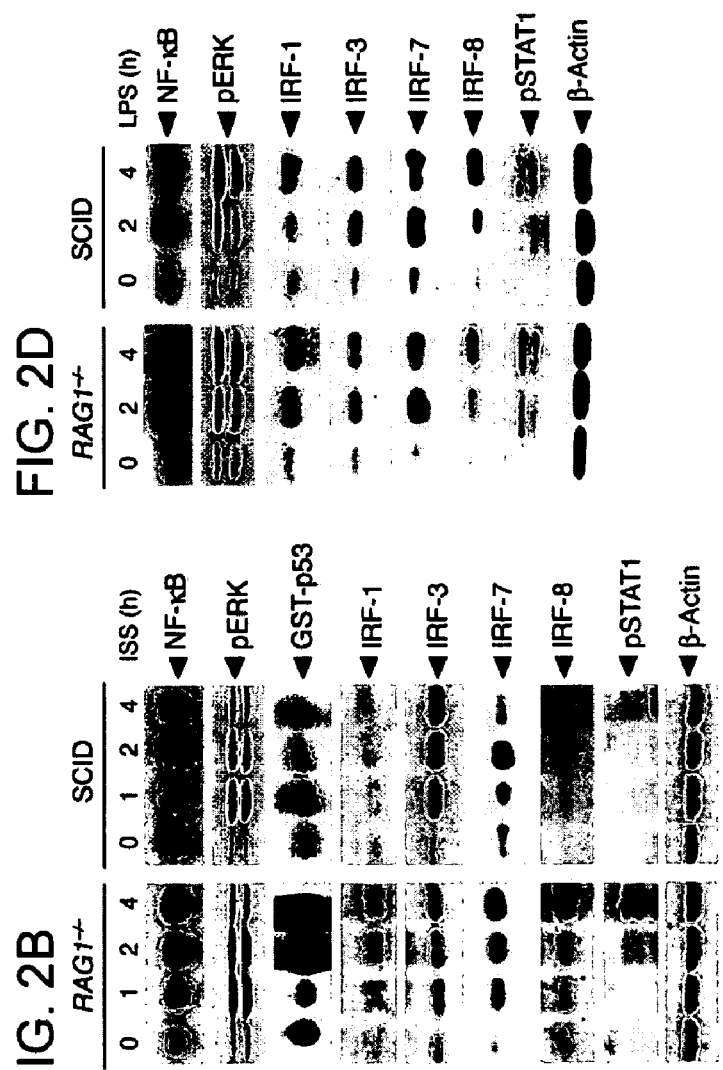

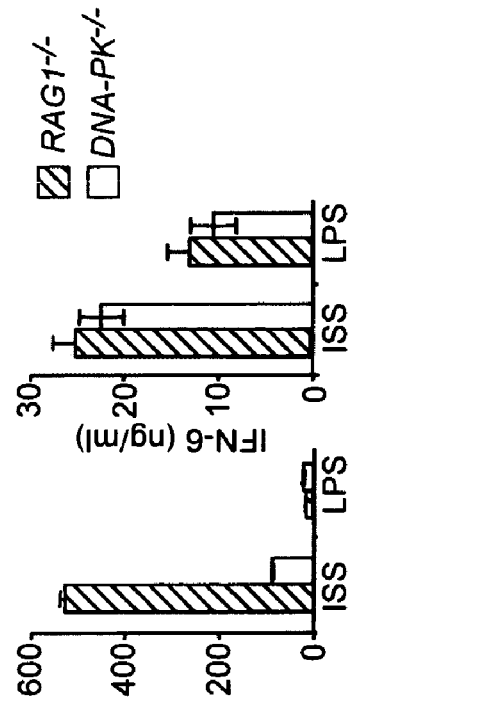
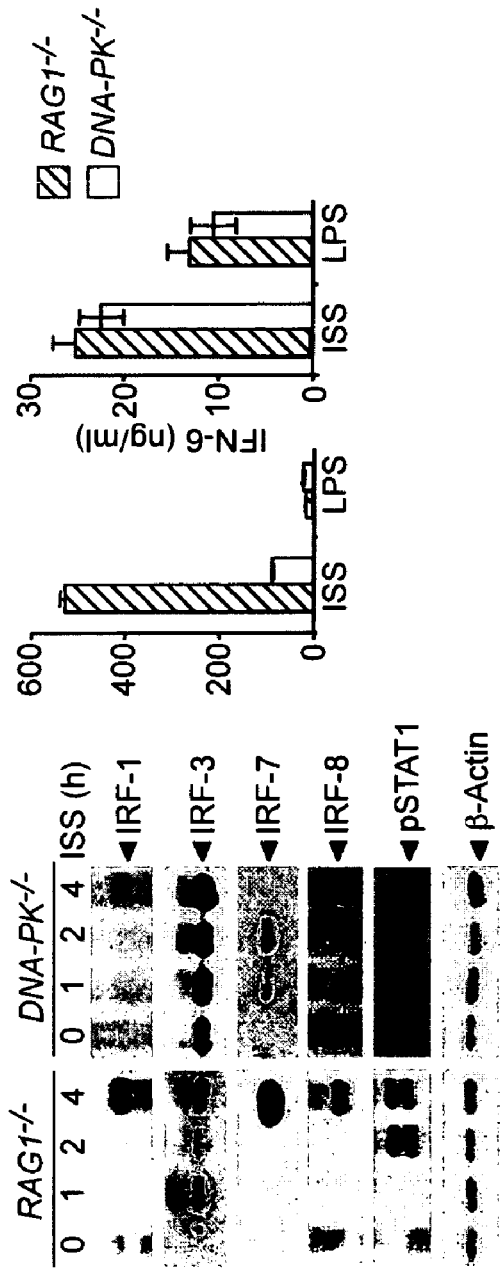
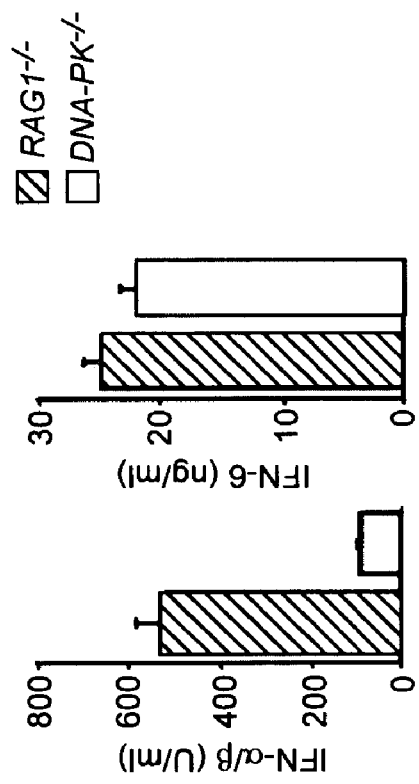
FIG. 3A
FIG. 3B
FIG. 3C

METHODS OF TREATING GASTROINTESTINAL INFLAMMATION

CROSS-REFERENCE

This application claims the benefit of U.S. Provisional Patent Application No. 60/655,455, filed Feb. 22, 2005, which application is incorporated herein by reference in its entirety.

STATEMENT REGARDING FEDERALLY SPONSORED RESEARCH

The U.S. government has certain rights in this invention, pursuant to grant nos. AI40682 and DK35108 awarded by the National Institutes of Health.

FIELD OF THE INVENTION

The present invention is in the field of treating gastrointestinal inflammatory disorders.

BACKGROUND OF THE INVENTION

Gastrointestinal inflammation is one of the most common types of inflammatory process which affects humans. Inflammatory bowel disease (IBD), a form of chronic gastrointestinal inflammation, includes a group of chronic inflammatory disorders of generally unknown etiology, e.g., ulcerative colitis (UC) and Crohn's disease (CD). Clinical and experimental evidence suggest that the pathogenesis of IBD is multifactorial involving susceptibility genes and environmental factors. The interaction of these factors with the immune system leads to intestinal inflammation and dysregulated mucosal immunity against commensal bacteria, various microbial products (e.g., LPS) or antigens (Mayer et al. Current concept of IBD: Etiology and pathogenesis. In "Inflammatory Bowel Disease" $5^{th}$ edition 2000, Kirsner J B editor. W. B. Sanunders Company, pp 280-296).

Animal models of colitis have highlighted the prominent role of $CD4^+$ T cells in the regulation of intestinal inflammation. Cytokine imbalance and the production of inflammatory mediators have been postulated to play an important role in the pathogenesis of both experimental colitis and IBD. Animal models of colitis include the dinitrobenzene sulphonic acid-induced colitis (DNB) model (Neurath et al. (2000) *Int Rev Immunol* 19:51-6), which mimics CD; and the dextran sodium sulphate (DSS) model, where DSS induces acute and chronic colitis (Dieleman et al. (1998) *Clin Exp Immunol* 114:385-91). Studies using transgenic mice having deletions in a cytokine gene develop a spontaneous inflammatory bowel disease (for a review see, e.g., MacDonald (1997) *Eur J Gastroenterol Hepatol* 9(11):1051-50). The inflammatory process and the immune response at mucosal sites result in mucosal barrier dysfumction leading to further exposure to enteric bacteria and/or their products that perpetuate mucosal inflammation.

Immunosuppressive and anti-inflammatory agents in high maintenance doses are the principal drugs used in the therapy of chronic inflammatory gastrointestinal disorders. Anti-inflammatory drugs presently used in treatment of IBD include aminosalycilates and immunosuppressive agents such as corticosteroids, azathioprine, cyclosporine and methotrexate. Corticosteroids remain the mainstay of anti-inflammatory and immunosuppressive therapy for many gastrointestinal conditions. Specific anti-TNF antibodies have also been used for treatment of IBD. About 20-25% of the patients with UC fail to respond to intensive and optimal medical therapy and therefore are referred to surgery for total proctocolectomy. In general, patients with CD are less responsive to medical therapy and usually do not respond to surgical treatment. Anti-TNFα antibodies have also been introduced to treat patients with CD with some efficacy, but this approach is ineffective in patients with UC. Thus, IBD is a medical problem that lacks an effective treatment.

Management of gastrointestinal inflammation, particular chronic gastrointestinal inflammation, is important, since the presence of gastrointestinal inflammation can be an early sign for risk of development of further serious conditions. For example, colorectal cancer represents the major cause for excess morbidity and mortality by malignant disease in ulcerative colitis as well as in Crohn's disease. The risk for ulcerative colitis associated colorectal cancer is increased at least 2-fold compared to the normal population. Colorectal cancer is observed in 5.5-13.5% of all patients with ulcerative colitis and 0.4-0.8% of patients with Crohn's disease. Ulcerative colitis associated colorectal cancer typically can occur in the entire colon, is often multifocal and of undifferentiated histology. Stage distribution and prognosis of ulcerative colitis associated colorectal cancer appears to be similar to that of sporadic colorectal cancer with an overall survival of about 40% (15-65%) after 5 years with tumor stage at diagnosis being the most important predictive parameter for survival (for a review see, e.g., Pohl et al. (2000) *Hepatogastroenterology* 47(31):57-70). Restorative proctocolectomy with a pouch made in the distal ileum is a common surgical procedure used in the treatment of ulcerative colitis; however, such can result in pouchitis. Pouchitis is an inflammation of the pouch created as treatment of a patient with ulcerative colitis (see, e.g., Sandbom et al. (1999) *Inflammatory Bowel Diseases* 5:33-39). Gastrointestinal symptoms of pouchitis include incontinence, bleeding, fever, and urgency.

There is a need in the art for effective methods of treating gastrointestinal inflammation, particularly chronic gastrointestinal inflammation such as IBD. The present invention addresses this need.

Literature

U.S. Pat. No. 6,613,751; U.S. Patent Publication Nos. 2005/0009766, 2004/0171086, 2004/0162309, 2004/0009949, and 2003/0139364; Vollmer et al. (2004) *Antimicrobial. Agents and Chemotherapy* 48:2314-2317; Blumberg et al. (1999) *Curr Opin Immunol* 6:648-56; Papadakis et al. (2000) *Annu Rev Med* 51:289-98; Blumberg (2001) *JAMA* 285(5):643-647; Nagura et al. (2001) *Digestion* 63 Suppl S1:12-21; Bhan et al. (1999) *Immunol Rev* 169:195-207; Neurath et al. (200) *Int Rev Immunol* 19:51-6; Dieleman et al. (1998) *Clin Exp Immunol* 114:385-91; MacDonald (1997) *Eur J Gastroenterol Hepatol (1997)*; Podolsky (1999) *Am J Physiol* 277:G495-9; Hyams (2000) Curr Opin Pediatr 12(5): 451-5; Pohl et al. (2000) *Hepatogastroenterology* 47(31):57-70; Barton and Mezhitov (2002) *Curr. Top. Microbiol. Immunol.* 270:81-92; Rakoff-Nahoum et al. (2004) Cell 118:229-241.

SUMMARY OF THE INVENTION

The present invention provides methods of treating gastrointestinal inflammation, methods of treating inflammatory bowel disease, methods of treating Crohn's disease, and methods of treating ulcerative colitis in an individual. The methods generally involve administering an effective amount of an agent that increases the level of a Type I interferon and/or that activates a Type I interferon signaling pathway in the individual.

BRIEF DESCRIPTION OF THE DRAWINGS

FIGS. 2A-D depict data showing that DNA-PK mediates TLR9-induced type I IFN production via IRF-1 and IRF-8.

FIGS. 3A-C depict data showing that TLR9-activated DNA-PK mediates activation of IRFs and type-I IFN.

DEFINITIONS

Figure 1B:
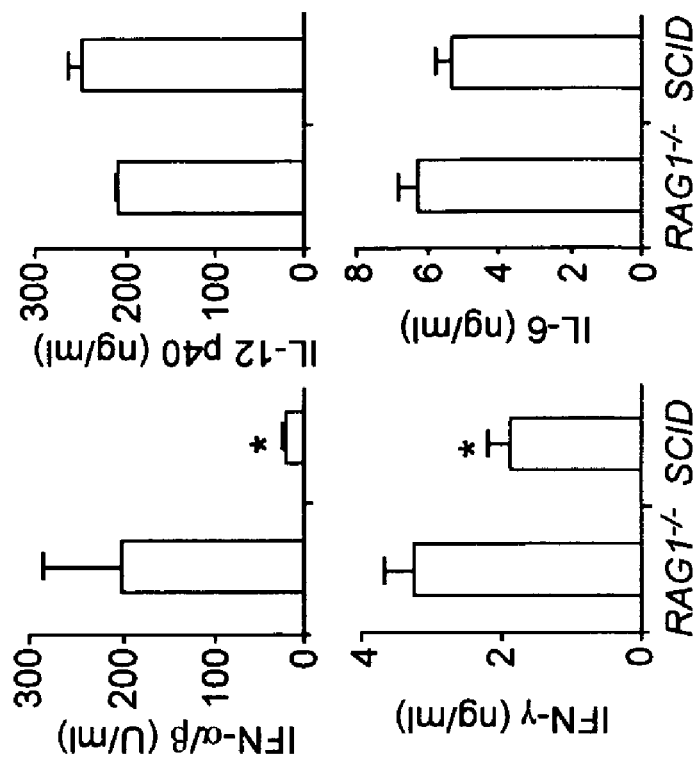
FIGS. 1A and 1B depict cytokine production after CpG-ODN stimulation.

"Gastrointestinal inflammation" as used herein refers to inflammation of a mucosal layer of the gastrointestinal tract, and encompasses acute and chronic inflammatory conditions. Acute inflammation is generally characterized by a short time of onset and infiltration or influx of neutrophils. Chronic inflammation is generally characterized by a relatively longer period of onset and infiltration or influx of mononuclear cells. Chronic inflammation can also typically characterized by periods of spontaneous remission and spontaneous occurrence. "Mucosal layer of the gastrointestinal tract" is meant to include mucosa of the bowel (including the small intestine and large intestine), rectum, stomach (gastric) lining, oral cavity, and the like.

"Chronic gastrointestinal inflammation" refers to inflammation of the mucosal of the gastrointestinal tract that is characterized by a relatively longer period of onset, is long-lasting (e.g., from several days, weeks, months, or years and up to the life of the subject), and is associated with infiltration or influx of mononuclear cells and can be further associated with periods of spontaneous remission and spontaneous occurrence. Thus, subjects with chronic gastrointestinal inflammation may be expected to require a long period of supervision, observation, or care. "Chronic gastrointestinal inflammatory conditions" (also referred to as "chronic gastrointestinal inflammatory diseases") having such chronic inflammation include, but are not necessarily limited to, inflammatory bowel disease (IBD), colitis induced by environmental insults (e.g., gastrointestinal inflammation (e.g., colitis) caused by or associated with (e.g., as a side effect) a therapeutic regimen, such as administration of chemotherapy, radiation therapy, and the like), colitis in conditions such as chronic granulomatous disease (Schappi et al. Arch Dis Child. 2001 Feb; 84(2):147-151), celiac disease, celiac sprue (a heritable disease in which the intestinal lining is inflamed in response to the ingestion of a protein known as gluten), food allergies, gastritis, infectious gastritis or enterocolitis (e.g., Helicobacter pylori-infected chronic active gastritis) and other forms of gastrointestinal inflammation caused by an infectious agent, and other like conditions.

As used herein, "inflammatory bowel disease" or "IBD" refers to any of a variety of diseases characterized by inflammation of all or part of the intestines. Examples of inflammatory bowel disease include, but are not limited to, Crohn's disease and ulcerative colitis. Reference to IBD throughout the specification is often referred to in the specification as exemplary of gastrointestinal inflammatory conditions, and is not meant to be limiting. The term IBD includes pseudomembranous colitis, hemorrhagic colitis, hemolytic-uremic syndrome colitis, collagenous colitis, ischemic colitis, radiation colitis, drug and chemically induced colitis, diversion colitis, ulcerative colitis, irritable bowel syndrome, irritable colon syndrome and Crohn's disease; and within Crohn's disease all the subtypes including active, refractory, and fistulizing and Crohn's disease As used herein, "subject" or "individual" or "patient" refers to any subject for whom or which therapy is desired, and generally refers to the recipient of the therapy to be practiced according to the invention. The subject can be any vertebrate, but will typically be a mammal. If a mammal, the subject will in many embodiments be a human, but may also be a domestic livestock, laboratory subject or pet animal.

"Treatment" or "treating" as used herein means any therapeutic intervention in a subject, usually a mammalian subject, generally a human subject, including: (i) prevention, that is, causing the clinical symptoms not to develop, e.g., preventing progression to a harmful state; (ii) inhibition, that is, arresting the development or further development of clinical symptoms, e.g., mitigating or completely inhibiting active (ongoing) inflammation so as to decrease inflammation, which decrease can include substantially complete elimination of inflammation; and/or (iii) relief, that is, causing the regression of clinical symptoms, e.g., causing relief from diarrhea, rectal bleeding and weight loss, reduction in colon weight, reduction in colon lesions, reduction of strictures, reduction of fistulae, and/or reduction colonic inflammation.

The term "agonist," as used herein, refers to a compound that can combine with a receptor (e.g., a TLR) to produce a cellular activity. An agonist may be a ligand that directly binds to the receptor. Alternatively, an agonist may combine with a receptor indirectly by, for example, (a) forming a complex with another molecule that directly binds to the receptor, or (b) otherwise results in the modification of another compound so that the other compound directly binds to the receptor. An agonist may be referred to as an agonist of a particular TLR (e.g., a TLR7 agonist) or a particular combination of TLRs (e.g., a TLR 7/8 agonist—an agonist of both TLR7 and TLR8).

The term "selective" and variations thereof refer to having a differential or a non-general impact on biological activity. An agonist that selectively modulates biological activity through a particular TLR may be a TLR-selective agonist. TLR-selectivity may be described with respect to a particular TLR (e.g., TLR8-selective) or with respect to a particular combination of TLRs (e.g., TLR 7/8-selective).

The term "prodrug," as used herein, refers to a derivative of a drug molecule that requires a chemical or enzymatic biotransformation in order to release the active parent drug in the body.

The terms "CpG-ODN," "CpG nucleic acid," "CpG polynucleotide," and "CpG oligonucleotide," used interchangeably herein, refer to a polynucleotide that comprises at least one 5'-CG-3' moiety, and in many embodiments comprises an unmethylated 5'-CG-3' moiety. In general, a CpG nucleic acid is a single-or double-stranded DNA or RNA polynucleotide having at least six nucleotide bases that may comprise, or consist of, a modified nucleotide or a sequence of modified nucleosides. In some embodiments, the 5'-CG-3' moiety of the CpG nucleic acid is part of a palindromic nucleotide sequence. In some embodiments, the 5'-CG-3' moiety of the CpG nucleic acid is part of a non-palindromic nucleotide sequence.

The terms "oligonucleotide," "polynucleotide," "nucleotide sequence," and "nucleic acid molecule", used interchangeably herein, refer to polymeric forms of nucleotides of any length, either ribonucleotides or deoxyribonucleotides. Thus, this term includes, but is not limited to, single-, double-, or multi-stranded DNA or RNA, genomic bacterial DNA, plasmid DNA, cDNA, DNA-RNA hybrids, or a polymer comprising purine and pyrimidine bases or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidites, and/or phosphorothioates, and thus can be an oligodeoxynucleoside phosphoramidate or a mixed phosphoramidate-phosphodiester oligomer. Peyrottes et al. (1996) *Nucl. Acids Res.* 24:1841-1848; Chaturvedi et al. (1996) *Nucl. Acids Res.* 24:2318-2323. The polynucleotide may comprise one or more L-nucleosides. A polynucleotide may comprise modified nucleotides, such as methylated nucleotides and nucleotide analogs, uracyl, other sugars, and linking groups such as fluororibose and thioate, and nucleotide branches. The sequence of nucleotides may be interrupted by non-nucleotide components. A polynucleotide may be modified to comprise N3'-P5' (NP) phosphoramidate, morpholino phosphorociamidate (MF), locked nucleic acid (LNA), 2'-O-methoxyethyl (MOE), or 2'-fluoro, arabinonucleic acid (FANA), which can enhance the resistance of the polynucleotide to nuclease degradation (see, e.g., Faria et al. (2001) *Nature Biotechnol.* 19:40-44; Toulme (2001) *Nature Biotechnol.* 19:17-18). A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support. CpG nucleic acids can be provided in various formulations, e.g., in association with liposomes, microencapsulated, etc., as described in more detail herein.

As used herein the term "isolated" is meant to describe a compound of interest that is in an environment different from that in which the compound naturally occurs. "Isolated" is meant to include compounds that are within samples that are substantially enriched for the compound of interest and/or in which the compound of interest is partially or substantially purified.

As used herein, the term "substantially purified" refers to a compound that is removed from its natural environment and is at least 60% free, at least 75% free, at least 90% free, at least 95% free, at least 98% free, or more than 98% free from other components with which it is naturally associated.

The term "effective amount" or "therapeutically effective amount" means a dosage sufficient to provide for treatment for the disease state being treated or to otherwise provide the desired effect (e.g., reduction of inflammation). The precise dosage will vary according to a variety of factors such as subject-dependent variables (e.g., age, immune system health, etc.), the disease (e.g., the type of gastrointestinal inflammnation), and the treatment being effected. In the case of treatment of gastrointestinal inflammation, an "effective amount" is that amount sufficient to substantially improve the likelihood of treating the inflammation or other symptom of a gastrointestinal inflammatory disease such as IBD.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups which are limited to hydrocarbon groups are termed "homoalkyl."

The terms "alkoxy," "alkylamino," and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written.

The terms "cycloalkyl" and "heterocycloalkyl," by themselves or in combination with other terms, represent, unless otherwise stated, cyclic versions of "alkyl" and "heteroalkyl," respectively. Thus, a cycloalkyl or heterocycloalkyl include saturated and unsaturated ring linkages. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" meant to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings (e.g., from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl.

As used herein, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like.

Each of the above terms (e.g., "alkyl," "heteroalkyl," "aryl" and "heteroaryl") are meant to include both substituted and unsubstituted forms of the indicated radical. Suitable substituents include carboxy, protected carboxy, amino, protected amino, halo, hydroxy, protected hydroxy, nitro, cyano, monosubstituted amino, protected monosubstituted amino, disubstituted amino, $C_1$ to $C_7$ alkoxy, $C_1$ to $C_7$ acyl, $C_1$ to $C_7$ acyloxy, and the like.

As used herein, "pharmaceutically acceptable derivatives" of an active compound include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs.

A "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

As used herein, "pharmaceutically acceptable carrier" includes any material which, when combined with an active ingredient of a composition, allows the ingredient to retain biological activity and without causing disruptive reactions with the subject's immune system. Examples include, but are not limited to, any of the standard pharmaceutical carriers such as a phosphate buffered saline solution, water, emulsions such as oil/water emulsion, and various types of wetting agents. Exemplary diluents for aerosol or parenteral administration are phosphate buffered saline or normal (0.9%) saline. Compositions comprising such carriers are formulated by well known conventional methods (see, for example, Remington's Pharmaceutical Sciences, Chapter 43, 14th Ed., Mack Publishing Col, Easton Pa. 18042, USA). Pharmaceutically acceptable excipients have been amply described in a variety of publications, including, for example, A. Gennaro (2000) "Remington: The Science and Practice of Pharmacy," 20th edition, Lippincott, Williams, & Wilkins; Remington's Pharmaceutical Sciences, 14th Ed. or latest edition, Mack Publishing Col, Easton Pa. 18042, USA; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a Type I interferon-inducing agent" includes a plurality of such agents and reference to "the toll-like receptor agonist" includes reference to one or more toll-like receptor agonists and equivalents thereof known to those skilled in the art, and so forth. It is further noted that the claims may be drafted to exclude any optional element. As such, this statement is intended to serve as antecedent basis for use of such exclusive terminology as "solely,"

"only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention provides methods of treating gastrointestinal inflammation in an individual, the methods generally involving administering to an individual in need thereof an effective amount of an agent that induces synthesis of a Type I interferon and/or that increases a level of a Type I interferon and/or that activates a Type I interferon signaling pathway in the individual. An agent that induces synthesis of a Type I interferon and/or that increases a level of a Type I interferon in an individual and/or that activates a Type I interferon signaling pathway is referred to herein as a "Type I interferon activating agent."

Gastroinflammatory disorders that can be treated using a subject method include, but are not limited to, IBD; ulcerative colitis; Crohn's disease; colitis induced by environmental insults, (e.g., gastrointestinal inflammation (e.g., colitis) caused by or associated with (e.g., as a side effect) a. therapeutic regimen, such as administration of chemotherapy, radiation therapy, and the like); colitis in conditions such as chronic granulomatous disease; celiac disease; celiac sprue; colitis caused by food allergies, gastritis, infectious gastritis, and enterocolitis; and pouchitis.

A subject method is effective to treat a gastrointestinal inflammatory disorder. In some embodiments, an effective amount of a Type I interferon activating agent is an amount that, in monotherapy or in combination therapy, is effective to reduce the degree or severity of at least one symptom or feature of a gastrointestinal inflammatory disorder by at least about 10%, at least about 20%, at least about 30%, at least about 40%, at least about 50%, at least about 60%, at least about 70%, or at least about 80%, or more, compared to the degree or severity of the symptom or feature in the individual not treated with the agent. Symptoms and features of gastrointestinal inflammatory disorders include, but are not limited to, diarrhea; incontinence; rectal bleeding; fever; urgency; an increased volume of stool, e.g., associated with diarrhea; weight loss; abdominal pain; intestinal obstruction; colonic lesions; colonic strictures; perianal fistulae; colonic fistulae; etc.

Thus, e.g., in some embodiments, an effective amount of a Type I interferon activating agent is an amount that, in monotherapy or in combination therapy, is effective to reduce the incidence of diarrhea and/or the volume of stool by at least about 10%, at least about 20%, at least about 30%, at least about 40%, at least about 50%, at least about 60%, at least about 70%, or at least about 80%, or more, compared to the incidence or volume in the individual not treated with the agent. As another example, an effective amount of a Type I interferon activating agent is an amount that, in monotherapy or in combination therapy, is effective to reduce rectal bleeding by at least about 10%, at least about 20%, at least about 30%, at least about 40%, at least about 50%, at least about 60%, at least about 70%, or at least about 80%, or more, compared to the amount of rectal bleeding in the individual not treated with the agent.

The effectiveness of therapy can be monitored by monitoring the reduction of disease activity in the subject. Reduction in disease activity can be monitored by, for example, monitoring reduction of incidence of diarrhea or volume of stool, reduction of rectal bleeding, reduction of weight loss, reduction of size or number of colon lesions, reduction or opening of strictures, reduction or closure of fistulae, and the like. Therapeutic effectiveness can also be measured by for example, a decrease in anti-neutrophil cytoplasmic antibodies (ANCA) in a biological sample, a decrease in colonic myelo-peroxidase activity, reduction of anemia (as detected by, for example, erythrocyte sedimentation rate (ESR), hemoglobin levels, and the like), or other conventional indicator of gastrointestinal inflammation. Many of these methods for assessing therapeutic efficacy can be accomplished through endoscopy or through blood tests. Methods for monitoring gastrointestinal inflammation are well known in the art and well within the skill and knowledge of the ordinarily skilled artisan.

Reduction of Risk of Subsequent Disease

The methods of the invention can also provide for reduced risk of other conditions for which gastrointestinal inflammation is a risk factor. For example, ulcerative colitis is a risk factor for colonic carcinoma. Thus, treatment of ulcerative colitis (e.g., by reduction of inflammation) according to the methods of the invention also reduces the risk of colonic cancer (e.g., colonic carcinoma, colonic adenoma, and the like). The methods of the invention can thus be applied as prophylactic measure to prevent or reduce the risk of onset of colonic carcinoma, particularly in those patients that are high risk of colon cancer.

Established risk factors for colon cancer in those patients having ulcerative colitis include long duration of the disease, large extent of the disease, low activity of the disease, young age at onset, presence of complicating primary sclerosing cholangitis or stenotic disease and possibly lack of adequate surveillance, inadequate pharmacological therapy, folate deficiency and non-smoking. Crohn's disease is associated with an increased risk of colorectal carcinoma in patients with long-standing disease, strictures and fistulae under the condition that the colon is involved, tumors of the small intestine may occur occasionally. (see, e.g., Pohl, et al. (2000), ibid). Thus treating using a method according to the invention can be of particular benefit in these patients.

Type I Interferon Activating Agents

Type I interferon activating agents that are suitable for use in a subject method include, but are not limited to, a toll-like receptor (TLR) agonist (e.g., a TLR2 agonist; a TLR3 agonist; a TLR4 agonist; a TLR7 agonist; a TLR8 agonist; a TLR9 agonist); a nucleoside analog; an inosine monophosphate dehydrogenase (IMPDH) inhibitor; a DNA methyltransferase inhibitor; a dendritic cell growth factor; a Type I interferon mimetic; and the like.

Nucleoside Analogs

Nucleoside analogs that are suitable for use in a subject treatment method include, but are not limited to, ribavirin, levovirin, viramidine, isatoribine, an L-ribofuranosyl nucleoside as disclosed in U.S. Pat. No. 5,559,101 and encompassed by Formula I of U.S. Pat. No. 5,559,101 (e.g., 1-β-L-ribofuranosyluracil, 1-β-L-ribofuranosyl-5-fluorouracil, 1-β-L-ribofuranosylcytosine, 9-β-L-ribofuranosyladenine, 9-β-L-ribofuranosylhypoxanthine, 9-β-L-ribofuranosylguanine, 9-β-L-ribofuranosyl-6-thioguanine, 2-amino-α-L-ribofuranl[1',2': 4,5]oxazoline, $O^2,O^2$-anhydro-1-α-L-ribofuranosyluracil, 1-α-L-ribofuranosyluracil, 1-(2,3,5-tri-O-benzoyl-α-ribofuranosyl)-4-thiouracil, 1-α-L-ribofuranosylcytosine, 1-α-L-ribofuranosyl-4-thiouracil, 1-α-L-ribofuranosyl-5-fluorouracil, 2-amino-β-L-arabinofurano[1',2':4,5]oxazoline, O²,O²-anhydro-β-L-arabinofuranosyluracil, 2'-deoxy-β-L-uridine, 3'5'-Di-O-benzoyl-2'deoxy-4-thio β-L-uridine, 2'-deoxy-β-L-cytidine, 2'-deoxy-β-L-4-thiouridine, 2'-deoxy-β-L-thymidine, 2'-deoxy-β-L-5-fluorouridine, 2',3'-dideoxy-β-L-uridine, 2'-deoxy-β-L-5-fluorouridine, and 2'-deoxy-β-L-inosine); a compound as disclosed in U.S. Pat. No. 6,423,695 and encompassed by Formula I of U.S. Pat. No. 6,423,695; a compound as disclosed in U.S. Patent Publication No. 2002/0058635, and encompassed by Formula 1 of U.S. Patent Publication No. 2002/0058635; a nucleoside analog as disclosed in WO 01/90121 A2 (Idenix); a nucleoside analog as disclosed in WO 02/069903 A2 (Biocryst Pharmaceuticals Inc.); a nucleoside analog as disclosed in WO 02/057287 A2 or WO 02/057425 A2 (both Merck/Isis); and the like.

Also suitable for use are ribofuranose compounds of the formula:

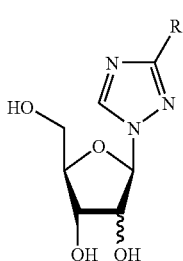

Formula I wherein R is a group selected from a carboxamide, an amidine, and pharmaceutically acceptable acid addition salts thereof and the configuration at the C₂ carbon of the ribofuranose moiety is D or L. Suitable for use in a subject method is ribavirin (1-β-D-ribofaranosyl-1H-1,2,4-triazole-3-carboxamide), which is the compound having Formula (I) where R is (C=O)NH₂), or a pharmaceutically acceptable acid addition salt thereof; Levovirin (1-β-L-ribofuranosyl-1H-1,2,4-triazole-3-carboxamide), which is the compound having Formula (I) where R is (C=O)NH₂), or a pharmaceutically acceptable acid addition salt thereof; 1-β-D-ribofuranosyl-1H-1,2,4-triazole-3-amidine, which is the compound having Formula (I) where R is (C=NH)NH₂), or a pharmaceutically acceptable acid addition salt thereof; and 1-β-L-ribofuranosyl-1H-1,2,4-triazole-3-amidine, which is the compound having Formula (I) where R is (C=NH)NH₂, or a pharmaceutically acceptable acid addition salt thereof.

In some embodiments, the nucleoside analog is ribavirin. Ribavirin, 1-β-D-ribofuranosyl-1H-1,2,4-triazole-3-carboxamide, available from ICN Pharmaceuticals, Inc., Costa Mesa, Calif., is described in the Merck Index, compound No. 8199, Eleventh Edition. Its manufacture and formulation is described in U.S. Pat. No. 4,211,771. The invention also contemplates use of derivatives of ribavirin (see, e.g., U.S. Pat. No. 6,277,830). The ribavirin may be administered orally in capsule or tablet form. Of course, other types of administration of ribavirin, as they become available are contemplated, such as by nasal spray, transdermally, by suppository, by sustained release dosage form, etc. Any form of administration will work so long as the proper dosages are delivered without destroying the active ingredient.

In some embodiments, the nucleoside analog is levovirin. Levovirin is the L-enantiomer of ribavirin. Levovirin(1-β-ribofuranosyl-1H-1,2,4-triazole-3-carboxamide) is manufactured by ICN Pharmaceuticals.

Levovirin has the following structure:

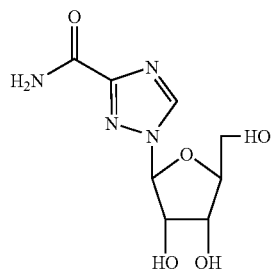

In some embodiments, the nucleoside analog viramidine. Viramidine is a 3-carboxamidine derivative of ribavirin, and acts as a prodrug of ribavirin. It is efficiently converted to ribavirin by adenosine deaminases.

Viramidine has the following structure:

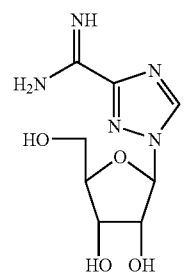

Also included for use in a subject treatment method are 2-substituted 8-hydroxyadenine, and prodrugs thereof. Suitable 2-substituted 8-hydroxyadenine compounds include, but are not limited to, 9-benzyl-8-hydroxy-2-(2-hydroxyethylthio)adenine (SM-295072; see, e.g., Kurimoto et al. (2004) Chem. Pharm. Bull. 52:466-469). Suitable 2-substituted 8-hydroxyadenine compounds include compounds of Formula II:

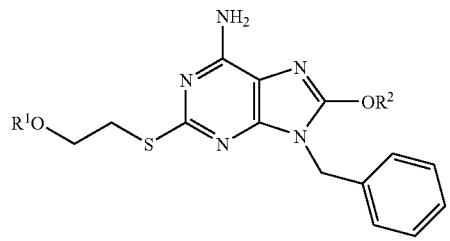

Formula II wherein R₁ is H, CO₂Et, or CO₂Bu; and R₂ is H, CO₂Et, CO₂Bu, CO₂Me, or CO₂Pr, where Et, Bu, Me, and Pr are ethyl, butyl, methyl, and propyl groups, respectively. Suitable 2-substituted 8-hydroxyadenine compounds include 9-benzyl-8-ethoxycarbonyloxy-2-[2-(ethyoxycarbonyloxy)ethylthio]adenine; 9-benzyl-8-butoxycarbonyloxy-2-[2-(butoxycarbonyloxy)ethylthio]adenine; 9-benzyl-8-hydroxy-2-[2-(butoxycarbonyloxy)ethylthio]adenine; 9-benzyl-8-butoxycarbonyloxy-2-(2-hydroxyethylthio)adenine; 9-benzyl-2-(2-hydroxyethylthio)-8-methoxycarbonyloxyadenine; 9-benzyl-8-ethoxycarbonyloxy-2-(2-hydroxyethylthio)adenine; 9-benzyl-2-(2-hydroxyethylthio)-8-isopropoxycarbonyloxyadenine; and 9-benzyl-2-(2-hydroxyethylthio)-8-isobutoxycarbonyloxyadenine.

Suitable 2-substituted 8-hydroxyadenine compounds include any of the compounds 1-8 listed in Table 1 of Kurimoto et al. (2004), supra.

IMPDH Inhibitors

IMPDH inhibitors that are suitable for use in a subject treatment method include, but are not limited to, VX-497 ((S)—N-3-[3-(3-methoxy-4-oxazol-5-yl-phenyl)-ureido]-benzyl-carbamic acid tetrahydrofuran-3-yl-ester); Vertex Pharmaceuticals; see, e.g., Markland et al. (2000) *Antimicrob. Agents Chemother.* 44:859-866); Tiazoflirin (2-β-D-ribofuranosylthiazole-4-carboxamide; see, e.g., U.S. Pat. Nos. 4,680,285 and 4,451,648); mycophenolate mofetil; morpholinoethyl ester of mycophenolic acid (US 2001/0046957); selenazofurin; benzamide riboside; ribavirin; levovirin (Ribapharm; see, e.g., Watson (2002) *Curr Opin Investig Drugs* 3(5):680-3); viramidine (Ribapharm); mizoribine (N'-[β-D-Ribofuranosyl]-5-hydroxyimidazole-4-carboxamide), an enantiomer of mizoribine, mizoribine base, mizoribine monophosphate, mizoribine aglycone, or a prodrug of such compound; and the like.

Inducers of Type I IFN Signaling Pathways

Agents that induce or activate Type I IFN signaling pathways include agents that induce or activate signal transducer and activator of transcription (STAT) 1, 2, and 3 genes and/or STAT1, 2, and 3 gene products. Such agents include, but are not limited to, 5-aza-2'-deoxydytidine (5-Aza-CdR; Karpf et al. (1999) *Proc. Natl. Acad. Sci. USA* 96:14007-14012); and the like.

Dendritic Cell Growth Factor

Suitable dendritic cell (DC) growth factors include compounds that increase the number of DC in an individual. DCs include myeloid DCs and plasmacytoid DCs.

Suitable DC growth factors include, but are not limited to, Flt3 ligands; GM-CSF; and IL-3, and active fragments thereof. DC growth factors include DC growth factors that are fusion polypeptides, e.g., a fusion protein comprising a DC growth factor (or active fragment thereof) fused in-frame to a second polypeptide (e.g., a "fusion partner"), which fusion partner is fused at the N-terminus or the C-terminus of the DC growth factor. Suitable fusion partners include antibody or antibody fragments (e.g., an Fc portion of an antibody); and the like.

A DC growth factor will in some embodiments be a variant polypeptide, e.g., a polypeptide that differs in amino acid sequence from a corresponding naturally-occurring DC growth factor. A variant DC growth factor will usually be substantially similar to the sequences provided herein, i.e. will differ by at least one amino acid, and may differ by at least two but generally not more than about ten amino acids. The sequence changes may be substitutions, insertions or deletions. Conservative amino acid substitutions typically include substitutions within the following groups: (glycine, alanine); (valine, isoleucine, leucine); (aspartic acid, glutamic acid); (asparagine, glutamine); (serine, threonine); (lysine, arginine); or (phenylalanine, tyrosine).

Modifications of interest that may or may not alter the primary amino acid sequence of a DC growth factor include chemical derivatization of polypeptides, e.g., acetylation, or carboxylation; changes in amino acid sequence that introduce or remove a glycosylation site; changes in amino acid sequence that make the protein susceptible to PEGylation; and the like. Also included are modifications of glycosylation, e.g. those made by modifying the glycosylation patterns of a polypeptide during its synthesis and processing or in further processing steps; e.g. by exposing the polypeptide to enzymes that affect glycosylation, such as mammalian glycosylating or deglycosylating enzymes. Also embraced are sequences that have phosphorylated amino acid residues, e.g. phosphotyrosine, phosphoserine, or phosphothreonine.

A DC growth factor will in some embodiments include one or more modifications designed to modify one or more properties such as half-life, solubility, resistance to proteolytic degradation, and the like, without substantially decreasing the biological activity of the DC growth factor. Such modifications include, but are not limited to, addition of one or more biocompatible polymers, such as polyethylene glycol (PEG) moieties (e.g., "PEGylation", where the modified DC growth factor is referred to as a "PEGylated" DC growth factor); glycosylation; phosphorylation; and acetylation.

Suitable IL-3 polypeptides include IL-3 polypeptides having amino acid sequences which are substantially similar to the native human Interleukin-3 amino acid sequences and which are biologically active in that they are capable of binding to IL-3 receptors or transducing a biological signal initiated by binding to IL-3 receptors, or cross-reacting with anti-IL-3 antibodies raised against IL-3. Such sequences are disclosed, for example, in EP Publ. Nos. 275,598 and 282, 185. The term "IL-3" also includes analogs of IL-3 molecules which exhibit at least some biological activity in common with native IL-3. Exemplary analogs of IL-3 are also disclosed in U.S. Pat. No. 5,128,450. Suitable IL-3 includes polymer-modified IL-3, e.g., PEGylated IL-3.

Suitable GM-CSF includes native (e.g., naturally-occurring) GM-CSF; recombinant GM-CSF, e.g., recombinant human GM-CSF (rhu GM-CSF; e.g., Leukine™ rhuGM-CSF; sargramostin); PEGylated GM-CSF (see, e.g., U.S. Pat. No. 6,384,195); and the like. Leukine™ is a biosynthetic, yeast-derived, recombinant human GM-CSF, consisting of a single 127 amino acid glycoprotein that differs from endogenous (native, naturally-occurring) human GM-CSF by having a leucine instead of a proline at position 23. Other natural and synthetic GM-CSFs, and derivatives thereof having the biological activity of natural human GM-CSF, will be equally useful in the practice of the invention.

TLR Agonists

A TLR agonist is any compound or substance that functions to activate a TLR, e.g., to induce a signaling event mediated by a TLR signal transduction pathway. Suitable TLR agonists include TLR2 agonists, TLR3 agonists, TLR4 agonists, TLR7 agonists, TLR8 agonists, and TLR9 agonists.

Suitable TLR agonists include isolated, naturally-occurring TLR agonists; and synthetic TLR agonists. TLR agonists isolated from a naturally-occurring source of TLR agonist are generally purified, e.g., the purified TLR agonist is at least about 80% pure, at least about 90% pure, at least about 95% pure, at least about 98% pure, at least about 99% pure, or more than 99% pure. Synthetic TLR agonists are prepared by standard means, and are generally at least about 80% pure, at least about 90% pure, at least about 95% pure, at least about 98% pure, at least about 99% pure, or more than 99% pure.

Suitable TLR agonists include TLR agonists that are not attached to any other compound. Suitable TLR agonists include TLR agonists that are attached, covalently or non-covalently, to a second compound. In some embodiments, a TLR agonist is attached to another compound directly. In other embodiments, a TLR agonist is attached to another compound through a linker. The compound to which a TLR agonist is attached includes a carrier, a scaffold, an insoluble support, a microparticle, a microsphere, and the like. Carriers include therapeutic polypeptides; polypeptides that provide for increased solubility; polypeptides that increase the half-life of the TLR agonist in a physiological medium (e.g., serum or other bodily fluid); and the like. In some embodiments, a TLR agonist will be conjugated, directly or via a linker, to a therapeutic polypeptide. Therapeutic polypeptides that are suitable for attachment to a TLR agonist include, but are not limited to, a dendritic cell growth factor (e.g., GM-CSF); a cytokine; an interferon (e.g., an IFN-α, an IFN-β, etc.); a TNF antagonist; and the like.

In some embodiments, the TLR agonist is a selective TLR agonist. In some embodiments, a TLR-selective compound mediates cellular activity (e.g., induces production of IFN-α and/or IFN-β) through one or more TLRs. In such cases, "TLR selective" may refer to selectivity between two or more TLRs of particular interest, e.g., TLR7 and TLR8. Thus, e.g., "TLR8-selective" may refer, in some embodiments, to a compound that modulates TLR8-mediated cellular activity, but does not modulate (i.e., does not substantially increase or decrease) cellular activity mediated through any other TLR (i.e., TLR8 only). In other embodiments, however, "TLR8-selective" may refer to a compound that modulates TLR8-mediated cellular activity and cellular activity modulated through one or more other TLRs, but does not modulate cellular activity mediated through one or more particular TLRs, for example, TLR7 (i.e., TLR8, but not TLR7.

Similarly, "TLR7-selective" may refer to a compound that modulates TLR7-mediated cellular activity, but does not modulate cellular activity through any other TLR (TLR7 only). Alternatively, "TLR7-selective" may refer to a compound that modulates TLR7-mediated cellular activity and cellular activity mediated by at least one other TLR, but does not modulate cellular activity mediated through one or more particular TLR, for example, TLR8 (TLR7, but not TLR8).

As noted above, TLR-selective compound may mediate cellular activity through a particular combination of TLRs, but does not modulate activity through another TLR. For example, a compound may mediate cellular activity through both TLR7 and TLR9, but not mediate cellular activity through TLR8. Depending upon the specific nature of the desired selectivity, such as compound may be referred to as, for example, TLR7-selective (if, e.g., TLR9-mediated cellular activity is not relevant), TLR9-selective (if, e.g., TLR7-mediated cellular activity is not relevant), or TLR7/9-selective (if, e.g., both TLR7-mediated cellular activity and TLR9-mediated cellular activity are relevant).

Whether a given TLR agonist is selective is readily determined using methods known in the art. For example, U.S. Patent Publication No. 2004/0171086 provides a method for determining whether a given compound is a selective TLR agonist.

In some embodiments, the TLR agonist is a prodrug version of a TLR agonist. Prodrugs are composed of a prodrug portion covalently linked to an active therapeutic agent. Prodrugs are capable of being converted to drugs (active therapeutic agents) in vivo by certain chemical or enzymatic modifications of their structure. Examples of prodrug portions are well-known in the art and can be found in the following references: Biological Approaches to the Controlled Delivery of Drugs, R. L. Juliano, New York Academy of Sciences, (1988); Hydrolysis in Drug and Prodrug Metabolism: Chemistry, Biochemistry, and Enzymology, Bernard Testa, Vch Verlagsgesellschaft Mbh, (2003); and Prodrugs: Topical and Ocular Drug Delivery, Kenneth Sloan, Marcel Dekker; (1992). Examples of prodrug portions are peptides, e.g., peptides that direct the TLR ligand to the site of action, and a peptide which possesses two or more free and uncoupled carboxylic acids at its amino terminus. Other exemplary cleaveable prodrug portions include ester groups, ether groups, acyl groups, alkyl groups, phosphate groups, sulfonate groups, N-oxides, and tert-butoxy carbonyl groups.

In some embodiments, the TLR agonist is a monomeric TLR agonist. In other embodiments, the TLR agonist is multimerized, e.g., the TLR agonist is polymeric. In some embodiments, a multimerized TLR agonist is homofunctional, e.g., is composed of one type of TLR agonist. In other embodiments, the multimerized TLR agonist is a heterofunctional TLR agonist.

In some embodiments, a TLR ligand is a chimeric TLR ligand (also referred to herein as a "heterofuictional" TLR ligand). In some embodiments, a chimeric TLR agonist comprises a TLR9 agonist moiety, and a TLR7 agonist moiety. In other embodiments, a chimeric TLR agonist comprises a selective TLR7 agonist and a selective TLR8 agonist. In other embodiments, a chimeric TLR agonist comprises a TLR 9 agonist and a TLR8 agonist. The following are non-limiting examples of heterofunctional TLR agonists.

In some embodiments, a chimeric TLR ligand has the following formula: $5'-X_n-CG-X_m-(B)_q-3'$, where X is any nucleotide, and n and m are independently an integer from 0 to 200, and where B is a TLR7 ligand, and q is 1, 2, 3, 4, 5, 6, 7, 8, 9, or 10.

In some embodiments, a chimeric TLR ligand has the following formula: $5'-X_n-(TCG)_p-X_m-(B)_q-3'$, where X is any nucleotide, n and m are each independently an integer from 0 to 200, where B is a TLR7 ligand, and where q and p are each independently 1, 2, 3, 4, 5, 6, 7, 8, 9, or 10.

In some embodiments, a chimeric TLR ligand has the following formula: $5'-(B)_q-X_n-CG-X_m-3'$, where X is any nucleotide, and n and m are independently an integer from 0 to 200, where B is a TLR7 ligand, and q is 1, 2, 3, 4, 5, 6, 7, 8, 9, or 10.

In some embodiments, a chimeric TLR ligand has the following formula: $5'-(B)_q-X_n-(TCG)_p-X_m-3'$, where X is any nucleotide, n and m are each independently an integer from 0 to 200, and q and p are each independently 1, 2, 3, 4, 5, 6, 7, 8, 9, or 10, and where B is a TLR7 ligand.

TLR2 Agonists

Suitable TLR2 agonists include isolated, naturally-occurring TLR2 agonists; and synthetic TLR2 agonists. TLR2 agonists isolated from a naturally-occurring source of TLR2 agonist are generally purified, e.g., the purified TLR2 agonist is at least about 80% pure, at least about 90% pure, at least about 95% pure, at least about 98% pure, at least about 99% pure, or more than 99% pure. Synthetic TLR2 agonists are prepared by standard means, and are generally at least about 80% pure, at least about 90% pure, at least about 95% pure, at least about 98% pure, at least about 99% pure, or more than 99% pure.

Suitable TLR2 agonists include TLR2 agonists that are not attached to any other compound. Suitable TLR2 agonists include TLR2 agonists that are attached, covalently or non-covalently, to a second compound. In some embodiments, a TLR2 agonist is attached to another compound directly. In other embodiments, a TLR2 agonist is attached to another compound through a linker. Suitable compounds to which a TLR2 agonist is attached include a carrier, a scaffold, and the like.

Suitable TLR2 agonists include synthetic triacylated and diacylated lipopeptides. An exemplary, non-limiting TLR2 ligand is Pam$_3$Cys (tripalmitoyl-S-glyceryl cysteine) or S-[2, 3-bis(palmitoyloxy)-(2RS)-propyl]-N-palmitoyl-(R)-cysteine, where "Pam$_3$" is "tripalmitoyl-S-glyceryl"). Aliprantis et al. (1999) *Science* 285:736-739. Derivatives of Pam$_3$Cys are also suitable TLR2 agonists, where derivatives include, but are not limited to, S-[2,3-bis(palmitoyloxy)-(2-R,S)-propyl]-N-palmitoyl-(R)-Cys-(S)-Ser-Lys$_4$-hydroxytrihydrochloride; Pam$_3$Cys-Ser-Ser-Asn-Ala; PaM$_3$Cys-Ser-(Lys)$_4$; Pam$_3$Cys-Ala-Gly; Pam$_3$Cys-Ser-Gly; Pam$_3$Cys-Ser; PaM$_3$Cys-OMe; Pam$_3$Cys-OH; PamCAG, palmitoyl-Cys ((RS)-2,3-di(palmitoyloxy)-propyl)-Ala-Gly-OH; and the like. Another non-limiting example of a suitable TLR2 agonist is Pam$_2$CSK$_4$. PaM$_2$CSK$_4$ (dipalmitoyl-S-glyceryl cysteine-serine-(lysine)$_4$; or Pam$_2$Cys-Ser-(Lys)$_4$) is a synthetic diacylated lipopeptide. Synthetic TLRs agonists have been described in the literature. See, e.g., Kellner et al. (1992) *Biol Chem Hoppe Seyler* 373:1:51-5; Seifer et al. (1990) *Biochem. J.* 26:795-802; Lee et al. (2003) *Journal of Lipid Research* 44:479-486.

In some embodiments, a suitable TLR2 agonist is a selective TLR2 agonist, e.g., a TLR2 agonist selectively activates TLR2, but does not substantially activate any other Toll-like receptor, such as TLR1, TLR3, TLR4, TLR5, TLR6, TLR7, TLR8, TLR9, or TLR10. In other embodiments, a suitable TLR2 agonist activates a TLR2, and may also activate one or more other Toll-like receptors. Such agonists are "relatively" selective, e.g., such agonists may activate two or more other TLR in addition to TLR2, but do not activate receptors other than TLR.

TLR3 Agonists

Suitable TLR3 agonists include isolated, naturally-occurring TLR3 agonists; and synthetic TLR3 agonists. TLR3 agonists isolated from a naturally-occurring source of TLR3 agonist are generally purified, e.g., the purified TLR3 agonist is at least about 80% pure, at least about 90% pure, at least about 95% pure, at least about 98% pure, at least about 99% pure, or more than 99% pure. Synthetic TLR3 agonists are prepared by standard means, and are generally at least about 80% pure, at least about 90% pure, at least about 95% pure, at least about 98% pure, at least about 99% pure, or more than 99% pure.

Suitable TLR3 agonists include TLR3 agonists that are not attached to any other compound. Suitable TLR3 agonists include TLR3 agonists that are attached, covalently or non-covalently, to a second compound. In some embodiments, a TLR3 agonist is attached to another compound directly. In other embodiments, a TLR3 agonist is attached to another compound through a linker. Suitable compounds to which a TLR3 agonist is attached include a carrier, a scaffold, and the like.

TLR3 agonists include naturally-occurring double-stranded RNA (dsRNA); synthetic ds RNA; and synthetic dsRNA analogs; and the like. Alexopoulou et al. (2001) *Nature* 413:732-738. An exemplary, non-limiting example of a synthetic ds RNA analog is poly(I:C).

TLR4 Agonists

Suitable TLR4 agonists include isolated, naturally-occurring TLR4 agonists; and synthetic TLR4 agonists. TLR4 agonists isolated from a naturally-occurring source of TLR4 agonist are generally purified, e.g., the purified TLR4 agonist is at least about 80% pure, at least about 90% pure, at least about 95% pure, at least about 98% pure, at least about 99% pure, or more than 99% pure. Synthetic TLR4 agonists are prepared by standard means, and are generally at least about 80% pure, at least about 90% pure, at least about 95% pure, at least about 98% pure, at least about 99% pure, or more than 99% pure.

Suitable TLR4 agonists include TLR4 agonists that are not attached to any other compound. Suitable TLR4 agonists include TLR4 agonists that are attached, covalently or non-covalently, to a second compound. In some embodiments, a TLR4 agonist is attached to another compound directly. In other embodiments, a TLR4 agonist is attached to another compound through a linker. Suitable compounds to which a TLR4 agonist is attached include a carrier, a scaffold, and the like.

TLR4 agonists include naturally-occurring lipopolysaccharides (LPS), e.g., LPS from a wide variety of Gram negative bacteria; derivatives of naturally-occurring LPS; synthetic LPS; bacteria heat shock protein-60 (Hsp60); mannuronic acid polymers; flavolipins; teichuronic acids; *S. pneumoniae* pneumolysin; bacterial fimbriae, respiratory syncytial virus coat protein; and the like.

TLR7 Agonists

Suitable TLR7 agonists include isolated, naturally-occurring TLR7 agonists; and synthetic TLR7 agonists. TLR7 agonists isolated from a naturally-occurring source of TLR7 agonist are generally purified, e.g., the purified TLR7 agonist is at least about 80% pure, at least about 90% pure, at least about 95% pure, at least about 98% pure, at least about 99% pure, or more than 99% pure. Synthetic TLR7 agonists are prepared by standard means, and are generally at least about 80% pure, at least about 90% pure, at least about 95% pure, at least about 98% pure, at least about 99% pure, or more than 99% pure.

Suitable TLR7 agonists include TLR7 agonists that are not attached to any other compound. Suitable TLR7 agonists include TLR7 agonists that are attached, covalently or non-covalently, to a second compound. In some embodiments, a TLR7 agonist is attached to another compound directly. In other embodiments, a TLR7 agonist is attached to another compound through a linker. Suitable compounds to which a TLR7 agonist is attached include a carrier, a scaffold, and the like.

TLR7 ligands include imidazoquinoline compounds; guanosine analogs; pyrimidinone compounds such as bropirimine and bropirimine analogs; and the like. Imidazoquinoline compounds that function as TLR7 ligands include, but are not limited to, imiquimod, (also known as Aldara, R-837, S-26308), and R-848 (also known as resiquimod, S-28463; having the chemical structure: 4-amino-2-ethoxymethyl-α, α-dimethyl-1H-imidazol[4,5-c]quinoline-1-ethanol). Suitable imidazoquinoline agents include imidazoquinoline amines, imidazopyridine amines, 6,7-fused cycloalkylimidazopyridine amines, and 1,2 bridged imidazoquinoline amines. These compounds have been described in U.S. Pat. Nos. 4,689,338, 4,929,624, 5,238,944, 5,266,575, 5,268,376, 5,346,905, 5,352,784, 5,389,640, 5,395,937, 5,494,916, 5,482,936, 5,525,612, 6,039,969 and 6,110,929. Particular species of imidazoquinoline agents that are suitable for use in a subject method include R-848 (S-28463); 4-amino-2ethoxymethyl-α, α.-dimethyl-1H-imidazo[4,5-c]quinoline-s-1-ethanol; and 1-(2-methylpropyl)-1H-imidazo[4,5-c] quinolin-4-amine (R-837 or Imiquimod). Also suitable for use is the compound 4-amino-2-(ethoxymethyl)-α,α-dimethyl-6,7,8,9-tetrahydro-1H-imidazo[4,5-c]quinoline-1-ethanol hydrate (see, e.g., BM-003 in Gorden et al. (2005) *J Immunol.* 174:1259-1268).

Suitable compounds include those having a 2-aminopyridine fused to a five membered nitrogen-containing heterocyclic ring. Such compounds include, for example, imidazoquinoline amines including but not limited to substituted imidazoquinoline amines such as, for example, arnide substituted imidazoquinoline amines, sulfonamide substituted imidazoquinoline amines, urea substituted imidazoquinoline amines, aryl ether substituted imidazoquinoline amines, heterocyclic ether substituted imidazoquinoline amines, amido ether substituted imidazoquinoline amines, sulfonamido ether substituted imidazoquinoline amines, urea substituted imidazoquinoline ethers, thioether substituted imidazoquinoline amines, and 6-, 7-, 8-, or 9-aryl or heteroaryl substituted imidazoquinoline amines; tetrahydroimidazoquinoline amines including but not limited to amide substituted tetrahydroimidazoquinoline amines, sulfonamide substituted tetrahydroimidazoquinoline amines, urea substituted tetrahydroimidazoquinoline amines, aryl ether substituted tetrahydroimidazoquinoline amines, heterocyclic ether substituted tetrahydroimidazoquinoline amines, amido ether substituted tetrahydroimidazoquinoline amines, sulfonamido ether substituted tetrahydroimidazoquinoline amines, urea substituted tetrahydroimidazoquinoline ethers, and thioether substituted tetrahydroimidazoquinoline amines; imidazopyridine amines including but not limited to amide substituted imidazopyridine amines, sulfonamido substituted imidazopyridine amines, urea substituted imidazopyridine amines, aryl ether substituted imidazopyridine amines, heterocyclic ether substituted imidazopyridine amines, amido ether substituted imidazopyridine amines, sulfonamido ether substituted imidazopyridine amines, urea substituted imidazopyridine ethers, and thioether substituted imidazopyridine amines; 1,2-bridged imidazoquinoline amines; 6,7-fused cycloalkylimidazopyridine amines; imidazonaphthyridine amines; tetrahydroimidazonaphthyridine amines; oxazoloquinoline amines; thiazoloquinoline amines; oxazolopyridine amines; thiazolopyridine amines; oxazolonaphthyridine amines; thiazolonaphthyridine amines; and 1H-imidazo dimers fused to pyridine amines, quinoline amines, tetrahydroquinoline amines, naphthyridine amines, and tetrahydronaphthyridine amines.

Suitable compounds include a substituted imidazoquinoline amine, a tetrahydroimidazoquinoline amine, an imidazopyridine amine, a 1,2-bridged imidazoquinoline amine, a 6,7-fused cycloalkylimidazopyridine amine, an imidazonaphthyridine amine, a tetrahydroimidazonaphthyridine amine, an oxazoloquinoline amine, a thiazoloquinoline amine, an oxazolopyridine amine, a thiazolopyridine amine, an oxazolonaphthyridine amine, and a thiazolonaphthyridine amine.

As used herein, a substituted imidazoquinoline amine refers to an amide substituted imidazoquinoline amine, a sulfonamide substituted imidazoquinoline amine, a urea substituted imidazoquinoline amine, an aryl ether substituted imidazoquinoline amine, a heterocyclic ether substituted imidazoquinoline amine, an amido ether substituted imidazoquinoline amine, a sulfonamido ether substituted imidazoquinoline amine, a urea substituted imidazoquinoline ether, a thioether substituted imidazoquinoline amines, or a 6-, 7-, 8-, or 9-aryl or heteroaryl substituted imidazoquinoline amine.

Guanosine analogs that function as TLR7 ligands include certain C8-substituted and N7,C8-disubstituted guanine ribonucleotides and deoxyribonucleotides, including, but not limited to, Loxoribine (7-allyl-8-oxoguanosine), 7-thia-8-oxoguanosine (TOG), 7-deazaguanosine, and 7-deazadeoxyguanosine. Lee et al. (2003) *Proc., Natl. Acad. Sci. USA* 100:6646-6651. Bropirimine (PNU-54461), a 5-halo-6-phenyl-pyrimidinone, and bropirimine analogs are described in the literature and are also suitable for use. See, e.g., Vroegop et al. (1999) *Intl. J Immunopharmacol.* 21:647-662. Additional examples of suitable C8-substituted guanosines include but are not limited to 8-mercaptoguanosine, 8-bromoguanosine, 8-methylguanosine, 8-oxo-7,8-dihydroguanosine, C8-arylamino-2'-deoxyguanosine, C8-propynyl-guanosine, C8- and N7-substituted guanine ribonucleosides such as 7-allyl-8-oxoguanosine (loxoribine) and 7-methyl-8-oxoguanosine, 8-aminoguanosine, 8-hydroxy-2'-deoxyguanosine, and 8-hydroxyguanosine.

In some embodiments a substituted guanine TLR7 ligand is monomeric. In other embodiments, a substituted guanine TLR7 ligand is multimeric. Thus, in some embodiments, a TLR7 ligand has the formula: $(B)_q$, where B is a substituted guanine TLR7 ligand, and q is 1, 2, 3, 4, 5, 6, 7, 8, 9, or 10. The individual TLR7 ligand monomers in a multimeric TLR7 ligand are linked, covalently or non-covalently, either directly to one another or through a linker.

Suitable TLR7 agonists include a TLR7 ligand as described in U.S. Patent Publication No. 2004/0162309. For example, suitable TLR7 agonist is a compound of the formula:

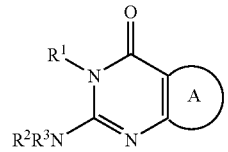

wherein each of $R^1$, $R^2$, and $R^3$ is independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl, and wherein the ring system A is a member selected from the formula:

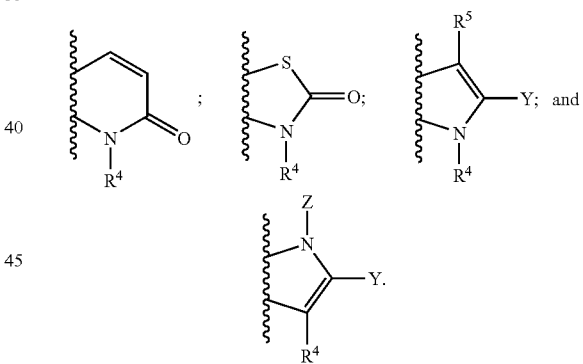

wherein the symbol Z represents substituted or unsubstituted alkyl. Y is a member selected from H, halogen, nitro, and nitroso; Y is a member selected from H, halogen, nitro, and nitroso; the symbol $R^4$ a member selected from H, substituted or unsubstituted alkyl, substituted or unsubstituted heteroalkyl; $R^5$ is a member selected from H, CN, $OR^{12}$, $C(X^1)OR^{12}$, $C(X^1)NR^{13}R^{14}$, $NR^{15}R^{16}$, $SR^{12}$, NO, halogen, substituted or unsubstituted $C_1$-$C_6$ alkyl and substituted or unsubstituted $C_1$-$C_6$ heteroalkyl. $R^{12}$ is a member selected from H, substituted or unsubstituted $C_1$-$C_6$ alkyl, substituted or unsubstituted $C_1$-$C_6$ heteroalkyl, and $C(O)R^{17}$. The symbol $R^{17}$ represents substituted or unsubstituted $C_1$-$C_6$ alkyl, or substituted or unsubstituted $C_1$-$C_6$ heteroalkyl. $X^1$ is a member selected from (=O), (=NH), and (=SH). $R^{13}$ and $R^{14}$ are each independently selected from H, substituted or unsubstituted $C_1$-$C_6$ alkyl, and substituted or unsubstituted $C_1$-$C_6$ heteroalkyl. $R^{15}$ and $R^{16}$ are each independently selected from H, O, substituted or unsubstituted $C_1$-$C_6$ alkyl, and substituted or unsubstituted $C_1$-$C_6$ heteroalkyl, or taken together, form $C(O)R^{18}$, where $R^{18}$ is a member selected from substituted or unsubstituted $C_1$-$C_6$ alkyl, and substituted or unsubstituted $C_1$-$C_6$ heteroalkyl.

In some embodiments, a TLR7 agonist is a selective TLR7 agonist, e.g., the agonist modulates cellular activity through TLR7, but does not modulate cellular activity through TLR8. TLR7-selective agonists include those shown in Tables 2, 4, and 5 of U.S. Patent Publication No. 2004/0171086. Such TLR7 selective agonist compounds include, but are not limited to, the compounds shown in Table 1, below, which compounds are listed in Table 2 of U.S. Patent Publication No. 2004/0171086.

TABLE 1

| Compound Name |
| --- |
| $N^1$-{4-[4-amino-2-(2-methoxyethyl)-6,7,8,9-tetrahydro-1H-imidazo[4,5-c]quinolin-1-yl]butyl}-4-fluoro-1-benzenesulfonamide |
| $N^1$-[4-(4-amino-2-(2-methoxyethyl)-1H-imidazo[4,5-c]quinolin-1-yl)butyl]-4-fluoro-1-benzenesulfonamide |
| N-[4-(4-amino-2-propyl-1H-imidazo[4,5-c]quinolin-1-yl)butyl]methanesulfonamide |
| N-{3-[4-amino-2-(2-methoxyethyl)-1H-imidazo[4,5-c]quinolin-1-yl]-2,2-dimethylpropyl}benzamide |
| N-(2-{2-[4-amino-2-(2-methoxyethyl)-1H-imidazo[4,5-c]quinolin-1-yl]ethoxy}ethyl)-N-methylmethanesulfonamide |
| N-(2-{2-[4-amino-2-(2-methoxyethyl)-6,7,8,9-tetrahydro-1H-imidazo[4,5-c]quinolin-1-yl]ethoxy}ethyl)benzamide |
| N-[4-(4-amino-2-methyl-1H-imidazo[4,5-c]quinolin-1-yl)butyl]cyclopentanecarboxamide |
| 1-[4-(1,1-dioxidoisothiazolidin-2-yl)butyl]-2-(2-methoxyethyl)-1H-imidazo[4,5-c]quinolin-4-amine |
| 2-methyl-1-[5-methylsulfonyl)pentyl-6,7,8,9-tetrahydro-1H-imidazo[4,5-c]quinolin-4-amine |
| N-{2-[4-amino-2-(ethoxymethyl)-6,7-dimethyl-1H-imidazo[4,5-c]pyridin-1-yl]-1,1-dimethylethyl}-N-cyclohexylurea |
| N-[2-(4-amino-2-ethyl-1H-imidazo[4,5-c]quinolin-1-yl)-1,1-dimethylethyl]benzamide |
| N-[3-(4-amino-2-butyl-1H-imidazo[4,5-c]quinolin-1-yl)-2,2-dimethylpropyl]methanesulfonamide |
| 1-[6-(methanesulfonyl)hexyl]-6,7-dimethyl-2-propyl-1H-imidazo[4,5-c]pyridin-4-amine |
| 6-(6-amino-2-propyl-1H-imidazo[4,5-c]quinolin-1-yl)-N-methoxy-N-methylhexamide |
| 1-[2,2-dimethyl-3-(methylsulfonyl)propyl]-2-(ethoxymethyl)-1H-imidazo[4,5-c]quinolin-4-amine |
| N-[4-(4-amino-2-methyl-1H-imidazo[4,5-c]quinolin-1-yl)butyl]-N-methyl-N-phenylurea |
| 1-{3-[4-amino-1-(2-methylpropyl)-1H-imidazo[4,5-c]quinolin-8-yl]phenyl}ethanone |
| 7-(4-amino-2-propyl-1H-imidazo[4,5-c]quinolin-1-yl)-2-methylheptan-2-ol |
| N-methyl-4-(4-amino-2-ethyl-1H-imidazo[4,5-c]quinolin-1-yl)butane-1-sulfonamide |
| N-(4-methoxybenzyl)-4-(4-amino-2-ethyl-1H-imidazo[4,5-c]quinolin-1-yl)butane-1-sulfonamide |
| N-{2-[4-amino-3-(ethoxymethyl)-6,7-dimethyl-1H-imidazo[4,5-c]pyridin-1-yl]-1,1-dimethylethyl}methanesulfonamide |
| 2-ethoxymethyl-1-(3-methoxypropyl)-7-(5-hydroxymethylpyridin-3-yl)-1H-imidazo[4,5-c]quinolin-4-amine |

TABLE 1-continued

| Compound Name |
| --- |
| 1-[(2,2-dimethyl-1,3-dioxolan-4-yl)methyl]-2-(ethoxymethyl)-7-(pyridin-3-yl)-1H-imidazo[4,5-c]quinolin-4-amine |
| 4-[3-(4-amino-6,7-dimethyl-2-propyl-1H-imithizo[4,5-c]pyridin-1-yl)propane-1-sulfonyl]-benzoic acid ethyl ester |
| 2-butyl-1-{2-[2-(methylsulfonyl)ethoxy]ethyl}-1H-imidazo[4,5-c]quinolin-4-amine |
| N-(2-{4-amino-2-ethoxymethyl-7-[6-(methanesulfonylamino)hexyloxy]-1H-imidazo[4,5-c]quinolin-1-yl}-1,1-dimethylethyl)methanesulfonamide |
| N-(6-{[4-amino-2-ethoxymethyl-1-(2-methanesulfonylamino-2-methylpropyl)-1H-imidazo[4,5-c]quinolin-7-yl]oxy}hexyl)acetamide |
| 1-[4-(1,1-dioxidoisothiazolidin-2-yl)butyl]-2-ethoxymethyl-7-(pyridin-3-yl)-1H-imidazo[4,5-c]quinolin-4-amine |
| 1-[4-(1,1-dioxidoisothiazolidin-2-yl)butyl]-2-ethoxymethyl-7-(pyridin-4-yl)-1H-imidazo[4,5-c]quinolin-4-amine |
| 1-[4-(1,1-dioxidoisothiazolidin-2-yl)butyl]-2-ethoxymethyl-7-phenyl-1H-imidazo[4,5-c]quinolin-4-amine |
| 2-(ethoxymethyl)-1-{[1-(methylsulfonyl)piperidin-4-yl]methyl}-7-(pyridin-3-yl)-1H-imidazo[4,5-c]quinolin-4-amine |
| 2-(ethoxymethyl)-1-[(1-isobutyrylpiperidin-4-yl)methyl]-7-(pyridin-3-yl)-1H-imidazo[4,5-c]quinolin-4-amine |
| 2-(ethoxymethyl)-1-{[1-(morpholic-4-ylcarbonyl)piperidin-4-yl]methyl}-7-(pyridin-3-yl)-1H-imidazo[4,5-c]quinolin-4-amine |
| Cyclopropanecarboxylic acid [3-(4-amino-2-propyl-1H-imidazo[4,5-c]quinolin-1-yl)propoxy]amide |
| Isopropylcarbamic acid 4-amino-2-(2-methoxyethyl)-1-propyl-1H-imidazo[4,5-c]quinolin-7-yl ester |
| Ethyl 4-(4-amino-2-propyl-1H-imidazo[4,5-c]quinolin-1-yl)butyrate |
| 1-[4-amino-2-ethyl-7-(pyridin-3-yl)-1H-imidazo[4,5-c]quinolin-1-yl]-2-methylpropan-2-ol |
| 1-(4-amino-2-ethyl-7-[5-{hydroxymethyl)pyridin-3-yl]-1H-imidazo[4,5-c]quinolin-1-yl}-2-methylpropan-2-ol |
| 1-(3-[4-amino-2-(2-methoxyethyl)-8-(pyridin-3-yl)-1H-imidazo[4,5-c]quinolin-1-yl]propyl]pyrrolidin-2-one |
| N-(2-{4-amino-2-ethoxymethyl-7-[6-(methanesulfonylamino)hexyloxy]-1H-imidazo[4,5-c]quinolin-1-yl}-1,1-dimethylethyl)acetamide |
| 1-{3-[4-amino-7-(3-hydroxymethylphenyl)-2-(2-methoxyethyl)-1H-imidazo[4,5-c]quinolin-1-yl]propyl}pyrrolidin-2-one |
| N-{4-[4-amino-2-ethoxymethyl-7-(pyridin-3-yl)-1H-imidazo[4,5-c]quinolin-1-yl]butyl}-N'-propylurea |
| N-{4-[4-amino-2-ethoxymethyl-7-(pyridin-3-yl)-1H-imidazo[4,5-c]quinolin-1-yl]butyl}butyramide |
| 5-(4-amino-2-propyl-1H-imidazo[4,5-c]quinolin-1-yl)-4,4-dimethylpentan-2-one |
| 1-cyclohexylmethyl-2-ethoxymethyl-7-(5-hydroxymethylpyridin-3-yl)-1H-imidazo[4,5-c]quinolin-4-amine |
| N,N-dimethyl-5-(4-amino-2-ethoxymethyl-1H-imidazo[4,5-c]quinolin-1-yl)pentane-1-sulfonamide |
| N-{3-[(4-amino-2-ethoxymethyl-1H-imidazo[4,5-c]quinolin-1-yl)amino]propyl}methanesulfonamide |
| N,N-dimethyl-4-(4-amino-2-ethoxymethyl-1H- |

TABLE 1-continued

Compound Name imidazo[4,5-c]quinolin-1-yl)butane-1-sulfonamide

Additional suitable TLR7 selective agonists include, but are not limited to, 2-(ethoxymethyl)-1-(2-methylpropyl)-1H-imidazo [4,5-c]quinolin-4-amine (see, e.g., Example 40, U.S. Pat. No. 5,389,640); 2-methyl-1-[2-(3-pyridin-3-ylpropoxy) ethyl]-1H-imidazo [4,5-c]quinolin-4-amine (see, e.g., WO 02/46193, Example 34); N-(2-{2-[4-amino-2-(2-methoxyethyl)-1H-imidazo [4,5-c]quinolin-1-yl]ethoxy}ethyl)-N-methylcyclohexanecarboxamide (see, e.g., U.S. Patent Publication No. 2004/0171086; IRM3; Table 4); 1-[2-(benzyloxy)ethyl]-2-methyl-1H-imidazo[4,5-c]quinolin-4-amine (see, e.g., WO 02/46189, Example 127); N-{8-[4-amino-2-(2-methyoxyethyl)-1H-imidazo[4,5-c]quinolin-1-yl]octyl}-N'-phenylurea (see, e.g., U.S. Patent Publication No. 2004/0171086; IRM5; Table 4); 2-butyl-1-[5-(methylsulfonyl)pentyl]-1H-imidazo[4,5-c]quinolin-4-amine (see, e.g., WO 02/46192, Example 11); N-{3-[4-amino-2-(2-methoxyethyl)-1 H-imidazo[4,5-c]quinolin-1-yl]propyl}-4-methylbenzenesulfonamide (see, e.g., U.S. Pat. No. 6,331,539); and N-[4-(4-amino-2-ethyl-1H-imidazo[4,5-c]quinolin-1-yl)butyl]cyclohexanecarboxamide (see, e.g., U.S. Patent Publication No. 2004/0171086; IRM8; Table 4). Also suitable for use is the TLR7-selective agonist N-[4-(4-amino-2-ethyl-1H-imidazo[4,5-c]quinolin-1-yl)butyl-]methanesulfonamide (see, e.g., BM-001 in Gorden et al. (2005) *J. Immunol.* 174:1259-1268).

TLR8 Agonists

Suitable TLR8 agonists include isolated, naturally-occurring TLR8 agonists; and synthetic TLR8 agonists. TLR8 agonists isolated from a naturally-occurring source of TLR8 agonist are generally purified, e.g., the purified TLR8 agonist is at least about 80% pure, at least about 90% pure, at least about 95% pure, at least about 98% pure, at least about 99% pure, or more than 99% pure. Synthetic TLR8 agonists are prepared by standard means, and are generally at least about 80% pure, at least about 90% pure, at least about 95% pure, at least about 98% pure, at least about 99% pure, or more than 99% pure.

Suitable TLR8 agonists include TLR8 agonists that are not attached to any other compound. Suitable TLR8 agonists include TLR8 agonists that are attached, covalently or non-covalently, to a second compound. In some embodiments, a TLR8 agonist is attached to another compound directly. In other embodiments, a TLR8 agonist is attached to another compound through a linker. Suitable compounds to which a TLR8 agonist is attached include a carrier, a scaffold, and the like.

TLR8 agonists include, but are not limited to, compounds such as R-848, and derivatives and analogs thereof. Suitable TLR8 agonists include compounds having a 2-aminopyridine fused to a five membered nitrogen-containing heterocyclic ring. Such compounds include, for example, imidazoquinoline amines including but not limited to substituted imidazoquinoline amines such as, for example, amide substituted imidazoquinoline amines, sulfonamide substituted imidazoquinoline amines, urea substituted imidazoquinoline amines, aryl ether substituted imidazoquinoline amines, heterocyclic ether substituted imidazoquinoline amines, amido ether substituted imidazoquinoline amines, sulfonamido ether substituted imidazoquinoline amines, urea substituted imidazoquinoline ethers, thioether substituted imidazoquinoline amines, and 6-, 7-, 8-, or 9-aryl or heteroaryl substituted imidazoquinoline amines; tetrahydroimidazoquinoline amines including but not limited to amide substituted tetrahydroimidazoquinoline amines, sulfonamide substituted tetrahydroimidazoquinoline amines, urea substituted tetrahydroimidazoquinoline amines, aryl ether substituted tetrahydroimidazoquinoline amines, heterocyclic ether substituted tetrahydroimidazoquinoline amines, amido ether substituted tetrahydroimidazoquinoline amines, sulfonamido ether substituted tetrahydroimidazoquinoline amines, urea substituted tetrahydroimidazoquinoline ethers, and thioether substituted tetrahydroimidazoquinoline amines; imidazopyridine amines including but not limited to amide substituted imidazopyridine amines, sulfonamide substituted imidazopyridine amines, urea substituted imidazopyridine amines, aryl ether substituted imidazopyridine amines, heterocyclic ether substituted imidazopyridine amines, amido ether substituted imidazopyridine amines, sulfonamido ether substituted imidazopyridine amines, urea substituted imidazopyridine ethers, and thioether substituted imidazopyridine amines; 1,2-bridged imidazoquinoline amines; 6,7-fused cycloalkylimidazopyridine amines; imidazonaphthyridine amines; tetrahydroimidazonaphthyridine amines; oxazoloquinoline amines; thiazoloquinoline amines; oxazolopyridine amines; thiazolopyridine amines; oxazolonaphthyridine amines; thiazolonaphthyridine amines; and 1H-imidazo dimers fused to pyridine amines, quinoline amines, tetrahydroquinoline amines, naphthyridine amines, or tetrahydronaphthyridine amines.

In one particular embodiment, the TLR8 agonist is an amide substituted imidazoquinoline amine. In an alternative embodiment, the TLR8 agonist is a sulfonamide substituted imidazoquinoline amine. In another alternative embodiment, the TLR8 agonist is a urea substituted imidazoquinoline amine. In another alternative embodiment, the TLR8 agonist is an aryl ether substituted imidazoquinoline amine. In another alternative embodiment, the TLR8 agonist is a heterocyclic ether substituted imidazoquinoline amine. In another alternative embodiment, the TLR8 agonist is an amido ether substituted imidazoquinoline amine. In another alternative embodiment, the TLR8 agonist is a sulfonamido ether substituted imidazoquinoline amine. In another alternative embodiment, the TLR8 agonist is a urea substituted imidazoquinoline ether. In another alternative embodiment, the TLR8 agonist is a thioether substituted imidazoquinoline amine. In another alternative embodiment, the TLR8 agonist is a 6-, 7-, 8-, or 9-aryl or heteroaryl substituted imidazoquinoline amine.

In another alternative embodiment, the TLR8 agonist is an amide substituted tetrahydroimidazoquinoline amine. In another alternative embodiment, the TLR8 agonist is a sulfonamide substituted tetrahydroimidazoquinoline amine. In another alternative embodiment, the TLR8 agonist is a urea substituted tetrahydroimidazoquinoline amine.

In another alternative embodiment, the TLR8 agonist is an aryl ether substituted tetrahydroimidazoquinoline amine. In another alternative embodiment, the TLR8 agonist is a heterocyclic ether substituted tetrahydroimidazoquinoline amine. In another alternative embodiment, the TLR8 agonist is an amido ether substituted tetrahydroimidazoquinoline amine. In another alternative embodiment, the TLR8 agonist is a sulfonamido ether substituted tetrahydroimidazoquinoline amine. In another alternative embodiment, the TLR8 agonist is a urea substituted tetrahydroimidazoquinoline ether. In another alternative embodiment, the TLR8 agonist is a thioether substituted tetrahydroimidazoquinoline amine.

In another alternative embodiment, the TLR8 agonist is an amide substituted imidazopyridine amines. In another alternative embodiment, the TLR8 agonist is a sulfonamide substituted imidazopyridine amine. In another alternative embodiment, the TLR8 agonist is a urea substituted imidazopyridine amine. In another alternative embodiment, the TLR8 agonist is an aryl ether substituted imidazopyridine amine. In another alternative embodiment, the TLR8 agonist is a heterocyclic ether substituted imidazopyridine amine. In another alternative embodiment, the TLR8 agonist is an amido ether substituted imidazopyridine amine. In another alternative embodiment, the TLR8 agonist is a sulfonamido ether substituted imidazopyridine amine. In another alternative embodiment, the TLR8 agonist is a urea substituted imidazopyridine ether. In another alternative embodiment, the TLR8 agonist is a thioether substituted imidazopyridine amine.

In another alternative embodiment, the TLR8 agonist is a 1,2-bridged imidazoquinoline amine. In another alternative embodiment, the TLR8 agonist is a 6,7-fused cycloalkylimidazopyridine amine.

In another alternative embodiment, the TLR8 agonist is an imidazonaphthyridine amine. In another alternative embodiment, the TLR8 agonist is a tetrahydroimidazonaphthyridine amine. In another alternative embodiment, the TLR8 agonist is an oxazoloquinoline amine. In another alternative embodiment, the TLR8 agonist is a thiazoloquinoline amine. In another alternative embodiment, the TLR8 agonist is an oxazolopyridine amine. In another alternative embodiment, the TLR8 agonist is a thiazolopyridine amine. In another alternative embodiment, the TLR8 agonist is an oxazolonaphthyridine amine. In another alternative embodiment, the TLR8 agonist is a thiazolonaphthyridine amine.

In yet another alternative embodiment, the TLR8 agonist is a 1H-imidazo dimer fused to a pyridine amine, quinoline amine, tetrahydroquinoline amine, naphthyridine amine, or a tetrahydronaphthyridine amine.

In some embodiments, the TLR8 agonist is a selective TLR8 agonist, e.g., the agonist modulates cellular activity through TLR8, but does not modulate cellular activity through TLR7. TLR8-selective agonists include those shown in Tables 1, 4, and 5 of U.S. Patent Publication No. 2004/0171086. Such TLR8 selective agonist compounds include, but are not limited to, the compounds shown in Table 2, below, which compounds are listed in Table 1 of U.S. Patent Publication No. 2004/0171086.

TABLE 2

| Compound Name |
| --- |
| N-{4-[4-amino-2-(2-methoxyethyl)-1H-imidazo[4,5-c]quinolin-1-yl]butyl}quinolin-3-carboxamide |
| N-{4-[4-amino-2-(2-methoxyethyl)-1H-imidazo[4,5-c]quinolin-1-yl]butyl}quinoxoline-2-carboxamide |
| N-[4-(4-amino-2-propyl-1H-imidazo[4,5-c]quinolin-1-yl)butyl]morpholine-4-carboxamide |

Other suitable TLR8-selective agonists include, but are not limited to, 2-propylthiazolo[4,5-c]quinolin-4-amine (see, e.g., U.S. Pat. No. 6,110,929, Example 12); $N^1$-[2-(4-amino-2-butyl-1H-imidazo[4,5-c][1,5]naphthridin-1-yl)ethyl]-2-amino-4-methylpentanamide (see, e.g., U.S. Pat. No. 6,194,425, Example 102); $N^1$-[4-(4-amino-1H-imidazo[4,5-c]quinolin-1-yl)butyl]-2-phenoxybenzamide (see, e.g., U.S. Pat. No. 6,451,810); $N^1$-[2-(4-amino-2-butyl-1H-imidazo[4,5-c]quinolin-1-yl)ethyl]-1-propanesulfonamide (see, e.g., U.S. Pat. No. 6,331,539, Example 17); N-{2-[2-(4-amino-2-ethyl-1H-imidazo[4,5-c]quinolin-1-yl)ethyoxy]ethyl}-N'-phenylurea (see, e.g., U.S. Patent Publication No. 2004/0171086, IRM13, Table 4 and Table 5); 1-{4-[3,5-dichlorophenyl)thio]butyl}-2-ethyl-1H-imidazo[4,5-c]quinolin-4-amine ((see, e.g., U.S. Patent Publication No. 2004/0171086, IRM14, Table 4 and Table 5); N-{2-[4-amino-2-(ethoxymethyl)-1H-imidazo[4,5-c]quinolin-1-yl]ethyl}-N'-(3-cyanophenyl)urea (see, e.g., WO 00/76518; and U.S. Patent Publication No. 2004/0171086, IRM15, Table 4 and Table 5); and 4-amino-α,α-dimethyl-2-methoxyethyl-1H-imidazo[4,5-c]quinoline-1-ethanol (see, e.g., U.S. Pat. No. 5,389,640, Example 111). Included for use as TLR8-selective agonists are the compounds depicted in Tables 4 and 5 of U.S. Patent Publication No. 2004/0171086. Also suitable for use is the compound 2-propylthiazolo-4,5-c]quinolin-4-amine (see, e.g., BM-002 in Gorden et al. (2005) supra).

TLR9 Agonists

Suitable TLR9 agonists include isolated, naturally-occurring TLR9 agonists; and synthetic TLR9 agonists. TLR9 agonists isolated from a naturally-occurring source of TLR9 agonist are generally purified, e.g., the purified TLR9 agonist is at least about 80% pure, at least about 90% pure, at least about 95% pure, at least about 98% pure, at least about 99% pure, or more than 99% pure. Synthetic TLR9 agonists are prepared by standard means, and are generally at least about 80% pure, at least about 90% pure, at least about 95% pure, at least about 98% pure, at least about 99% pure, or more than 99% pure.

Suitable TLR9 agonists include TLR9 agonists that are not attached to any other compound. Suitable TLR9 agonists include TLR9 agonists that are attached, covalently or non-covalently, to a second compound. In some embodiments, a TLR9 agonist is attached to another compound directly. In other embodiments, a TLR9 agonist is attached to another compound through a linker. Suitable compounds to which a TLR9 agonist is attached include a carrier, a scaffold, and the like.

Examples of TLR9 agonists (also referred to herein as "TLR9 ligands") include nucleic acids comprising the sequence 5'-CG-3' (a "CpG nucleic acid"), particularly where the C is unmethylated. The terms "polynucleotide," and "nucleic acid," as used interchangeably herein in the context of TLR9 ligand molecules, refer to a polynucleotide of any length, and encompasses, inter alia, single- and double-stranded oligonucleotides (including deoxyribonucleotides, ribonucleotides, or both), modified oligonucleotides, and oligonucleosides, alone or as part of a larger nucleic acid construct, or as part of a conjugate with a non-nucleic acid molecule such as a polypeptide. Thus a TLR9 ligand may be, for example, single-stranded DNA (ssDNA), double-stranded DNA (dsDNA), single-stranded RNA (ssRNA) or double-stranded RNA (dsRNA). TLR9 ligands also encompasses crude, detoxified bacterial (e.g., mycobacterial) RNA or DNA, as well as enriched plasmids enriched for a TLR9 ligand. In some embodiments, a "TLR9 ligand-enriched plasmid" refers to a linear or circular plasmid that comprises or is engineered to comprise a greater number of CpG motifs than normally found in mammalian DNA.

Exemplary, non-limiting TLR9 ligand-enriched plasmids are described in, for example, Roman et al. (1997) Nat Med. 3(8):849-54. Modifications of oligonucleotides include, but are not limited to, modifications of the 3'OH or 5'OH group, modifications of the nucleotide base, modifications of the sugar component, and modifications of the phosphate group.

A TLR9 ligand may comprise at least one nucleoside comprising an L-sugar. The L-sugar may be deoxyribose, ribose, pentose, deoxypentose, hexose, deoxyhexose, glucose, galactose, arabinose, xylose, lyxose, or a sugar "analog" cyclopentyl group. The L-sugar may be in pyranosyl or furanosyl form.

TLR9 ligands generally do not provide for, nor is there any requirement that they provide for, expression of any amino acid sequence encoded by the polynucleotide, and thus the sequence of a TLR9 ligand may be, and generally is, non-coding. TLR9 ligands may comprise a linear double or single-stranded molecule, a circular molecule, or can comprise both linear and circular segments. TLR9 ligands may be single-stranded, or may be completely or partially double-stranded.

In some embodiments, a TLR9 ligand for use in a subject method is an oligonucleotide, e.g., consists of a sequence of from about 5 nucleotides to about 200 nucleotides, from about 10 nucleotides to about 100 nucleotides, from about 12 nucleotides to about 50 nucleotides, from about 15 nucleotides to about 25 nucleotides, from 20 nucleotides to about 30 nucleotides, from about 5 nucleotides to about 15 nucleotides, from about 5 nucleotides to about 10 nucleotides, or from about 5 nucleotides to about 7 nucleotides in length. In some embodiments, a TLR9 ligand that is less than about 15 nucleotides, less than about 12 nucleotides, less than about 10 nucleotides, or less than about 8 nucleotides in length is associated with a larger molecule, e.g., adsorbed onto an insoluble support, as described below.

In some embodiments, a TLR9 ligand does not provide for expression of a peptide or polypeptide in a eukaryotic cell, e.g., introduction of a TLR9 ligand into a eukaryotic cell does not result in production of a peptide or polypeptide, because the TLR9 ligand does not provide for transcription of an mRNA encoding a peptide or polypeptide. In these embodiments, a TLR9 ligand lacks promoter regions and other control elements necessary for transcription in a eukaryotic cell.

A TLR9 ligand can be isolated from a bacterium, e.g., separated from a bacterial source; produced by synthetic means (e.g., produced by standard methods for chemical synthesis of polynucleotides); produced by standard recombinant methods, then isolated from a bacterial source; or a combination of the foregoing. In many embodiments, a TLR9 ligand is purified, e.g., is at least about 80%, at least about 90%, at least about 95%, at least about 98%, at least about 99%, or more, e.g., 99.5%, 99.9%, or more, pure. In many embodiments, the TLR9 ligand is chemically synthesized, then purified.

In other embodiments, a TLR9 ligand is part of a larger nucleotide construct (e.g., a plasmid vector, a viral vector, or other such construct). A wide variety of plasmid and viral vector are known in the art, and need not be elaborated upon here. A large number of such vectors have been described in various publications, including, e.g., *Current Protocols in Molecular Biology*, (F. M. Ausubel, et al., Eds. 1987, and updates). Many vectors are commercially available.

In general, a TLR9 ligand used in a subject composition comprises at least one unmethylated CpG motif. The relative position of any CpG sequence in a polynucleotide in certain mammalian species (e.g., rodents) is 5'-CG-3' (i.e., the C is in the 5' position with respect to the G in the 3' position).

In some embodiments, a TLR9 ligand comprises a central palindromic core sequence comprising at least one CpG sequence, where the central palindromic core sequence contains a phosphodiester backbone, and where the central palindromic core sequence is flanked on one or both sides by phosphorothioate backbone-containing polyguanosine sequences.

In other embodiments, a TLR9 ligand comprises one or more TCG sequences at or near the 5' end of the nucleic acid;

and at least two additional CG dinucleotides. In some of these embodiments, the at least two additional CG dinucleotides are spaced three nucleotides, two nucleotides, or one nucleotide apart. In some of these embodiments, the at least two additional CG dinucleotides are contiguous with one another. In some of these embodiments, the TLR9 ligand comprises (TCG)n, where n=one to three, at the 5' end of the nucleic acid. In other embodiments, the TLR9 ligand comprises (TCG)n, where n=one to three, and where the (TCG)n sequence is flanked by one nucleotide, two nucleotides, three nucleotides, four nucleotides, or five nucleotides, on the 5' end of the (TCG)n sequence.

Exemplary consensus CpG motifs of TLR9 ligands useful in the invention include, but are not necessarily limited to:
- 5'-Purine-Purine-(C)-(G)-Pyrimidine-Pyrimidine-3', in which the TLR9 ligand comprises a CpG motif flanked by at least two purine nucleotides (e.g., GG, GA, AG, AA, II, etc.,) and at least two pyrimidine nucleotides (CC, TT, CT, TC, UU, etc.);
- 5'-Purine-TCG-Pyrimidine-Pyrimidine-3';
- 5'-TCG-N-N-3'; where N is any base;
- 5'-$N_x(CG)_nN_y$, where N is any base, where x and y are independently any integer from 0 to 200, e.g., 0, 1, 2, 3, 4, 5, 6, 7, 8, 9, 10, 11-15, 16-20, 21-25, 25-30, 30-50, 50-75, 75-100, 100-150, or 150-200; and n is any integer that is 1 or greater, e.g., 1, 2, 3, 4, 5, 6, 7, 8, 9, 10, or greater.
- 5'-$N_x(TCG)_nN_y$, where N is any base, where x and y are independently any integer from 0 to 200, e.g., 0, 1, 2, 3, 4, 5, 6, 7, 8, 9, 10, 11-15, 16-20, 21-25, 25-30, 30-50, 50-75, 75-100, 100-150, or 150-200; and n is any integer that is 1 or greater, e.g., 1, 2, 3, 4, 5, 6, 7, 8, 9, 10, or greater.
- 5'-$(TCG)_n$-3', where n is any integer that is 1 or greater, e.g., to provide a TCG-based TLR9 ligand (e.g., where n=3, the polynucleotide comprises the sequence 5'-TCGNNTCGNNTCG-3'; SEQ ID NO:1);
- 5'$N_m$-$(TCG)_n$-$N_p$-3', where N is any nucleotide, where m is zero, one, two, or three, where n is any integer that is 1 or greater, and where p is one, two, three, or four;
- 5'$N_m$-$(TCG)_n$-$N_p$-3', where N is any nucleotide, where m is zero to 5, and where n is any integer that is 1 or greater, where p is four or greater, and where the sequence N-N-N-N comprises at least two CG dinucleotides that are either contiguous with each other or are separated by one nucleotide, two nucleotides, or three nucleotides; and
- 5'-Purine-Purine -CG-Pyrimidine-TCG-3'.

A non-limiting example of a TLR9 ligand comprising 5'-$(TCG)_n$-3', where n is any integer that is 1 or greater, is a TLR9 ligand comprising the sequence 5' TCGTCGTTTTGTCGTTTTGTCGTT 3' (SEQ ID NO:2).

Where a nucleic acid TLR9 ligand comprises a sequence of the formula: 5'-$N_m$-(TCG)-$N_p$-3', where N is any nucleotide, where m is zero to 5, and where n is any integer that is 1 or greater, where p is four or greater, and where the sequence N-N-N-N comprises at least two CG dinucleotides that are either contiguous with each other or are separated by one nucleotide, two nucleotides, or three nucleotides, exemplary TLR9 ligands useful in the invention include, but are not necessarily limited to:

(1) a sequence of the formula in which n=2, and $N_p$ is NNCGNNCG;

(2) a sequence of the formula in which n=2, and $N_p$ is AACGTTCG;

(3) a sequence of the formula in which n=2, and $N_p$ is TTCGAACG;

(4) a sequence of the formula in which n=2, and $N_p$ is TACG-TACG;
(5) a sequence of the formula in which n=2, and $N_p$ is ATC-GATCG;
(6) a sequence of the formula in which n=2, and $N_p$ is CGCGCGCG;
(7) a sequence of the formula in which n=2, and $N_p$ is GCCG-GCCG;
(8) a sequence of the formula in which n=2, and $N_p$ is CCCGGGCG;
(9) a sequence of the formula in which n=2, and $N_p$ is GGCGCCCG;
(10) a sequence of the formula in which n=2, and $N_p$ is CCCGTTCG;
(11) a sequence of the formula in which n=2, and $N_p$ is GGCGTTCG;
(12) a sequence of the formula in which n=2, and $N_p$ is TTCGCCCG;
(13) a sequence of the formula in which n=2, and $N_p$ is TTCGGGCG;
(14) a sequence of the formula in which n=2, and $N_p$ is AACGCCCG;
(15) a sequence of the formula in which n=2, and $N_p$ is AACGGGCG;
(16) a sequence of the formula in which n=2, and $N_p$ is CCCGAACG; and
(17) a sequence of the formula in which n=2, and $N_p$ is GGCGAACG; and where, in any of 1-17, m=zero, one, two, or three.

Where a nucleic acid TLR9 ligand comprises a sequence of the formula: 5'$N_m$-(TCG)n-$N_p$-3', where N is any nucleotide, where m is zero, one, two, or three, where n is any integer that is 1 or greater, and where p is one, two, three, or four, exemplary TLR9 ligands useful in the invention include, but are not necessarily limited to:
(1) a sequence of the formula where m=zero, n=1, and $N_p$ is T-T-T;
(2) a sequence of the formula where m=zero, n=1, and $N_p$ is T-T-T-T;
(3) a sequence of the formula where m=zero, n=1, and $N_p$ is C-C-C-C;
(4) a sequence of the formula where m=zero, n=1, and $N_p$ is A-A-A-A;
(5) a sequence of the formula where m=zero, n=1, and $N_p$ is A-G-A-T;
(6) a sequence of the formula where $N_m$ is T, n=1, and $N_p$ is T-T-T;
(7) a sequence of the formula where $N_m$ is A, n=1, and $N_p$ is T-T-T;
(8) a sequence of the formula where $N_m$ is C, n=1, and $N_p$ is T-T-T;
(9) a sequence of the formula where $N_m$ is G, n=1, and $N_p$ is T-T-T;
(10) a sequence of the formula where $N_m$ is T, n=1, and $N_p$ is A-T-T;
(11) a sequence of the formula where $N_m$ is A, n=1, and $N_p$ is A-T-T; and
(12) a sequence of the formula where $N_m$ is C, n=1, and $N_p$ is A-T-T.

The core structure of a TLR9 ligand useful in the invention may be flanked upstream and/or downstream by any number or composition of nucleotides or nucleosides. In some embodiments, the core sequence of a TLR9 ligand is at least 6 bases or 8 bases in length, and the complete TLR9 ligand (core sequences plus flanking sequences 5', 3' or both) is usually between 6 bases or 8 bases, and up to about 200 bases in length.

Exemplary DNA-based TLR9 ligands useful in the invention include, but are not necessarily limited to, polynucleotides comprising one or more of the following nucleotide sequences: AGCGCT, AGCGCC, AGCGTT, AGCGTC, AACGCT, AACGCC, AACGTT, AACGTC, GGCGCT, GGCGCC, GGCGTT, GGCGTC, GACGCT, GACGCC, GACGTT, GACGTC, GTCGTC, GTCGCT, GTCGTT, GTCGCC, ATCGTC, ATCGCT, ATCGTT, ATCGCC, TCGTCG, and TCGTCGTCG.

Additional exemplary TLR9 ligands useful in the invention include, but are not necessarily limited to, polynucleotides comprising one or more of the following nucleotide sequences: TCGXXXX, TCGAXXX, XTCGXXX, XTC-GAXX, TCGTCGA, TCGACGT, TCGAACG, TCGAGAT, TCGACTC, TCGAGCG, TCGATTT, TCGCTTT, TCG-GTTT, TCGTTTT, TCGTCGT, ATCGATT, TTCGTTT, TTCGATT, ACGTTCG, AACGTTC, TGACGTT, TGTCGTT, TCGXXX, TCGAXX, TCGTCG, AACGTT, ATCGAT, GTCGTT, GACGTT, TCGXX, TCGAX, TCGAT, TCGTT, TCGTC, TCGA, TCGT, TCGX, and TCG (where "X" is any nucleotide).

Exemplary DNA-based TLR9 ligands useful in the invention include, but are not necessarily limited to, polynucleotides comprising the following octameric nucleotide sequences: AGCGCTCG, AGCGCCCG, AGCGTTCG, AGCGTCCG, AACGCTCG, AACGCCCG, AACGTTCG, AACGTCCG, GGCGCTCG, GGCGCCCG, GGCGTTCG, GGCGTCCG, GACGCTCG, GACGCCCG, GACGTTCG, and GACGTCCG.

A TLR9 ligand useful in carrying out a subject method can comprise one or more of any of the above CpG motifs. For example, a TLR9 ligand useful in the invention can comprise a single instance or multiple instances (e.g., 2, 3, 4, 5 or more) of the same CpG motif. Alternatively, a TLR9 ligand can comprise multiple CpG motifs (e.g., 2, 3, 4, 5 or more) where at least two of the multiple CpG motifs have different consensus sequences, or where all CpG motifs in the TLR9 ligand have different consensus sequences.

A TLR9 ligand useful in the invention may or may not include palindromic regions. If present, a palindrome may extend only to a CpG motif, if present, in the core hexamer or octamer sequence, or may encompass more of the hexamer or octamer sequence as well as flanking nucleotide sequences.

Multimeric TLR9 Ligands

In some embodiments, a TLR9 ligand is multimeric. A multimeric TLR9 ligand comprises two, three, four, five, six, seven, eight, nine, ten, or more individual (monomeric) nucleic acid TLR9 ligands, as described above, linked via non-covalent bonds, linked via covalent bonds, and either linked directly to one another, or linked via one or more spacers. Suitable spacers include nucleic acid and non-nucleic acid molecules, as long as they are biocompatible. In some embodiments, multimeric TLR9 ligand comprises a linear array of monomeric TLR9 ligands. In other embodiments, a multimeric TLR9 ligand is a branched, or dendrimeric, array of monomeric TLR9 ligands.

Multimeric TLR9 ligand complexes can be formed with non-covalent interactions, such as ionic bonds, hydrophobic interactions, hydrogen bonds and/or van der Waals attractions. For example, a multimeric TLR9 ligand can be a non-covalently linked aggregate of monomeric TLR9 ligands.

In some embodiments, a multimeric TLR9 ligand forms aggregates in vivo and/or in vitro. In some embodiments, a multimeric TLR9 ligand forms a secondary structure(s) near the core CpG motifs. In some embodiments, a multimeric TLR9 ligand comprises both a multimerization domain and a receptor binding CpG domain, which multimerization domain and receptor binding CpG domain are spatially distinct.

In some embodiments, a multimeric TLR9 ligand has the general structure $X_n$, where X is a nucleic acid TLR9 ligand as described above, and having a length of from about 6 nucleotides to about 200 nucleotides, e.g., from about 6 nucleotides to about 8 nucleotides, from about 8 nucleotides to about 10 nucleotides, from about 10 nucleotides to about 12 nucleotides, from about 12 nucleotides to about 15 nucleotides, from about 15 nucleotides to about 20 nucleotides, from about 20 nucleotides to about 25 nucleotides, from about 25 nucleotides to about 30 nucleotides, from about 30 nucleotides to about 40 nucleotides, from about 40 nucleotides to about 50 nucleotides, from about 50 nucleotides to about 60 nucleotides, from about 60 nucleotides to about 70 nucleotides, from about 70 nucleotides to about 80 nucleotides, from about 80 nucleotides to about 90 nucleotides, from about 90 nucleotides to about 100 nucleotides, from about 100 nucleotides to about 125 nucleotides, from about 125 nucleotides to about 150 nucleotides, from about 150 nucleotides to about 175 nucleotides, or from about 175 nucleotides to about 200 nucleotides; and where n is any number from one to about 100, e.g., n=1, 2, 3, 4, 5, 6, 7, 8, 9, 10, from 10 to about 15, from 15 to about 20, from 20 to about 25, from 25 to about 30, from 30 to about 40, from 40 to about 50, from 50 to about 60, from 60 to about 70, from 70 to about 80, from 80 to about 90, or from 90 to about 100.

In some embodiments, a multimeric TLR9 ligand has the general structure $(X_1)_n(X_2)_n$ where X is a nucleic acid TLR9 ligand as described above, and having a length of from about 6 nucleotides to about 200 nucleotides, e.g., from about 6 nucleotides to about 8 nucleotides, from about 8 nucleotides to about 10 nucleotides, from about 10 nucleotides to about 12 nucleotides, from about 12 nucleotides to about 15 nucleotides, from about 15 nucleotides to about 20 nucleotides, from about 20 nucleotides to about 25 nucleotides, from about 25 nucleotides to about 30 nucleotides, from about 30 nucleotides to about 40 nucleotides, from about 40 nucleotides to about 50 nucleotides, from about 50 nucleotides to about 60 nucleotides, from about 60 nucleotides to about 70 nucleotides, from about 70 nucleotides to about 80 nucleotides, from about 80 nucleotides to about 90 nucleotides, from about 90 nucleotides to about 100 nucleotides, from about 100 nucleotides to about 125 nucleotides, from about 125 nucleotides to about 150 nucleotides, from about 150 nucleotides to about 175 nucleotides, or from about 175 nucleotides to about 200 nucleotides; and where n is any number from one to about 100, e.g., n=1, 2, 3, 4, 5, 6, 7, 8, 9, 10, from 10 to about 15, from 15 to about 20, from 20 to about 25, from 25 to about 30, from 30 to about 40, from 40 to about 50, from 50 to about 60, from 60 to about 70, from 70 to about 80, from 80 to about 90, or from 90 to about 100. In these embodiments, X and $X_2$ differ in nucleotide sequence from one another by at least one nucleotide, and may differ in nucleotide sequence from one another by two, three, four, five, six, seven, eight, nine, ten, or more bases. In some of these embodiments, the multimeric nucleic acid TLR9 ligand includes further $(X_a)_n$, where each $X_a$ is a monomeric TLR9 ligand as defined above, n=0, 1, 2, 3, 4, 5, 6, 7, 8, 9, 10, from 10 to about 15, from 15 to about 20, from 20 to about 25, from 25 to about 30, from 30 to about 40, from 40 to about 50, from 50 to about 60, from 60 to about 70, from 70 to about 80, from 80 to about 90, or from 90 to about 100, and where $X_a=X_3$, $X_3X4$, $X_3X_4X_5$, $X_3X_4X_5X_6$, etc., and where each X of $X_3$, $X_3X_4$, $X_3X_4X_5$, $X_3X_4X_5X_6$, etc. has the same or different nucleotide sequence from $X_1$ and/or $X_2$.

As noted above, in some embodiments, a subject multimeric TLR9 ligand comprises a TLR9 ligand separated from an adjacent TLR9 ligand by a spacer. In some embodiments, a spacer is a non-TLR9 ligand nucleic acid. In other embodiments, a spacer is a non-nucleic acid moiety. Suitable spacers include those described in U.S. Patent Publication No. 20030225016. A TLR9 ligand is multimerized using any known method.

In some embodiments, a nucleic acid TLR9 ligand comprises a guanine-rich 3' tail. The presence of a guanine-rich 3' tail promotes multimerization of a nucleic acid TLR9 ligand. A guanine-rich 3' tail can comprise from about 4 guanine residues to about 50 guanine residues, e.g., from about 4 guanine residues to about 6 guanine residues, from about 6 guanine residues to about 10 guanine residues, from about 10 guanine residues to about 15 guanine residues, from about 15 guanine residues to about 20 guanine residues, from about 20 guanine residues to about 25 guanine residues, from about 25 guanine residues to about 50 guanine residues, from about 50 guanine residues to about 75 guanine residues, or from about 75 guanine residues to about 100 guanine residues, in a guanine-rich tail having a length of from about 4 nucleotides to about 200 nucleotides, e.g., from about 4 nucleotides to about 10 nucleotides, from about 10 nucleotides to about 20 nucleotides, from about 20 nucleotides to about 50 nucleotides, from about 50 nucleotides to about 100 nucleotides, or from about 100 nucleotides to about 200 nucleotides. Typically, the proportion of guanine residues in a guanine-rich tail ranges from about 30% to about 100%, e.g., from about 30% to about 40%, from about 40% to about 50%, from about 50% to about 60%, from about 60% to about 70%, from about 70% to about 80%, from about 80% to about 90%, or from about 90% to about 100%.

In some embodiments, a TLR9 ligand comprises the sequence 5'-$X_n$-CG-$X_m$-(A)-3', where A is a guanine-rich tail as described above, where X is any nucleotide, and n and m are independently an integer from 0 to 200. In some embodiments, a TLR9 ligand comprises the sequence 5'-$X_n$-$(TCG)_p$-$X_m$-(A)-3', where A is a guanine-rich tail as described above, where X is any nucleotide, n and m are independently an integer from 0 to 200, and p is 1, 2, 3, 4, 5, 6, 7, 8, 9, or 10.

TLR9 Ligand Modifications

A TLR9 ligand suitable for use in a subject composition can be modified in a variety of ways. For example, a TLR9 ligand can comprise backbone phosphate group modifications (e.g., methylphosphonate, phosphorothioate, phosphoroamidate and phosphorodithioate internucleotide linkages), which modifications can, for example, enhance their stability in vivo, making them particularly useful in therapeutic applications. A particularly useful phosphate group modification is the conversion to the phosphorothioate or phosphorodithioate forms of a nucleic acid TLR9 ligand. Phosphorothioates and phosphorodithioates are more resistant to degradation in vivo than their unmodified oligonucleotide counterparts, increasing the half-lives of the TLR9 ligands and making them more available to the subject being treated.

Other modified TLR9 ligands encompassed by the present invention include TLR9 ligands having modifications at the 5' end, the 3' end, or both the 5' and 3' ends. For example, the 5' and/or 3' end can be covalently or non-covalently associated with a molecule (either nucleic acid, non-nucleic acid, or both) to, for example, increase the bio-availability of the TLR9 ligand, increase the efficiency of uptake where desirable, facilitate delivery to cells of interest, and the like. Exemplary molecules for conjugation to a TLR9 ligand include, but are not necessarily limited to, cholesterol, phospholipids, fatty acids, sterols, oligosaccharides, polypeptides (e.g., immunoglobulins), peptides, antigens (e.g., peptides, small molecules, etc.), linear or circular nucleic acid molecules (e.g., a plasmid), insoluble supports, therapeutic polypeptides, and the like. Therapeutic polypeptides that are suitable for attachment to a TLR9 agonist include, but are not limited to, a dendritic cell growth factor (e.g., GM-CSF); a cytokine; an interferon (e.g., an IFN-α, an IFN-β, etc.); a TNF-α antagonist; and the like.

A TLR9 ligand is in some embodiments linked (e.g., conjugated, covalently linked, non-covalently associated with, or adsorbed onto) an insoluble support. An exemplary, non-limiting example of an insoluble support is cationic poly(D, L-lactide-co-glycolide).

Additional TLR9 ligand conjugates, and methods for making same, are known in the art and described in, for example, WO 98/16427 and WO 98/55495. Thus, the term TLR9 ligand" includes conjugates comprising a nucleic acid TLR9 ligand.

A polypeptide, e.g., a therapeutic polypeptide, may be conjugated directly or indirectly, e.g., via a linker molecule, to a TLR9 ligand. A wide variety of linker molecules are known in the art and can be used in the conjugates. The linkage from the peptide to the oligonucleotide may be through a peptide reactive side chain, or the N- or C-terminus of the peptide. Linkage from the oligonucleotide to the peptide may be at either the 3' or 5' terminus, or internal. A linker may be an organic, inorganic, or semi-organic molecule, and may be a polymer of an organic molecule, an inorganic molecule, or a co-polymer comprising both inorganic and organic molecules.

If present, the linker molecules are generally of sufficient length to permit oligonucleotides and/or polynucleotides and a linked polypeptide to allow some flexible movement between the oligonucleotide and the polypeptide. The linker molecules are generally about 6-50 atoms long. The linker molecules may also be, for example, aryl acetylene, ethylene glycol oligomers containing 2-10 monomer units, diamines, diacids, amino acids, or combinations thereof. Other linker molecules which can bind to oligonucleotides may be used in light of this disclosure.

Peptides may be synthesized chemically or enzymatically, may be produced recombinantly, may be isolated from a natural source, or a combination of the foregoing.

Peptides may be isolated from natural sources using standard methods of protein purification known in the art, including, but not limited to, HPLC, exclusion chromatography, gel electrophoresis, affinity chromatography, fast protein liquid chromatography, or other purification technique. One may employ solid phase peptide synthesis techniques, where such techniques are known to those of skill in the art. See Jones, *The Chemical Synthesis of Peptides* (Clarendon Press, Oxford)(1994). Generally, in such methods a peptide is produced through the sequential additional of activated monomeric units to a solid phase bound growing peptide chain. Well-established recombinant DNA techniques can be employed for production of peptides.

Combination Therapies

In some embodiments, a subject method of treating gastrointestinal inflammation comprises administering two or more agents that induce the synthesis of a Type I interferon and/or increases a level of a Type I interferon in an individual and/or activates a Type I interferon signaling pathway. In some embodiments, a subject method of treating gastrointestinal inflammation comprises administering an agent that induces the synthesis of a Type I interferon and/or increases a level of a Type I interferon in an individual and/or activates a Type I interferon signaling pathway; and at least a second therapeutic agent for the treatment of gastrointestinal inflammation.

Additional therapeutic agents that are suitable for use in a subject combination therapy include, but are not limited to, immunosuppressive agents; aminosalicylates; immunomodulators; Type I interferon receptor agonists; corticosteroids; antibiotics; non-steroidal anti-inflammatory drugs (NSAIDs); anti-malarial agents; antibiotics; mercaptopurine; anti-diarrheal drugs; and TNF-a antagonists.

Aminosalicylates

Suitable aminosalicylates include, but are not limited to, 5-aminosalicylate and its prodrug, sulfasalazine; olsalazine; mesalamine; and the like.

Antimalarial agents

Suitable antimalarial agents include, but are not limited to, pamaquine, primaquine, pentaquine, isopentaquine, quinacrine salts; 7-chloro-4-aminoquinolines, such as the chloroquines, hydroxychloroquines, sontoquine, amodiaquine; cinchono alkaloids and 4-quinoline methanols; and the like. Examples of suitable anti-malarial agents include Plaquenil (hydroxychloroquine), Aralen (chloroquine); Atabrine (quinacrine); 8-aminoquinolines; 9-aminocridines; the 7-chloro-4-aminoquinolines; rubane, quinine, quinidine, cinchoidine, epiquinine, epiquinidine, cinchonine, and the like.

Immunosuppressants

Suitable immunosuppressive agents include, but are not limited to, Imuran (azathioprine), Cytoxan (cyclophosphamide), cyclosporine (Sandimmune®), rapamycin (sirolimus; Rapamune), tacrolimus (FK506), mycophenolate mofetil (CellCept®), 6-mercaptopurine, 15-deoxyspergualin, mizoribine, chlorambucil (Leukeran®), and the like.

Corticosteroids

Suitable corticosteroids include, but are not limited to, prednisolone, dexamethasone (Decadron™), methylprednisolone (Medrol®; SoluMedrol®), corticotropin (Acthar®), cortisone, hydrocortisone (Hydrocortonet), prednisone (Deltasone®; Orasone®), triamcinolone, and the like.

Anti-Diarrheal Drugs

Suitable anti-diarrheal drugs include, but are not limited to, codeine, diphenoxylate-atropine combination, loperamide, Rolgamidine, Diphenoxylate hydrochloride, Metronidazole (Flagyl), Methylprednisolone (Medrol), Sulfasalazine (Azulfidine), and the like.

NSAIDs

Suitable NSAIDs include, but are not limited to, acetylsalicylic acid, ibuprofen, diclofenac (Voltaren™), etodolac (Lodine™), fenoprofen (Nalfon™), indomethacin (Indocin™), ketoralac (Toradol™), oxaprozin (Daypro™), nabumentone (Relafen™), sulindac (Clinoml™), tolmentin (Tolectin™), naproxen (Aleve™, Naprosyn™), ketoprofen (Actron™), cyclooxygenase (cox) inhibitors, selective cyclooxygenase-2 (cox-2) inhibitors (e.g., celecoxib (Celebrex™), rofecoxib (Vioxx™), valdecoxib (Bextra™), and the like.

TNF-α Antaonists

Also suitable for use in a subject combination therapy are tumor necrosis factor-α (TNF-α) antagonists (also referred to herein as "TNF antagonists"). Suitable TNF antagonists include, but are not limited to, antibodies to TNF-α, soluble TNF receptor (TNFR), and the like.

The terms "TNF receptor polypeptide" and "TNFR polypeptide" refer to polypeptides derived from TNFR (from any species) which are capable of binding TNF. Two distinct cell-surface TNFRs have been described: Type II TNFR (or p75 TNFR or TNFRII) and Type I TNFR (or p55 TNFR or TNFRI). The mature full-length human p75 TNFR is a glycoprotein having a molecular weight of about 75-80 kilodaltons (kD). The mature full-length human p55 TNFR is a glycoprotein having a molecular weight of about 55-60 kD. Exemplary TNFR polypeptides are derived from TNFR Type I and/or TNFR type II. Soluble TNFR includes p75 TNFR polypeptide; fusions of p75 TNFR with heterologous fusion partners, e.g., the Fc portion of an immunoglobulin.

TNFR polypeptide may be an intact TNFR or a suitable fragment of TNFR. U.S. Pat. No. 5,605,690 provides examples of TNFR polypeptides, including soluble TNFR polypeptides, appropriate for use in the present invention. In many embodiments, the TNFR polypeptide comprises an extracellular domain of TNFR. In some embodiments, the TNFR polypeptide is a fusion polypeptide comprising an extracellular domain of TNFR linked to a constant domain of an immunoglobulin molecule. In other embodiments, the TNFR polypeptide is a fusion polypeptide comprising an extracellular domain of the p75 TNFR linked to a constant domain of an IgG1 molecule. In some embodiments, when administration to humans is contemplated, an Ig used for fusion proteins is human, e.g., human IgG1.

Monovalent and multivalent forms of TNFR polypeptides may be used in the present invention. Multivalent forms of TNFR polypeptides possess more than one TNF binding site. In some embodiments, the TNFR is a bivalent, or dimeric, form of TNFR. For example, as described in U.S. Pat. No. 5,605,690 and in Mohler et al., 1993, J. Immunol., 151:1548-1561, a chimeric antibody polypeptide with TNFR extracellular domains substituted for the variable domains of either or both of the immunoglobulin heavy or light chains would provide a TNFR polypeptide for use in the present invention. Generally, when such a chimeric TNFR:antibody polypeptide is produced by cells, it forms a bivalent molecule through disulfide linkages between the immunoglobulin domains. Such a chimeric TNFR:antibody polypeptide is referred to as TNFR:Fc.

One non-limiting example of a suitable TNF antagonist is the soluble TNFR ENBREL® etanercept. ENBREL® is a dimeric fusion protein consisting of the extracellular ligand-binding portion of the human 75 kilodalton (p75) TNFR linked to the Fc portion of human IgG1. The Fc component of ENBREL® contains the CH2 domain, the CH3 domain and hinge region, but not the CHI domain of IgG1. ENBREL® is produced in a Chinese hamster ovary (CHO) mammalian cell expression system. It consists of 934 amino acids and has an apparent molecular weight of approximately 150 kilodaltons. Smith et al. (1990) *Science* 248:1019-1023; Mohler et al. (1993) *J. Immunol.* 151:1548-1561; U.S. Pat. Nos. 5,395, 760; and 5,605,690.

Also suitable for use are monoclonal antibodies that bind TNF-α. Monoclonal antibodies include "humanized" mouse monoclonal antibodies; chimeric antibodies; monoclonal antibodies that are at least about 80%, at least about 90%, at least about 95%, or 100% human in amino acid sequence; and the like. See, e.g., WO 90/10077; WO 90/04036; and WO 92/02190. Suitable monoclonal antibodies include antibody fragments, such as Fv, F(ab')$_2$ and Fab; synthetic antibodies; artificial antibodies; phage display antibodies; and the like.

Examples of suitable monoclonal antibodies include infliximab (REMICADE®, Centocor); and adalimumab (HUMIRA®, Abbott) REMICADE® is a chimeric monoclonal anti-TNF-α antibody that includes about 25% mouse amino acid sequence and about 75% human amino acid sequence. REMICADE® comprises a variable region of a mouse monoclonal anti-TNF-α antibody fused to the constant region of a human IgG1. Elliott et al. (1993) *Arthritis Rheum.* 36:1681-1690; Elliott et al. (1994) *Lancet* 344:1105-1110; Baert et al. (1999) *Gastroenterology* 116:22-28. HUMIRA® is a human, full-length IgG1 monoclonal antibody that was identified using phage display technology. Piascik (2003) *J. Am. Pharm. Assoc.* 43:327-328.

Antibiotics

Suitable antibiotics include, but are not limited to, metronidazole, ampicillin, and ciprofloxacin.

Immunomodulators

Suitable immunomodulators include, but are not limited to, 6-mercaptopurine, and the like.

Type I Interferon Receptor Agonists

As used herein, the term "a Type I interferon receptor agonist" refers to any naturally occurring or non-naturally occurring ligand of human Type I interferon receptor, which binds to and causes signal transduction via the receptor. Type I interferon receptor agonists include interferons, including naturally-occurring interferons, modified interferons, synthetic interferons, pegylated interferons, fusion proteins comprising an interferon and a heterologous protein, shuffled interferons; antibody specific for an interferon receptor; non-peptide chemical agonists; and the like.

Type I interferon receptor agonists include interferon-alpha (IFN-α) and interferon-beta (IFN-β).

In some embodiments, a subject combination therapy comprises administering a Type I activating agent; and an IFN-α. Any known IFN-α can be used in the instant invention. The term "interferon-alpha" as used herein refers to a family of related polypeptides that inhibit viral replication and cellular proliferation and modulate immune response. The term "IFN-α" includes naturally occurring IFN-α; synthetic IFN-α; derivatized IFN-α (e.g., PEGylated IFN-α, glycosylated IFN-α, and the like); and analogs of naturally occurring or synthetic IFN-α; essentially any IFN-α that has antiviral properties, as described for naturally occurring IFN-α.

Suitable IFN-α include, but are not limited to, naturally-occurring IFN-α (including, but not limited to, naturally occurring IFN-α2a, IFN-α2b); recombinant interferon alpha-2b such as Intron-A interferon available from Schering Corporation, Kenilworth, N.J.; recombinant interferon alpha-2a such as Roferon interferon available from Hoffmann-La Roche, Nutley, N.J.; recombinant interferon alpha-2C such as Berofor alpha 2 interferon available from Boehringer Ingelheim Pharmaceutical, Inc., Ridgefield, Conn.; interferon alpha-n1, a purified blend of natural alpha interferons such as Sumiferon available from Sumitomo, Japan or as Wellferon interferon alpha-n1 (INS) available from the Glaxo-Wellcome Ltd., London, Great Britain; and interferon alpha-n3 a mixture of natural alpha interferons made by Interferon Sciences and available from the Purdue Frederick Co., Norwalk, Conn., under the Alferon Tradename.

The term "IFN-α" also encompasses consensus IFN-α. Consensus IFN-α (also referred to as "CIFN" and "IFN-con" and "consensus interferon") encompasses but is not limited to the amino acid sequences designated IFN-con$_1$, IFN-con$_2$ and IFN-con$_3$ which are disclosed in U.S. Pat. Nos. 4,695,623 and 4,897,471; and consensus interferon as defined by determination of a consensus sequence of naturally occurring interferon alphas (e.g., Infergen®, InterMune, Inc., Brisbane, Calif.). IFN-con$_1$, is the consensus interferon agent in the Infergen® alfacon-1 product. The Infergen® consensus interferon product is referred to herein by its brand name (Infergen®) or by its generic name (interferon alfacon-1). DNA sequences encoding IFN-con may be synthesized as described in the aforementioned patents or other standard methods.

Also suitable for use in the present invention are fusion polypeptides comprising an IFN-α and a heterologous polypeptide. Suitable IFN-α fusion polypeptides include, but are not limited to, Albuferon-alpha™ (a fusion product of human albumin and IFN-α; Human Genome Sciences; see, e.g., Osborn et al. (2002) *J. Pharmacol. Exp. Therap.* 303: 540-548). Also suitable for use in the present invention are gene-shuffled forms of IFN-α. See., e.g., Masci et al. (2003) *Curr. Oncol. Rep.* 5:108-113.

The term "IFN-α" also encompasses derivatives of IFN-α that are derivatized (e.g., are chemically modified) to alter certain properties such as serum half-life. As such, the term "IFN-α" includes glycosylated IFN-α; IFN-α derivatized with polyethylene glycol ("PEGylated IFN-α"); and the like. PEGylated IFN-α, and methods for making same, is discussed in, e.g., U.S. Pat. Nos. 5,382,657; 5,981,709; and 5,951,974. PEGylated IFN-α encompasses conjugates of PEG and any of the above-described IFN-α molecules, including, but not limited to, PEG conjugated to interferon alpha-2a (Roferon, Hoffman La-Roche, Nutley, N.J.), interferon alpha 2b (Intron, Schering-Plough, Madison, N.J.), interferon alpha-2c (Berofor Alpha, Boehringer Ingelheim, Ingelheim, Germany); and consensus interferon as defined by determination of a consensus sequence of naturally occurring interferon alphas (Infergen®, InterMune, Inc., Brisbane, Calif.). Examples of suitable PEGylated IFN-α include PEGASYS® PEGylated IFN-α2a; and PEG-INTRON® PEGylated IFN-α2b.

Also suitable for use herein are IFN-α hybrids, e.g., as described in U.S. Pat. No. 6,685,933. Also suitable for use herein are IFN-α mixtures, e.g., as described in U.S. Pat. No. 6,350,589.

The term interferon-beta ("IFN-β") includes IFN-β polypeptides that are naturally occurring; non-naturally-occurring IFN-β polypeptides; and analogs and variants of naturally occurring or non-naturally occurring IFN-β that retain antiviral activity of a parent naturally-occurring or non-naturally occurring IFN-β.

Any of a variety of beta interferons can be used in a subject method. Suitable beta interferons include, but are not limited to, naturally-occurring IFN-β; IFN-β1a, e.g., Avonex® (Biogen, Inc.), and Rebif® (Serono, SA); IFN-β1b (Betaseron®; Berlex); and the like.

The IFN-⊕ formulation may comprise an N-blocked species, wherein the N-terminal amino acid is acylated with an acyl group, such as a formyl group, an acetyl group, a malonyl group, and the like. Also suitable for use is a consensus IFN-β.

IFN-β polypeptides can be produced by any known method. DNA sequences encoding IFN-β may be synthesized using standard methods. In many embodiments, IFN-β polypeptides are the products of expression of manufactured DNA sequences transformed or transfected into bacterial hosts, e.g., *E. coli*, or in eukaryotic host cells (e.g., yeast; mammalian cells, such as CHO cells; and the like). In these embodiments, the IFN-β is "recombinant IFN-β." Where the host cell is a bacterial host cell, the IFN-β is modified to comprise an N-terminal methionine.

It is to be understood that IFN-β as described herein may comprise one or more modified amino acid residues, e.g., glycosylations, chemical modifications, and the like.

Dosages, Formulations, and Routes of Administration

Active agents (e.g., a Type I interferon activating agent, a second therapeutic agent, etc.) are generally administered to individuals in formulations admixed with a pharmaceutically acceptable excipient(s). A wide variety of pharmaceutically acceptable excipients is known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H.C. Ansel et al., eds., 7$^{th}$ ed., Lippincott, Williams, & Wilkins; and Handbook of Pharmaceutical Excipients (2000) A. H. Kibbe et al., eds., 3$^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In the subject methods, the active agents may be administered to the host using any convenient means capable of resulting in the desired therapeutic effect. Thus, the active agents can be incorporated into a variety of formulations for therapeutic administration. More particularly, the active agents can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

As such, administration of the agents can be achieved in various ways. Conventional and pharmaceutically acceptable routes of administration for treatment of gastrointestinal inflammation (e.g., chronic gastrointestinal inflammation such as that of IBD), include, but are not necessarily limited to, intramuscular, subcutaneous, intraderrnal, transdermal, intravenous, rectal (e.g., enema, suppository), oral, intragastric, intranasal and other routes of effective inhalation routes, and other parenteral routes of administration. In general, gastrointestinal routes of administration are of particular interest in the present invention for treatment of gastrointestinal inflammation including, but not necessarily limited to oral (including ingestion), intranasal, intragastric, and rectal administration. Routes of administration may be combined, if desired, or adjusted depending upon the therapeutic agent. The active agent (e.g., a Type I interferon activating agent, a second therapeutic agent, etc.) can be administered in a single dose or in multiple doses, and may encompass administration of additional doses, to elicit and/or maintain the desired effect.

An active agent can be administered to a subject using any available conventional methods and routes suitable for delivery of conventional drugs, including systemic or localized routes. Methods and localized routes that further facilitate activity of the active agent, particularly at or near a site of inflammation is of interest in the invention, and may be preferred over systemic routes of administration, both for the immediacy of therapeutic effect and reduction of the incident of in vivo degradation of the administered active agent. In general, routes of administration contemplated by the invention include, but are not necessarily limited to, gastroenteral, enteral, or parenteral routes. Gastroenteral routes of administration include, but are not necessarily limited to, oral and rectal (e.g., using a suppository) delivery.

Subcutaneous administration of an active agent is accomplished using standard methods and devices, e.g., needle and syringe, a subcutaneous injection port delivery system, and the like. See, e.g., U.S. Pat. Nos. 3,547,119; 4,755,173; 4,531,937; 4,311,137; and 6,017,328. A combination of a subcutaneous injection port and a device for administration of an interferon receptor agonist to a patient through the port is referred to herein as "a subcutaneous injection port delivery system." In some embodiments, subcutaneous administration is achieved by a combination of devices, e.g., bolus delivery by needle and syringe, followed by delivery using a continuous delivery system.

In pharmaceutical dosage forms, the. agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Furthermore, the agents can be made into suppositories by mixing with a variety of bases such as emulsifying bases or water-soluble bases. An active agent can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more active agents. Similarly, unit dosage forms for injection or intravenous administration may comprise the agent(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of an active agent calculated in an amount sufficient to produce the desired effect in association with a pharmaceutically acceptable diluent, carrier or vehicle. The specifications for the dosage form depend on the particular compound employed and the effect to be achieved, and the pharmacodynamics associated with each compound in the host.

The dose of an active agent administrated to a subject, in the context of the present invention, should be sufficient to effect a beneficial therapeutic response in the subject over time, or to alleviate symptoms. Thus, an active agent is administered to a patient in an amount sufficient to alleviate, reduce, cure or at least partially arrest symptoms and/or complications from the disease. An amount adequate to accomplish this is defined as a "therapeutically effective dose."

In general, a Type I interferon activating agent is administered to an individual in an amount of from about 5 μg to about 1200 mg, e.g., from about 5 μg to about 10 μg, from about 10 μg to about 50 μg, from about 50 μg to about 100 μg, from about 100 μg to about 500 μg, from about 500 μg to about 1 mg, from about 1 mg to about 10 mg, from about 10 mg to about 50 mg, from about 50 mg to about 100 mg, from about 100 mg to about 250 mg, from about 250 mg to about 500 mg, from about 500 mg to about 1000 mg, or from about 1000 mg to about 1200 mg.

In many embodiments, a Type I interferon activating agent is administered for a period of about 1 day to about 7 days, or about 1 week to about 2 weeks, or about 2 weeks to about 3 weeks, or about 3 weeks to about 4 weeks, or about 1 month to about 2 months, or about 3 months to about 4 months, or about 4 months to about 6 months, or about 6 months to about 8 months, or about 8 months to about 12 months, or at least one year, and may be administered over longer periods of time. A Type I interferon activating agent can be administered tid, bid, qd, qod, biw, tiw, qw, qow, three times per month, once monthly, substantially continuously, or continuously.

In many embodiments, multiple doses of a Type I interferon activating agent are administered. For example, a Type I interferon activating agent is administered once per month, twice per month, three times per month, every other week (qow), once per week (qw), twice per week (biw), three times per week (tiw), four times per week, five times per week, six times per week, every other day (qod), daily (qd), twice a day (bid), or three times a day (tid), substantially continuously, or continuously, over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

In some embodiments, e.g., where the gastrointestinal inflammatory disorder is characterized by intermittent flare-ups or other episode or appearance of a symptom of a gastrointestinal inflammatory disorder (e.g., diarrhea, rectal bleeding, weight loss, abdominal pain, etc.), a Type I interferon activating agent is administered immediately following a flare-up or other episode or appearance of symptoms, e.g., within 2 hours after the appearance of the symptom, e.g., from about 1 minute to about 2 hours after appearance of the symptom. In other embodiments, a Type I interferon activating agent is administered as needed to reduce the frequency and/or severity of a symptom associated with a gastrointestinal inflammatory disorder, e.g., a Type I interferon activating agent is administered within about 1 minute to about 30 minutes following an episode or appearance of the symptom. In other embodiments, a Type I interferon activating agent is administered continuously.

In some embodiments, the instant invention provides a method for treating a gastrointestinal inflammatory disorder in an individual by administering to an individual in need thereof an effective amount of a Type I interferon activating agent, the method comprising administering a dosage of a nucleoside analog containing an amount of from about 400 mg to about 1200 mg, from about 600 mg to about 1000 mg, or from about 700 to about 900 mg per day orally for the desired treatment duration.

In some embodiments, the instant invention provides a method for treating a gastrointestinal inflammatory disorder in an individual by administering to an individual in need thereof an effective amount of a Type I interferon activating agent, the method comprising administering a dosage of ribavirin containing an amount of from about 400 mg to about 1200 mg, from about 600 mg to about 1000 mg, or from about 700 to about 900 mg per day orally for the desired treatment duration. In some embodiments, ribavirin is administered in an amount of 800 mg qd, orally. In other embodiments, ribavirin is administered in an amount of 1000 mg qd, orally. In other embodiments, ribavirin is administered in an amount of 1200 mg qd, orally.

In some embodiments, the instant invention provides a method for treating a gastrointestinal inflammatory disorder in an individual by administering to an individual in need thereof an effective amount of a Type I interferon activating agent, the method comprising administering a dosage of levovirin containing an amount of from about 400 mg to about 1200 mg, from about 600 mg to about 1000 mg, or from about 700 to about 900 mg per day orally for the desired treatment duration. In some embodiments, levovirin is administered in an amount of 800 mg qd, orally. In other embodiments, levovirin is administered in an amount of 1000 mg qd, orally. In other embodiments, levovirin is administered in an amount of 1200 mg qd, orally.

In some embodiments, the instant invention provides a method for treating a gastrointestinal inflammatory disorder in an individual by administering to an individual in need thereof an effective amount of a Type I interferon activating agent, the method comprising administering a dosage of a 2-substituted 8-hydroxyadenine compound containing an amount of from about 100 mg to about 1200 mg, from about 600 mg to about 1000 mg, or from about 700 to about 900 mg per day orally for the desired treatment duration.

In some embodiments, the instant invention provides a method for treating a gastrointestinal inflammatory disorder in an individual by administering to an individual in need thereof an effective amount of a Type I interferon activating agent, the method comprising administering a dosage of a dendritic cell growth factor containing an amount of from about 100 µg to about 250 µg subcutaneously, twice weekly or three times weekly, for the desired treatment duration.

In some embodiments, the instant invention provides a method for treating a gastrointestinal inflammatory disorder in an individual by administering to an individual in need thereof an effective amount of a Type I interferon activating agent, the method comprising administering a dosage of GM-CSF (e.g., sargramostin) containing an amount of from about 100 µg to about 250 µg subcutaneously, twice weekly or three times weekly, for the desired treatment duration.

In some embodiments, the instant invention provides a method for treating a gastrointestinal inflammatory disorder in an individual by administering to an individual in need thereof an effective amount of a Type I interferon activating agent, the method comprising administering a dosage of an IMPDH inhibitor containing an amount of from about 100 $mg/mr^2$ to about 1500 $mg/m^2$, e.g., from about 100 $mg/m^2$ to about 500 $mg/m^2$, from about 500 $mg/m^2$ to about 800 $mg/m^2$, from about 800 $mg/m^2$ to about 1000 $mg/m^2$, or from about 1000 $mg/m^2$ to about 1500 $mg/m^2$, for the desired treatment duration.

In some embodiments, the instant invention provides a method for treating a gastrointestinal inflammatory disorder in an individual by administering to an individual in need thereof an effective amount of a Type I interferon activating agent, the method comprising administering a dosage of tiazofurin containing an amount of from about 100 $mg/m^2$ to about 1500 $mg/m^2$, e.g., from about 100 $mg/m^2$ to about 500 $mg/m^2$, from about 500 $mg/m^2$ to about 800 $mg/m^2$, from about 800 $mg/m^2$ to about 1000 $mg/m^2$, or from about 1000 $mg/m^2$ to about 1500 $mg/m^2$, for the desired treatment duration. In some embodiments, the method involves administering tiazofurin in an amount of from about 500 $mg/m^2$ to about 1000 $mg/m^2$.

In some embodiments, the instant invention provides a method for treating a gastrointestinal inflammatory disorder in an individual by administering to an individual in need thereof an effective amount of a Type I interferon activating agent, the method comprising administering a dosage of mizoribine in an amount of from about 100 mg to about 500 mg per day, e.g., from about 100 mg to about 250 mg, or from about 250 mg to about 500 mg daily, for the desired treatment duration.

In some embodiments, the instant invention provides a method for treating a gastrointestinal inflammatory disorder in an individual by administering to an individual in need thereof an effective amount of a Type I interferon activating agent, the method comprising administering a dosage of CellCept® (mycophenolate mofetil) containing an amount of 1 g orally for the desired treatment duration.

In some embodiments, the instant invention provides a method for treating a gastrointestinal inflammatory disorder in an individual by administering to an individual in need thereof an effective amount of a Type I interferon activating agent, the method comprising administering a dosage of a TLR3 agonist containing an amount of from about 1 µg to about 1000 mg qd, qod, tiw, bid, or weekly, orally, intramuscularly, subcutaneously, or intravenously, for the desired treatment duration.

In some embodiments, the instant invention provides a method for treating a gastrointestinal inflammatory disorder in an individual by administering to an individual in need thereof an effective amount of a Type I interferon activating agent, the method comprising administering a dosage of a TLR4 agonist containing an amount of from about 1 µg to about 1000 mg qd, qod, tiw, bid, or weekly, orally, intramuscularly, subcutaneously, or intravenously, for the desired treatment duration.

In some embodiments, the instant invention provides a method for treating a gastrointestinal inflammatory disorder in an individual by administering to an individual in need thereof an effective amount of a Type I interferon activating agent, the method comprising administering a dosage of a TLR7 agonist containing an amount of from about 1 µg to about 1000 mg qd, qod, tiw, bid, or weekly, orally, intramuscularly, subcutaneously, or intravenously, for the desired treatment duration.

In some embodiments, the instant invention provides a method for treating a gastrointestinal inflammatory disorder in an individual by administering to an individual in need thereof an effective amount of a Type I interferon activating agent, the method comprising administering a dosage of a TLR8 agonist containing an amount of from about 1 µg to about 1000 mg qd, qod, tiw, bid, or weekly, orally, intramuscularly, subcutaneously, or intravenously, for the desired treatment duration.

In some embodiments, the instant invention provides a method for treating a gastrointestinal inflammatory disorder in an individual by administering to an individual in need thereof an effective amount of a Type I interferon activating agent, the method comprising administering a dosage of a TLR9 agonist containing an amount of from about 1 µg to about 1000 mg qd, qod, tiw, bid, or weekly, orally, intramuscularly, subcutaneously, or intravenously, for the desired treatment duration.

Combination Therapy with Two or More Type I Interferon Activating Agents

The instant invention provides combination therapy methods for treating a gastrointestinal inflammatory disorder, generally involving administering combined effective amounts of two or more Type I interferon activating agents for the desired treatment duration. The following examples are provided for the purposes of illustration only, and are not meant to be limiting.

In some embodiments, the instant invention provides a method for treating a gastrointestinal inflammatory disorder in an individual by administering to an individual in need thereof an effective amounts of two or more Type I interferon activating agents, the method comprising administering: i) a dosage of a TLR7 agonist containing an amount of from about 1 μg to about 1000 mg qd, qod, tiw, bid, or weekly, orally, intramuscularly, subcutaneously, or intravenously; and ii) a dosage of a TLR8 agonist containing an amount of from about 1 μg to about 1000 mg qd, qod, tiw, bid, or weekly, orally, intramuscularly, subcutaneously, or intravenously, for the desired treatment duration.

In some embodiments, the instant invention provides a method for treating a gastrointestinal inflammatory disorder in an individual by administering to an individual in need thereof an effective amounts of two or more Type I interferon activating agents, the method comprising administering: i) a dosage of a selective TLR7 agonist containing an amount of from about 1 μg to about 1000 mg qd, qod, tiw, bid, or weekly, orally, intramuscularly, subcutaneously, or intravenously; and ii) a dosage of a selective TLR8 agonist containing an amount of from about 1 μg to about 1000 mg qd, qod, tiw, bid, or weekly, orally, intramuscularly, subcutaneously, or intravenously, for the desired treatment duration.

In some embodiments, the instant invention provides a method for treating a gastrointestinal inflammatory disorder in an individual by administering to an individual in need thereof an effective amounts of two or more Type I interferon activating agents, the method comprising administering: i) a dosage of a TLR7 agonist containing an amount of from about 1 μg to about 1000 mg qd, qod, tiw, bid, or weekly, orally, intramuscularly, subcutaneously, or intravenously; and ii) a dosage of a TLR9 agonist containing an amount of from about 1 μg to about 1000 mg qd, qod, tiw, bid, or weekly, orally, intramuscularly, subcutaneously, or intravenously, for the desired treatment duration.

In some embodiments, the instant invention provides a method for treating a gastrointestinal inflammatory disorder in an individual by administering to an individual in need thereof an effective amounts of two or more Type I interferon activating agents, the method comprising administering: i) a dosage of a TLR8 agonist containing an amount of from about 1 μg to about 1000 mg qd, qod, tiw, bid, or weekly, orally, intramuscularly, subcutaneously, or intravenously; and ii) a dosage of a TLR9 agonist containing an amount of from about 1 μg to about 1000 mg qd, qod, tiw, bid, or weekly, orally, intramuscularly, subcutaneously, or intravenously, for the desired treatment duration.

In some embodiments, the instant invention provides a method for treating a gastrointestinal inflammatory disorder in an individual by administering to an individual in need thereof an effective amounts of two or more Type I interferon activating agents, the method comprising administering: i) a dosage of a TLR7 agonist containing an amount of from about 1 μg to about 1000 mg qd, qod, tiw, bid, or weekly, orally, intramuscularly, subcutaneously, or intravenously; and ii) a dosage of a nucleoside analog containing an amount of from about 400 mg to about 1200 mg, from about 600 mg to about 1000 mg, or from about 700 to about 900 mg per day orally for the desired treatment duration.

In some embodiments, the instant invention provides a method for treating a gastrointestinal inflammatory disorder in an individual by administering to an individual in need thereof an effective amounts of two or more Type I interferon activating agents, the method comprising administering: i) a dosage of a TLR8 agonist containing an amount of from about 1 μg to about 1000 mg qd, qod, tiw, bid, or weekly, orally, intramuscularly, subcutaneously, or intravenously; and ii) a dosage of a nucleoside analog containing an amount of from about 400 mg to about 1200 mg, from about 600 mg to about 1000 mg, or from about 700 to about 900 mg per day orally for the desired treatment duration.

In some embodiments, the instant invention provides a method for treating a gastrointestinal inflammatory disorder in an individual by administering to an individual in need thereof an effective amounts of two or more Type I interferon activating agents, the method comprising administering: i) a dosage of a TLR9 agonist containing an amount of from about 1 μg to about 1000 mg qd, qod, tiw, bid, or weekly, orally, intramuscularly, subcutaneously, or intravenously; and ii) a dosage of a nucleoside analog containing an amount of from about 400 mg to about 1200 mg, from about 600 mg to about 1000 mg, or from about 700 to about 900 mg per day orally for the desired treatment duration.

In some embodiments, the instant invention provides a method for treating a gastrointestinal inflammatory disorder in an individual by administering to an individual in need thereof an effective amounts of two or more Type I interferon activating agents, the method comprising administering: i) a dosage of a TLR7 agonist, a TLR8 agonist, or a TLR9 agonist containing an amount of from about 1 μg to about 1000 mg qd, qod, tiw, bid, or weekly, orally, intramuscularly, subcutaneously, or intravenously; and ii) a dosage of ribavirin containing an amount of from about 400 mg to about 1200 mg, from about 600 mg to about 1000 mg, or from about 700 to about 900 mg per day orally for the desired treatment duration.

In some embodiments, the instant invention provides a method for treating a gastrointestinal inflammatory disorder in an individual by administering to an individual in need thereof an effective amounts of two or more Type I interferon activating agents, the method comprising administering: i) a dosage of a TLR7 agonist, a TLR8 agonist, or a TLR9 agonist containing an amount of from about 1 μg to about 1000 mg qd, qod, tiw, bid, or weekly, orally, intramuscularly, subcutaneously, or intravenously; and ii) a dosage of a 2-substituted 8-hydroxyadenine compound containing an amount of from about 100 mg to about 1200 mg, from about 600 mg to about 1000 mg, or from about 700 to about 900 mg per day orally for the desired treatment duration.

In some embodiments, the instant invention provides a method for treating a gastrointestinal inflammatory disorder in an individual by administering to an individual in need thereof an effective amounts of two or more Type I interferon activating agents, the method comprising administering: i) a dosage of a TLR7 agonist, a TLR8 agonist, or a TLR9 agonist containing an amount of from about 1 μg to about 1000 mg qd, qod, tiw, bid, or weekly, orally, intramuscularly, subcutaneously, or intravenously; and ii) a dosage of a dendritic cell growth factor containing an amount of from 100 μg to about 250 μg subcutaneously, twice weekly or three times per week, for the desired treatment duration.

In some embodiments, the instant invention provides a method for treating a gastrointestinal inflammatory disorder in an individual by administering to an individual in need thereof an effective amounts of two or more Type I interferon activating agents, the method comprising administering: i) a dosage of a TLR7 agonist, a TLR8 agonist, or a TLR9 agonist containing an amount of from about 1 µg to about 1000 mg qd, qod, tiw, bid, or weekly, orally, intramuscularly, subcutaneously, or intravenously; and ii) a dosage of GM-CSF containing an amount of from about 100 µg to about 250 µg subcutaneously, twice weekly or three times per week, for the desired treatment duration.

In some embodiments, the instant invention provides a method for treating a gastrointestinal inflammatory disorder in an individual by administering to an individual in need thereof an effective amounts of two or more Type I interferon activating agents, the method comprising administering: i) a dosage of a TLR7 agonist, a TLR8 agonist, or a TLR9 agonist containing an amount of from about 1 µg to about 1000 mg qd, qod, tiw, bid, or weekly, orally, intramuscularly, subcutaneously, or intravenously; and ii) a dosage of an IMPDH inhibitor containing an amount of from about 100 mg/m$^2$ to about 1500 mg/m$^2$, e.g., from about 100 mg/m$^2$ to about 500 mg/m$^2$, from about 500 mg/m$^2$ to about 800 mg/m$^2$, from about 800 mg/m$^2$ to about 1000 mg/m$^2$, or from about 1000 mg/m$^2$ to about 1500 mg/m$^2$, for the desired treatment duration.

In some embodiments, the instant invention provides a method for treating a gastrointestinal inflammatory disorder in an individual by administering to an individual in need thereof an effective amounts of two or more Type I interferon activating agents, the method comprising administering: i) a dosage of a TLR7 agonist, a TLR8 agonist, or a TLR9 agonist containing an amount of from about 1 µg to about 1000 mg qd, qod, tiw, bid, or weekly, orally, intramuscularly, subcutaneously, or intravenously; and ii) a dosage of tiazofurin containing an amount of from about 100 mg/m$^2$ to about 1500 mg/m$^2$, e.g., from about 100 mg/m$^2$ to about 500 mg/m$^2$, from about 500 mg/m$^2$ to about 800 mg/m$^2$, from about 800 mg/m$^2$ to about 1000 mg/m$^2$, or from about 1000 mg/m$^2$ to about 1500 mg/m$^2$, for the desired treatment duration. In some embodiments, the method involves administering tiazofurin in an amount of from about 500 mg/m$^2$ to about 1000 mg/m$^2$.

In some embodiments, the instant invention provides a method for treating a gastrointestinal inflammatory disorder in an individual by administering to an individual in need thereof an effective amounts of two or more Type I interferon activating agents, the method comprising administering: i) a dosage of a TLR7 agonist, a TLR8 agonist, or a TLR9 agonist containing an amount of from about 1 µg to about 1000 mg qd, qod, tiw, bid, or weekly, orally, intramuscularly, subcutaneously, or intravenously; and ii) a dosage of mizoribine in an amount of from about 100 mg to about 500 mg per day, e.g., from about 100 mg to about 250 mg, or from about 250 mg to about 500 mg daily, for the desired treatment duration.

Combination Therapy with a Second Therapeutic Agent that Treats a Gastrointestinal Inflammatory Disorder The instant invention provides combination therapy methods for treating a gastrointestinal inflammatory disorder, generally involving administering combined effective amounts of a Type I interferon activating agent and a second therapeutic agent, for a desired treatment duration. The following examples are provided for the purposes of illustration only, and are not meant to be limiting.

In some embodiments, at least one dose of a Type I interferon activating agent is administered concurrently with at least one dose of an additional therapeutic agent. As used herein, the term "concurrently" indicates that the Type I interferon activating agent and the additional therapeutic agent are administered separately and are administered within about 5 seconds to about 15 seconds, within about 15 seconds to about 30 seconds, within about 30 seconds to about 60 seconds, within about 1 minute to about 5 minutes, within about 5 minutes to about 15 minutes, within about 15 minutes to about 30 minutes, within about 30 minutes to about 60 minutes, within about 1 hour to about 2 hours, within about 2 hours to about 6 hours, within about 6 hours to about 12 hours, within about 12 hours to about 24 hours, or within about 24 hours to about 48 hours of one another.

In some embodiments, an additional therapeutic agent is administered during the entire course of Type I interferon activating agent treatment. In other embodiments, an additional therapeutic agent is administered for a period of time that is overlapping with that of Type I interferon activating agent treatment, e.g., the additional therapeutic agent treatment can begin before the Type I interferon activating agent treatment begins and end before the Type I interferon activating agent treatment ends; the additional therapeutic agent treatment can begin after the Type I interferon activating agent treatment begins and end after the Type I interferon activating agent treatment ends; the additional therapeutic agent treatment can begin after the Type I interferon activating agent treatment begins and end before the Type I interferon activating agent treatment ends; or the additional therapeutic agent treatment can begin before the Type I interferon activating agent treatment begins and end after the Type I interferon activating agent treatment ends.

In some embodiments, any of the above-described therapeutic regimens for treating a gastrointestinal inflammatory disorder, the method comprising administering a Type I interferon activating agent, is modified to include administering an effective amount of Plaquenil® (hydroxychloroquine), the method comprising administering a dosage of Plaquenil® containing an amount of 400 mg orally once every 7 days for the desired treatment duration.

In some embodiments, any of the above-described therapeutic regimens for treating a gastrointestinal inflammatory disorder, the method comprising administering a Type I interferon activating agent, is modified to include administering an effective amount of Rheumatrex® (methotrexate), the method comprising administering a dosage of Rheumatrex® containing an amount of from about 2.5 mg to about 10 mg orally once per week for the desired treatment duration In some embodiments, any of the above-described therapeutic regimens for treating a gastrointestinal inflammatory disorder, the method comprising administering a Type I interferon activating agent, is modified to include administering an effective amount of oral prednisone, the method comprising administering a dosage of oral prednisone containing an amount of from about 0.5 mg/kg to about 1.5 mg/kg orally daily for the desired treatment duration.

In some embodiments, any of the above-described therapeutic regimens for treating a gastrointestinal inflammatory disorder, the method comprising administering a Type I interferon activating agent, is modified to include administering an effective amount of Imuran® (azathioprine), the method comprising administering a dosage of Imuran® containing an amount of from about 2 mg/kg to about 3 mg/kg orally daily for the desired treatment duration.

In some embodiments, any of the above-described therapeutic regimens for treating a gastrointestinal inflammatory disorder, the method comprising administering a Type I interferon activating agent, is modified to include administering an effective amount of Cytoxan® (cyclophosphamide), the method comprising administering a dosage of Cytoxan® containing an amount of from about 1 mg/kg to about 3 mg/kg orally daily for the desired treatment duration.

In some embodiments, any of the above-described therapeutic regimens for treating a gastrointestinal inflammatory disorder, the method comprising administering a Type I interferon activating agent, is modified to include administering an effective amount of Sandimmune® (cyclosporine), the method comprising administering a dosage of Sandimmune® containing an amount of from about 2.5 mg/kg to about 19 mg/kg orally daily for the desired treatment duration In some embodiments, any of the above-described therapeutic regimens for treating a gastrointestinal inflammatory disorder, the method comprising administering a Type I interferon activating agent, is modified to include administering an effective amount of Azulfidine® (sulfasalazine), the method comprising administering a dosage of Azulfidine® containing an amount of from about 500 mg to about 2000 mg orally every 6 hours or every 12 hours for the desired treatment duration.

In some embodiments, any of the above-described therapeutic regimens for treating a gastrointestinal inflammatory disorder, the method comprising administering a Type I interferon activating agent, is modified to include administering an effective amount of a TNF antagonist selected from etanercept, infliximab or adalimumab. In some embodiments, any of the above-described therapeutic regimens for treating a gastrointestinal inflammatory disorder, the method comprising administering a Type I interferon activating agent, is modified to include administering an effective amount of a TNF antagonist, where the a dosage of a TNF-α antagonist selected from: (i) ENBREL® etanercept in an amount of about 25 mg of drug subcutaneously biw (ii) REMICADE® infliximab in an amount of about 3 mg/kg to about 10 mg/kg of drug intravenously qw, qow, three times per month, once monthly, once every 6 weeks, or once every 8 weeks and (iii) HUMIRA™ adalimumab in an amount of about 40 mg of drug subcutaneously qw, qow, three times per month, once monthly, once every 6 weeks, or once every 8 weeks, for the desired treatment duration.

Combination Therapy with a Type I Interferon

The instant invention provides combination therapy methods for treating a gastrointestinal inflammatory disorder, generally involving administering combined effective amounts of a Type I interferon activating agent and a Type I interferon, for the desired treatment duration. In some embodiments, the Type I interferon is an IFN-α. In other embodiments, the Type I interferon is an IFN-β. The following examples are provided for the purposes of illustration only, and are not meant to be limiting.

In some embodiments, any of the above-described therapeutic regimens for treating a gastrointestinal inflammatory disorder, the method comprising administering a Type I interferon activating agent, is modified to include administering an effective amount of Betaseron® (IFN-β1b), the method comprising administering a dosage of Betaseron® containing an amount of 0.25 mg administered subcutaneously tiw, qd, or qod for the desired treatment duration In some embodiments, any of the above-described therapeutic regimens for treating a gastrointestinal inflammatory disorder, the method comprising administering a Type I interferon activating agent, is modified to include administering an effective amount of Avonex® (IFN-β1a), the method comprising administering a dosage of Avonex® containing an amount of 30 µg administered intramuscularly once per week for the desired treatment duration In some embodiments, any of the above-described therapeutic regimens for treating a gastrointestinal inflammatory disorder, the method comprising administering a Type I interferon activating agent, is modified to include administering an effective amount of Rebif® (IFN-β1a), the method comprising administering a dosage of Rebif® containing an amount of 44 µg administered subcutaneously tiw for the desired treatment duration In some embodiments, the Type I interferon is an IFN-alpha. Effective dosages of an IFN-alpha range from about 3 µg to about 27 µg, from about 3 MU to about 10 MU, from about 90 µg to about 180 µg, or from about 18 µg to about 90 µg.

Effective dosages of Infergen® consensus IFN-alpha include about 3 µg, about 6 µg, about 9 µg, about 12 µg, about 15 µg, about 18 µg, about 21 µg, about 24 µg, about 27 µg, or about 30 µg, of drug per dose. Effective dosages of IFN-α2a and IFN-α2b can contain an amount of about 3 million Units (MU) to about 30 MU of drug per dose. Effective dosages of PEGASYS® PEGylated IFN-α2a can contain an amount of about 5 µg to about 500 µg, or about 45 µg to about 450 µg, or about 60 µg to about 400 µg, or about 75 µg to about 350 µg, or about 90 µg to about 300 µg, about 105 µg to about 270 µg, or about 120 µg to about 240 µg, or about 135 µg to about 210 µg, or about 150 µg to about 180 µg, or about 135 µg, of drug per dose.

Effective dosages of PEG-INTRON® PEGylated IFN-α2b can contain an amount of about 0.5 µg to about 5.0 µg, or about 0.75 µg to about 3.5 µg, or about 1.0 µg to about 3.0 µg, or about 1.25 µg to about 2.5 µg, or about 1.5 µg to about 2.0 µg, of drug per kg of body weight per dose.

Pharmaceutical Compositions and Kits

The present invention provides pharmaceutical compositions comprising a Type I activating agent; at least one additional (e.g., at least a second) therapeutic agent; and a pharmaceutically acceptable excipient. The additional therapeutic agent is selected from an immunosuppressant, an anti-malarial agent, a TNF-α antagonist, an aminosalicylate, a corticosteroid, an antibiotic, and an NSAID.

The present invention provides further provides pharmaceutical compositions comprising two or more Type I activating agents; and a pharmaceutically acceptable excipient. Thus, e.g., in some embodiments, a subject pharmaceutical composition will comprise, e.g.: 1) a nucleoside analog and a TLR7 agonist; 2) a nucleoside analog and a TLR8 agonist; 3) a nucleoside analog and a TLR9 agonist; 4) an IMPDH inhibitor and a TLR7 agonist; 5) an IMPDH inhibitor and a TLR8 agonist; 6) an IMPDH inhibitor and a TLR9 agonist; 7) a dendritic cell growth factor and a TLR7 agonist; 8) a DC growth factor and a TLR8 agonist; 9) a DC growth factor and a TLR9 agonist; 10) a DC growth factor and a nucleoside analog; or 11) a DC growth factor and an IMPDH inhibitor.

Pharmaceutical compositions comprising a Type I activating agent and at least one additional therapeutic agent, or two or more Type I activating agents, can be provided in a wide variety of formulations. More particularly, the Type I activating agent and the at least one additional therapeutic agent, or the two or more Type I activating agents, can be formulated into pharmaceutical compositions by combination with appropriate, pharmaceutically acceptable carriers or diluents, and may be formulated into preparations in solid, semi-solid (e.g., gel), liquid or gaseous forms, such as tablets, capsules, powders, granules, ointments, solutions, suppositories, injections, inhalants and aerosols.

The Type I activating agent and the at least one additional therapeutic agent, or the two or more Type I activating agents, can be formulated into preparations for injection by dissolving, suspending or emulsifying them in an aqueous or non-aqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

For oral preparations, the Type I activating agent and the at least one additional therapeutic agent, or the two or more Type I activating agents, can be used by themselves or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The Type I activating agent and the at least one additional therapeutic agent, or the two or more Type I activating agents, can be made into suppositories by mixing with a variety of bases such as emulsifying bases or water-soluble bases. The Type I activating agent and the at least one additional therapeutic agent, or the two or more Type I activating agents, can be administered rectally via a suppository or enema. The suppository can include vehicles such as cocoa butter, carbowaxes and polyethylene glycols, which melt at body temperature, yet are solidified at room temperature.

Kits with unit doses of the active agent (e.g., a Type I interferon activating agent, a Type I interferon activating agent and at least one additional therapeutic agent, two or more Type I interferon activating agents), e.g. in oral or injectable doses, are provided. In such kits, in addition to the containers containing the unit doses will be an informational package insert describing the use and attendant benefits of the drugs in treating pathological condition of interest. Preferred compounds and unit doses are those described herein above.

In such kits, in addition to the containers containing the unit doses will be an informational package insert describing the use agent(s) in treating an autoimmune disorder. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, compact disc (CD), etc., on which the information has been recorded. Other suitable media include audiovisual media, e.g., digital versatile disk (DVD), videotape, and the like. Yet another means that may be present is a website address which may be used via the Internet to access the information at a removed site. Any convenient means may be present in the kits.

The present invention provides a medication delivery device pre-loaded with a therapeutically effective amount of a Type I interferon activating agent, e.g., a sufficient amount for one bolus injection of the Type I interferon activating agent, in the treatment of a patient suffering from a gastrointestinal inflammatory disorder. In some embodiments, the medication delivery device is a syringe and needle, pre-loaded with a dosage of a Type I interferon activating agent.

In other embodiments, the medication delivery device is a pen injector (e.g., a medication delivery pen), a number of which are known in the art. Exemplary devices which can be adapted for use in the present methods are any of a variety of pen injectors from Becton Dickinson, e.g., BD™ Pen, BD™ Pen II, BD™ Auto-Injector; a pen injector from Innoject, Inc.; any of the medication delivery pen devices discussed in U.S. Pat. Nos. 5,728,074, 6,096,010, 6,146,361, 6,248,095, 6,277,099, and 6,221,053; and the like. The medication delivery pen can be disposable, or reusable and refillable.

In other embodiments, the medication delivery device is an implantable drug delivery system, preferably a system that is programmable to provide for subcutaneous administration of a Type I interferon activating agent. Exemplary programmable, implantable systems include implantable infusion pumps. Exemplary implantable infusion pumps, or devices useful in connection with such pumps, are described in, for example, U.S. Pat. Nos. 4,350,155; 5,443,450; 5,814,019; 5,976,109; 6,017,328; 6,171,276; 6,241,704; 6,464,687; 6,475,180; and 6,512,954. A further exemplary device that can be adapted for the present invention is the Synchromed infusion pump (Medtronic).

Subjects Suitable for Treatment

Subjects suitable for treatment with a subject monotherapy or combination therapy treatment regimen include individuals suffering from a gastrointestinal inflammatory disorder including, but not limited to, IBD (including Crohn's disease and ulcerative colitis), colitis induced by environmental insults, (e.g., gastrointestinal inflammation (e.g., colitis) caused by or associated with (e.g., as a side effect) a therapeutic regimen, such as administration of chemotherapy, radiation therapy, and the like); colitis in conditions such as chronic granulomatous disease; celiac disease; celiac sprue; colitis caused by food allergies, gastritis, infectious gastritis, and enterocolitis; and pouchitis. In many embodiments, the subject is a human.

Subjects suitable for treatment according to a subject method to treat a gastrointestinal inflammatory disorder include any individual who has been diagnosed as having a gastrointestinal inflammatory disorder. Also suitable for treatment with a subject method are individuals who have been previously treated with a therapeutic agent to treat a gastrointestinal inflammatory disorder, but who are intolerant to treatment with the therapeutic agent. Also suitable for treatment with a subject method are treatment failure patients. For example, individuals suitable for treatment with a subject method include individuals who have been previously treated with a therapeutic agent to treat a gastrointestinal inflammatory disorder but who did not respond to treatment with the therapeutic agent. In addition, individuals suitable for treatment with a subject method include individuals who have been previously treated with a therapeutic agent to treat a gastrointestinal inflammatory disorder, which individuals responded to treatment with the therapeutic agent, but who subsequently relapsed.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); wt, wild-type; kb, kilobase(s); bp, base pair(s); nt, nucleotide(s); i.m., intramuscular(ly); i.p., intraperitoneal(ly); s.c., subcutaneous(ly); and the like.

Example 1

TLR9-Induced Type I Interferon Protects Mice from Experimental Colitis

Methods

Reagents

The following materials were obtained from commercial sources: dextran sulfate sodium (DSS) (mw 30-50 kDa) from ICN (Aurora, Ohio); Hemoccult from Beckman Coulter (Fullerton, Calif.); Rabbit anti-mouse IFN-α and rabbit anti-mouse IFN-β antibodies from PBL Biomedical Laboratories (Piscataway, N.J.); Rabbit IgG from Jackson ImmunoResearch Laboratories (West Grove, Pa.); recombinant murine IFN-β from Chemicon International (Temecula, Calif.); LPS (*Salmonella Minnesota* R595) from Alexis (San Diego, Calif.).

Olisodeoxynucleotides (ODNs)

The ODNs used in this study were LPS-free, HPLC-purified, single-stranded ODNs. Phosphorothioate-stabilized CpG-ODN-1 (class B, 1018) (5'-TGACTGTGAACGTT CGAG ATGA-3'; SEQ ID NO:03), M-ODN (1019) (5'-TGACTGTGAAGGTTCCAGATGA-3'; SEQ ID NO:04) (Roman (1997) *Nat Med* 3:849-8547) and the phosphodiester and phosphothioate-modified CpG-ODN-2 (class A, D19) (5'-Ggtgcatcgatgca GGGGGg-3'; SEQ ID NO:05) (Verthelyi et al. (2001) *J Immunol* 166:2372-237724; Hemmi et al. (2003) *J Immunol* 170:3059-3064) were purchased from TriLink BioTechnologies (San Diego, Calif.). Uppercase and lowercase letters indicate a base with a phosphorothioate and a phosphodiester-modified backbone, respectively.

Mice

The SCID mice are homozygous for a mutation (scid) in the catalytic subunit of DNA-PK (DNA-PKcs) (Beamish et al. (2000) *Nucleic Acids Res* 28:1506-1513). Specific-pathogen-free C57BL/6 (B6), SCID (B6), RAG1$^{-/-}$ (RAG-$^{-/-}$, B6) and Balb/c (B/c), SCID (B/c) and RAG1$^{-/-}$ (B/c) mice age 6-8 weeks were purchased from Jackson Laboratory (Bar Harbor, Me.). 129/SvEv (129) and A.129 (IFN-α/βR$^{-/-}$) mice were purchased from B&K Universal LTD (East Yorkshire, U.K.). Six-8 week old DNA-PKcs$^{-/-}$ mice (B6) (Kurimasa et al. (1999) *Proc Natl Acad Sci USA* 96:1403-1408) were generated and bred at Memorial Sloan Kettering Cancer Center, New York, N.Y. All experimental procedures were conducted in accordance with the UCSD institutional guidelines for animal care and use.

Cell Cultures and Adoptive Transfer

Bone marrow (BM) derived macrophages (BMDM) from WT and IFN-α/βR$^{-/-}$ mice were prepared and allowed to differentiate in macrophage medium supplemented with 30% L-cell medium for 7 days as described (Martin-Orozco et al. (1999) *Int Immunol* 11:1111-1118). BM-derived myeloid dendritic cells (MDC) were cultured from the long bones of WT, RAG$^{-/-}$ SCID and DNA-PKcs$^{-/-}$ mice in the presence of murine GM-CSF (BD-Pharningen, San Diego, Calif.) and characterized as described (Datta et al. (2003) *J. Immunol*

170:4102-4110). BM-derived plasmacytoid DC (PDC) were cultured similarly in the presence of 100 ng/ml of hFlt3 ligand (PeproTech Inc), as described (Verthelyi et al. (2001) supra; and Hemmi et al. (2003) supra).

For adoptive transfer based experiments, BMDM (5×10$^6$ cells per mouse) were transferred i.p. to WT mice just prior to CpG-ODN injection and 2 hrs before DSS administration.

Induction and Evaluation of Experimental Colitis

In a previous study the concentration of DSS was identified that was required to induce a similar severity of colitis in the different mouse strains used in this study (Rachmilewitz et al. (2004) *Gastroenterology* 126:520-528). Mice on the B6 background were given 1.5% (w/v) DSS, mice on the 129/SvEv background were given 4% DSS and mice on the Balb/c background were given 3.5% DSS dissolved in sterile, distilled water ad libitum for 7 days (Rachmilewitz et al. (2004) supra). Groups of mice were treated with 10 μg/mouse of ODNs subcutaneously (s.c.) 2 h before DSS administration. The disease activity index (DAI; the combined score of weight loss and bleeding) was determined as described (Rachmilewitz et al. (2002) *Gastroenterology* 122:1428-144110; and Rachmilewitz et al. (2004) supra). Briefly, scores are defined as follows: Loss in body weight: 0=no loss; 1=5% to 10%; 2=10% to 15%; 3=15% to 20%; 4=over 20%. Hemoccult: 0=no blood; 2=positive; 4=gross blood.

Determination of MPO Activity

The colon tissues were longitudinally opened and a 50 mg portion was homogenized in hexadecyltrimethyl-ammonium bromide (0.5%) in 50 mmol/L phosphate buffer, pH6.0. The homogenate was sonicated for 10 seconds, freeze-thawed 3 times, and centrifuged for 15 minutes. An aliquot of the supernatant was taken for determination of enzyme activity as described (Rachmilewitz et al. (2002) supra; and Rachmilewitz et al. (2004) supra).

Histological Scoring

After 7 days of DSS administration, mice were killed and the entire colon was excised, longitudinally opened, rolled onto a wooden stick, fixed with Bouin's Solution (Sigma, St. Louis, Mo.), and embedded in paraffin. Tissue sections (5 μm) were prepared, deparaffinized, and stained with hematoxylin and eosin. Histological scoring was performed in a blinded fashion. Colonic epithelial damage was scored as follows: 0=normal; 1=hyper-proliferation, irregular crypts, and goblet cell loss; 2=mild to moderate crypt loss (10-50%); 3=severe crypt loss (50-90%); 4=complete crypt loss, surface epithelium intact; 5=small to medium sized ulcer (<10 crypt widths); 6=large ulcer (≧10 crypt widths). Infiltration with inflammatory cells was scored separately for mucosa (0=normal, 1=mild, 2=modest, 3=severe), submucosa (0=normal, 1=mild to modest, 2=severe), and muscle/serosa (0=normal, 1=moderate to severe). Scores for epithelial damage and inflammatory cell infiltration were added, resulting in a total scoring range of 0-12.

Determination of Cytokine Levels

ELISA kits were used to determine the levels of IFN-γ, IL-6, IL-12p40, IL-10 (BD Pharmingen, San Diego, Calif.), and RANTES (R&D Biosystems, Minneapolis, Minn.). To measure type-1 IFN levels an ELISA kit (PBL) was compared to a bioassay that is based on an antiviral protection assay (Hoebe et al. (2003) *Nature* 424:743-748). As the bioassay was much more sensitive than the currently available mouse IFN-α ELISA, it was used in the various studies described here to determine type-1 IFN levels. Recombinant mouse IFN-β (Chemicon International, Temecula, Calif.) was used in the bioassay as a standard.

Signaling Assays

EMSA—Nuclear extracts were prepared from BMDCs that had been stimulated with CpG-ODN or LPS. Activation of nuclear factor-κB (NF-κB) was measured by electrophoretic mobility shift assay (EMSA) as described (Lee et al. (2000) *J Leukoc Biol* 68:909-915).

Activation of IRF molecules—Levels of different IRFs in the nuclei were measured before and after stimulation with TLR9 and TLR4 agonists using nuclear extracts of BMDCs. IRFs were detected by western blotting (Au et al. (2001) *J Biol Chem* 276:41629-4163739) using specific anti-IRF-1, -IRF-3, -IRF-7, and anti-IRF-8 antibodies (Santa Cruz Biotechnology, Santa Cruz, Calif.). IRF-7 ubiquitination status was detected by immunoprecipitating with anti-ubiquitin antibodies (Santa Cruz) followed by immunoblotting with anti-IRF-7 antibodies (Santa Cruz).

Activation of ERK and STAT1—Activation of ERK and STAT1 were assayed with antibodies specific to phosphorylated ERK or STAT-1 (Hsu et al. (2004) *Nature* 428:341-34540) (Cell Signaling, Beverly, Mass.). Beta actin (Sigma, St. Louis, Mo.) levels were used for normalization of protein loading.

DNA-PKcs activity—Kinase activity of DNA-PKcs induced by CpG-ODN or LPS was measured by an in vitro kinase assay using recombinant p53 as a substrate (Tsujimura et al. (2003) *J Immunol* 170:1131-11352; Woo et al. (1998) *Nature* 394:700-704). DNA-PKcs from BMDCs was immunoprecipitated using anti-DNA-PKcs antibodies (NeoMarkers, Fremont, Calif.) before and after CpG-ODN or LPS stimulation and immune complexes were incubated with GST-p53 and $^{32}$P-γ-ATP for 30 min. The reaction samples were then electrophoresed (sodium dodecyl sulfate-polyacrylamide gel electrophoresis; SDS-PAGE) and analyzed by autoradiography.

Statistical Analysis

Data are expressed as mean±standard error. Statistical analysis for significant differences was performed according to the Student t test for unpaired data. $P<0.05$ was considered significant.

Results

TLR9 agonist attenuates DSS-induced colitis in RAG$^{-/-}$ but not SCID mice.

Previous studies demonstrated similar histopathological features in the colon of wild-type (WT) and SCID mice following the oral administration of dextran sulfate sodium (DSS) (Dieleman et al. (1994) *Gastroenterology* 107:1643-1652), a finding that was confirmed in this work (Table 3). RAG$^{-/-}$ mice, which resemble SCID mice phenotypically, also showed a similar degree of colon inflammation upon DSS feeding (Table 3). As expected, administration of CpG-ODNs to WT mice attenuated DSS-induced colitis, as shown by improved disease activity and histological scores and reduction of colonic MPO activity (Rachmilewitz et al. (2002) supra; and Rachmilewitz et al. (2004) supra). This protection was also observed in RAG$^{-/-}$ mice on a C57BL/6 (B6) background, but interestingly not in SCID mice (B6) (Table 3). Histologically, the extensive ulcerations with mucosal inflammation induced by DSS were markedly attenuated in the colon of WT and RAG$^{-/-}$ but not in the colon of SCID mice following the administration of CpG-ODNs. Similar data were obtained in WT, RAG$^{-/-}$ and SCID mice on a Balb/c background.

Table 3 depicts the effect of administration of TLR9 agonists on DSS-induced colitis in WT, SCID and RAG$^{-/-}$ mice. Mice (B6 background) were treated once subcutaneously (s.c.) with CpG-ODN-1 (1018), CpG-ODN-2 (D19), or control (M)-ODN (1019), 10 μg/animal, 2 h prior to induction of colitis by DSS (1.5%). Colitis was evaluated 7 days later. No mortality was observed in any of the experimental groups. Results are mean±SEM of at least 8 mice/group. $^A$ denotes significant difference from untreated group ($P<0.05$). DAI-disease activity index, MPO-myeloperoxidase, HS-histological score.

TABLE 3

| Mouse | Intervention | DAI | MPO (U/g) | HS |
|---|---|---|---|---|
| C57BL/6 (WT) | DSS | 5.1 ± 0.3 | 1.9 ± 0.2 | 10.3 ± 0.2 |
| WT | DSS + CpG-ODN-1 | 0.3 ± 0.2$^A$ | 0.5 ± 0.1$^A$ | 4.4 ± 0.4$^A$ |
| WT | DSS + M-ODN | 6.6 ± 1.1 | 2.0 ± 0.3 | 10.3 ± 0.5 |
| SCID | DSS | 5.7 ± 0.5 | 1.7 ± 0.4 | 9.6 ± 0.7 |
| SCID | DSS + CpG-ODN-1 | 5.2 ± 0.5 | 1.5 ± 0.4 | 8.2 ± 0.5 |
| SCID | DSS + CpG-ODN-2 | 6.5 ± 0.6 | 1.3 ± 0.1 | 9.8 ± 0.3 |
| RAG1$^{-/-}$ | DSS | 7.1 ± 0.2 | 2.1 ± 0.1 | 8.6 ± 0.6 |
| RAG1$^{-/-}$ | DSS + CpG-ODN-1 | 0.8 ± 0.2$^A$ | 0.5 ± 0.1$^A$ | 3.9 ± 0.4$^A$ |
| RAG1$^{-/-}$ | DSS + CpG-ODN-2 | 1.9 ± 0.7$^A$ | 0.9 ± 0.2$^A$ | 5.0 ± 0.8$^A$ |

Soluble factors from CpG-ODN-stimulated RAG$^{-/-}$ splenocytes inhibit DSS-induced colitis.

Since the activation of TLR9 by its ligands has a broad range of activities on the mammalian innate immune system, the anti-inflammatory effect induced by its activation in WT and RAG$^{-/-}$ mice could be mediated by soluble factors secreted from effector cells or by cognate interactions between effector cells. To explore these possibilities, conditioned medium was generated from CpG-ODN-stimulated RAG$^{-/-}$ splenocytes and evaluated its anti-inflammatory activity on DSS-induced colitis in SCID mice, which were unresponsive to the CpG-ODN effects. The administration of this conditioned medium attenuated the severity of DSS-induced colitis in SCID mice, whereas conditioned medium from CpG-ODN-stimulated SCID splenocytes, as well as control medium, had no effect on the outcome of colitis in these mice. These data suggest the presence of soluble and inducible factors with anti-inflammatory properties in conditioned medium from CpG-ODN-stimulated RAG$^{-/-}$ splenocytes.

TLR9 triggers divergent type-1 IFN responses in SCID and RAG$^{-/-}$ mice.

The data above indicate that the transfer of conditioned medium from CpG-ODN-stimulated RAG$^{-/-}$ splenocytes, but not SCID splenocytes, to DSS-treated SCID mice is sufficient to inhibit colitis. To identify a putative inhibitor of colitis in the conditioned medium, the levels of different soluble mediators known to be induced by CpG-ODN-ODN in splenocyte culture were measured (Krieg (2002) *Annu Rev Immunol* 20:709-760 6). As presented in FIG. 1A, the levels of IL-12 (p40), IL-6, and IL-10 were similar in the supernatants of CpG-ODN-stimulated SCID and RAG$^{-/-}$ splenocytes. In contrast, conditioned medium from CpG-ODN-treated SCID splenocytes had lower levels of IFN-γ (2.5 fold), RANTES (2.3 fold) and IFN-α/β (6.3 fold). To further validate these differences in vivo, CpG-ODN was injected i.v. into the tail veins of SCID and RAG$^{-/-}$ mice and assayed the levels of these cytokines in their serum (FIG. 1B). Although SCID and RAG$^{-/-}$ mice produced similar amounts of IL-6 and IL-12, they differed in their levels of IFN-γ (2 fold) and IFN-α/β (10 fold). The levels of IFN-α/β were analyzed by bioassay. It was determined in preliminary studies that this assay was by far more sensitive than a commercially available ELISA. Moreover, the reduced IFN-α/β production in SCID mice was not due to lower numbers of DC (CD 11c$^+$) or plasmacytoid DC (CD11c$^{low}$/B220$^+$/GR1$^+$), which are the major source of IFN-α/β in the mouse, since FACS analysis demonstrated that their numbers were similar in the spleens of SCID and RAG$^{-/-}$ mice.

Figure 1A:
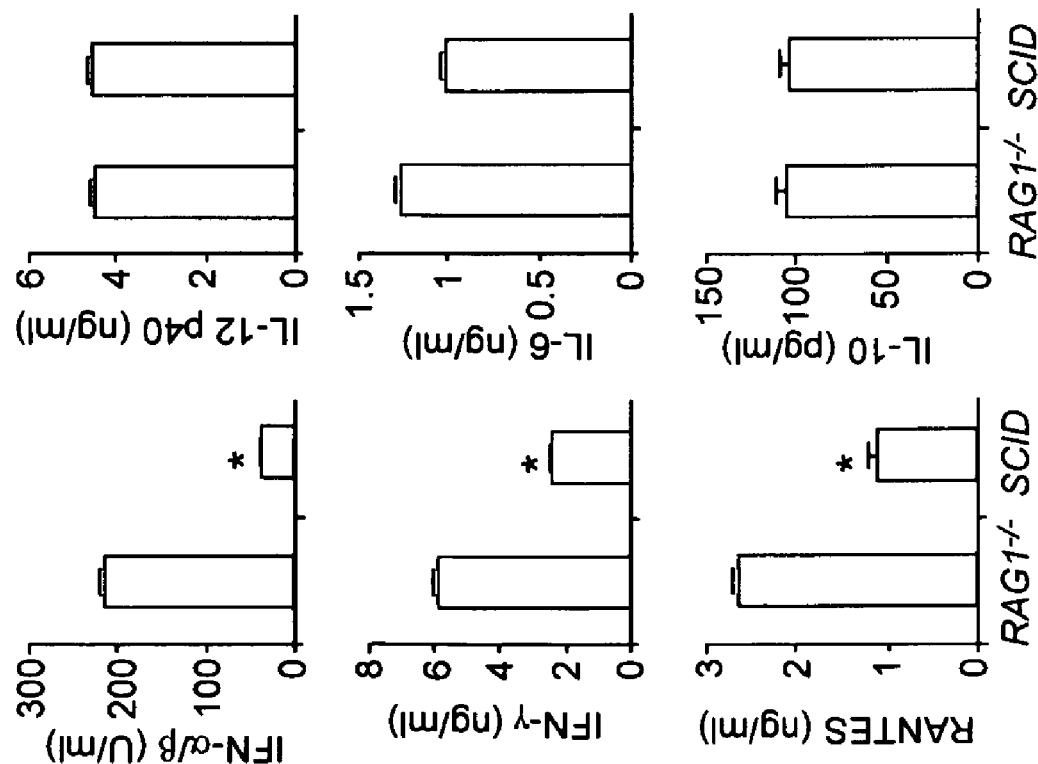
Figure 4:
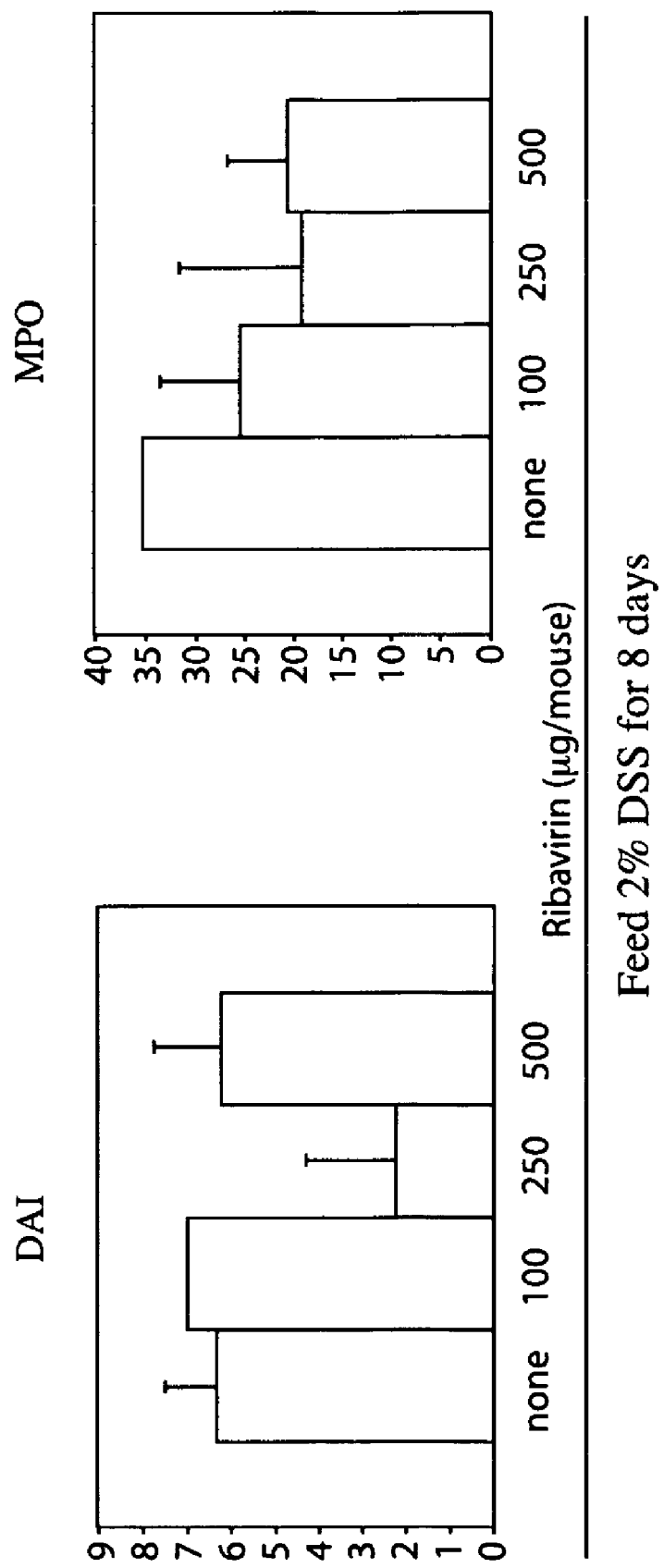
FIG. 4 depicts data showing the effect of an IMPDH inhibitor on DSS-induced colitis.

FIGS. 1A and 1B: Cytokine production after CpG-ODN stimulation. (FIG. 1A) 10$^6$/ml splenocytes from RAG1$^{-/-}$ and SCID mice were stimulated with CpG-ODN-1 (10 μg/ml) and cytokine levels in the supernatants were measured 48 hrs later. (FIG. 1B) Serum levels of cytokines 2 hrs after i.v. injection of 50 μg of CpG-ODN-1. Results represent one of two experiments (n=4 per group per experiment). Similar results were obtained for CpG-ODN-2. The cytokine levels in naïve mice were below detectible levels. *P<0.05, SCID vs. RAG1$^{-/-}$.

IFN-α/β Protects from DSS-Induced Colitis

As IFN-α/β was induced by CpG-ODN in RAG$^{-/-}$ but not in SCID mice, it was hypothesized that IFN-α/β might play a role in suppressing colitis inflicted by DSS administration. As presented in Table 4, injection of neutralizing anti-IFN-α/β antibodies was sufficient to abolish the beneficial effect induced by CpG-ODN on colitis whereas the injection of control IgG Abs had no effect.

Table 4 depicts data showing that TLR9-induced type-1 IFN protects mice from experimental colitis. RAG1$^{-/-}$ mice (B6) were injected i.v. with 25 μg/mouse of rabbit anti-mIFN-α/β antibodies (8000 IFN-α/β neutralizing units) or with control rabbit IgG (25 μg/mouse) before treatment with CpG-ODN-1 (10 μg/animal). Colitis was induced by 1.5% DSS in drinking water and was evaluated 7 days later. No mortality was observed in any of the experimental groups (n=6 mice per group). Data are mean±SEM and represent one of two experiments with similar results. $^A$ denotes significant difference from untreated group (P<0.05). $^B$ denotes significant difference from anti-IFNα/β Abs treated group (P<0.05). DAI-disease activity index, MPO-myeloperoxidase, HS-histological score.

TABLE 4

| Mouse | Intervention | DAI | MPO (U/g) | HS |
| --- | --- | --- | --- | --- |
| RAG1$^{-/-}$ | None | 7.4 ± 0.2 | 1.9 ± 0.4 | 9.1 ± 0.3 |
| RAG1$^{-/-}$ | CpG-ODN-1 | 0.8 ± 0.2$^A$ | 0.5 ± 0.1$^A$ | 4.6 ± 0.5$^A$ |
| RAG1$^{-/-}$ | CpG-ODN-1 + anti-IFN-α/β Abs | 6.8 ± 0.7 | 1.7 ± 0.2 | 9.0 ± 0.3 |
| RAG1$^{-/-}$ | CpG-ODN-1 + control IgG | 0.8 ± 0.4$^B$ | 0.7 ± 0.2$^B$ | 3.7 ± 0.6$^B$ |

To further evaluate the protective role of CpG-ODN-induced IFN-α/β against DSS-induced colitis, mice lacking the common receptor for IFN-α/β, i.e., IFN-α/βR$^{-/-}$, were treated with CpG-ODN. IFN-α/βR$^{-/-}$ mice were extremely sensitive to DSS-induced colitis. The administration of 4% DSS to IFN-α/βR$^{-/-}$ mice resulted in 50% mortality whereas no mortality was observed in the WT control (P<0.05). The administration of 2.5% DSS colitis to IFN-α/βR$^{-/-}$ mice resulted in the same severity of colitis as was induced by 4% DSS in WT mice whereas the administration of 2.5% DSS to WT mice did not induce apparent colitis (P>0.05 for DAI and MPO). Interestingly, CpG-ODN administration to the mutant mice, which received 4% DSS, increased their mortality from 50% to 75% (P=NS) whereas CpG-ODN administration to WT animals (4% DSS) inhibited the severity of the various parameters of colonic inflammation (Table 5). To test whether IFN-α/β directly prevents the damage inflicted by DSS in the colon, recombinant mouse IFNβ (mIFN-β) was injected intraperitoneally (i.p.) on days 0, 2, 4, and 6 after DSS administration.

Table 5 depicts data showing that IFN-α/βR$^{-/-}$ mice are hypersensitive to DSS administration. WT and mutant mice were treated once s.c. with CpG-ODN-1 (10 μg/animal) 2 h prior to induction of colitis by 4% DSS. Colitis was evaluated 7 days later. n=8 animals per group for the WT and n=16 per group for the mutant mice. No mortality was observed in CpG-ODN-treated or untreated WT mice. In contrast, CpG-ODN-treated mutant mice displayed mortality of 75% whereas the CpG-ODN-untreated mutant mice displayed mortality of 50%. The analysis above was performed on surviving mice. Data are mean±SEM and represent one out of two experiments with similar results. $^A$ denotes significant difference from untreated group (P<0.05). DAI-disease activity index, MPO-myeloperoxidase, HS-histological score.

TABLE 5

| Mouse | Intervention | DAI | MPO (U/g) | HS |
| --- | --- | --- | --- | --- |
| WT | DSS | 5.4 ± 0.5 | 2.0 ± 0.2 | 8.8 ± 1.1 |
| WT | DSS + CpG-ODN-1 | 0.1 ± 0.1$^A$ | 0.2 ± 0.01$^A$ | 1.7 ± 0.4$^A$ |
| IFN-α/βR$^{-/-}$ | DSS | 7.2 ± 0.3 | 2.0 ± 0.1 | 10.4 ± 0.4 |
| IFN-α/βR$^{-/-}$ | DSS + CpG-ODN-1 | 7.8 ± 0.2 | 1.7 ± 0.1 | 10.7 ± 0.4 |

As shown in Table 6, injection of recombinant mIFN-β decreased the disease activity and the histological scores in DSS-treated mice. Taken together, these data indicate that the anti-inflammatory effects of CpG-ODN in this system were largely mediated by type-1 IFN.

Table 6 depicts data showing that Type-1 IFN protects from DSS-induced colitis. SCID mice (B6) were treated i.p. with 1000 U of recombinant mIFN-β 2 rs h prior to and on days 2, 4, and 6 after the induction of colitis with 1.5% DSS. Colitis was evaluated 7 days later. No mortality was observed in any of the experimental groups. n=8 mice per group. Data are mean±SEM and represent one out of two experiments with similar results. $^A$ denotes significant difference from untreated group (P<0.05). DAI-disease activity index, MPO-myeloperoxidase, HS-histological score.

TABLE 6

| Mouse | Intervention | DAI | MPO (U/g) | HS |
| --- | --- | --- | --- | --- |
| SCID | DSS | 7.7 ± 0.3 | 1.5 ± 0.5 | 11.1 ± 0.2 |
| SCID | DSS + IFN-β | 4.6 ± 0.9$^A$ | 1.2 ± 0.1 | 6.8 ± 1.2$^A$ |

Finally, to explore whether the protective role of IFN-α/β is mediated via the inhibition of inflammatory cells, such as macrophages, bone marrow-derived macrophages (BMDM) were adoptively transferred from WT or IFN-α/βR$^{-/-}$ mice i.p. to WT mice prior to their challenge with DSS. Administration of CpG-ODN protected WT mice transferred with WT-BMDM from experimental colitis but did not protect WT mice adoptively transferred with IFN-α/βR$^{-/-}$-BMDM (Table 7). In another set of experiments, BMDM from WT and from IFN-α/βR$^{-/-}$ mice were labeled with CFSE prior to their transfer to WT mice. The number of CFSE labeled BMDM in the colon of DSS-challenged, CpG-ODN-treated WT mice was similar, suggesting that BMDM from WT and IFN-α/βR$^{-/-}$ mice trafficked equally to the inflamed colon. These results indicate that IFN-α/β inhibits, at least in part, the severity of DSS-induced colitis by suppressing macrophage pro-inflammatory activity.

Table 7 depicts data showing that CpG-ODN affect the severity of DSS-induced colitis by BMDM. CpG-ODN administration does not affect the severity of DSS-induced colitis in wt mice adoptively transferred with BMDM from IFN-α/βR$^{-/-}$ mice. WT mice (129) were adoptively transferred i.p. with BMDM (5×10$^6$/mouse) from WT or from IFN-α/βR$^{-/-}$ mice and treated once s.c. with CpG-ODN-1 (10 μg/animal) 2 h prior to induction of colitis by DSS (4%). Colitis was evaluated after the 7th day of DSS administration. n=8 mice per group. No mortality was observed in any of the experimental groups. Data are mean±SEM and represent one out of two experiments with similar results. $^A$ denotes P<0.05 compared to the untreated group. DAI-disease activity index, MPO-myeloperoxidase, HS-histological score.

TABLE 7

| Mouse | BMDM | Intervention | DAI | MPO (U/g) | HS |
|---|---|---|---|---|---|
| WT | WT | DSS | 5.2 ± 0.6 | 2.4 ± 0.5 | 9.8 ± 0.2 |
| WT | WT | DSS + CpG-ODN-1 | 0.7 ± 0.4$^A$ | 0.8 ± 0.2$^A$ | 3.0 ± 0.4$^A$ |
| WT | IFN-α/βR$^{-/-}$ | DSS | 4.5 ± 0.8 | 2.2 ± 0.4 | 9.6 ± 0.3 |
| WT | IFN-α/βR$^{-/-}$ | DSS + CpG-ODN-1 | 3.3 ± 1.3 | 1.9 ± 0.5 | 8.5 ± 0.5 |
| WT | | | | | |

Regulation of IFN-α/β Production Via TLR9 Depends on DNA-PK

As outlined above, IFN-α/β is differentially induced in SCID and RAGα/βR$^{-/-}$ mice upon TLR9 signaling. Previous studies have demonstrated that NF-κB, MAPK, and members of the interferon regulatory factor family (IRFs) control IFN-α/β transcription (Taniguchi et al. (2001) *Annu Rev Immunol* 19:623-65513). Since deletion of the kinase domain of DNA-PKcs is responsible for the SCID phenotype, the role of DNA-PK in TLR9-mediated type-I IFN induction was investigated. To do so, bone marrow-derived myeloid dendritic cells (MDC) from RAG$^{-/-}$ mice were incubated with various concentrations of NU7026, a DNA-PK inhibitor (Calbiochem, San Diego, Calif.), with or without CpG-ODN. This compound selectively inhibited IFN-α/β without affecting IL-12 (p40) production by CpG-ODN, suggesting a selective involvement of DNA-PK in the induction of type-1 IFN by TLR9 triggering. Similarly, BM-MDC from RAG$^{-/-}$ but not from SCID mice produced high levels of IFN-α/β upon CpG-ODN stimulation (FIG. 2A). Comparable results were obtained for BM plasmacytoid DC (PDC). This divergent induction of IFN-α/β was paralleled by nuclear translocation of IRF-1 and IRF-8 in RAG$^{-/-}$ but not in SCID mice (FIG. 2B). In contrast, the activation of NF-κB, MAPK, IRF-3 and IRF-7 were similar in these cells (FIG. 2B), indicating a specific signaling blockade downstream to TLR9 in SCID but not in RAG$^{-/-}$ BM-MDC. Furthermore, DNA-PK was rapidly activated, as assessed by the phosphorylation of GST-p53, by CpG-ODN in MDC from RAG$^{-/-}$ but not from SCID mice (FIG. 2B). In contrast to the activation by TLR9 agonist, the stimulation of SCID- and RAG$^{-/-}$ BM-MDC with the TLR4 agonist, LPS, resulted in similar production of IFN-α/β (FIG. 2C) and similar activation of NF-κB, MAPK and IRF molecules (FIG. 2D).

FIGS. 2A-D: DNA-PK mediates TLR9-induced type I IFN production via IRF-1 and IRF-8. (FIG. 2A) BM-MDC (10$^6$/ml) from RAG1$^{-/-}$ and SCID mice (B6) were stimulated with CpG-ODN-1 (10 μg/ml). Cytokine levels in the supernatants were measured 24 hrs later. *P<0.05, SCID vs. RAG1$^{-/-}$. (FIG. 2B) BM-MDC were treated with CpG-ODN-1 (10 μg/ml) and nuclear extracts were prepared. NF-κB was detected by EMSA, activation of DNA-PKcs by in vitro kinase assay, and activation of IRFs, pSTAT-1 and pERK by western blotting. Results represent one of three experiments. (FIG. 2C) 10$^6$/ml BM-MDC from RAG1$^{-/-}$ and SCID mice (B6) were stimulated with 50 ng/ml of LPS. After 24 h the cytokine levels in the supernatants were measured. (FIG. 2D) BM-MDC were treated with LPS (50 ng/ml) and nuclear extracts were prepared. Signaling assays were performed as described for (FIG. 2B). Results represent one of three experiments.

Defects in activation of IRF-1 and IRF-8 in BM-PDC from DNA-PKcs$^{-/-}$ mice (FIGS. 3A), as well as very low levels of IFN-α/β upon CpG-ODN stimulation in BM-PDC and BM-MDC from DNA-PKcs$^{-/-}$ mice, were observed (FIGS. 3B and 3C). Thus, the data obtained with the DNA-PK inhibitor, with the SCID and the DNA-Pkc$^{-/-}$ MDC and PDC indicate the necessary involvement of DNA-PK in the induction of IFN-α/β via TLR9 signaling.

FIGS. 3A-C: TLR9-activated DNA-PK mediates activation of IRFs and type-I IFN via MyD88. (FIG. 3A) BM-PDC were treated with CpG-ODN-1 (10 μg/ml) and nuclear extracts were prepared. NF-κB was detected by EMSA, activation of IRFs, pSTAT-1 and pERK by western blotting. Results represent one of two experiments. (FIG. 3B) BM-PDC (10$^6$/ml) from RAG1$^{-/-}$ and SCID mice (B6) were stimulated with CpG-ODN-1 (10 μg/ml). Cytokine levels in the supernatants were measured 24 hrs later. (FIG. 3C) BM-MDC (10$^6$/ml) from RAG1$^{-/-}$ and SCID mice (B6) were stimulated with CpG-ODN-1 (10 μg/ml). Cytokine levels in the supernatants were measured 24 hrs later.

Involvement of DNA-PK

TLR9 signaling depends on MyD88 (Hemmi et al. (2000) *Nature* 408:740-7455); and TLR9-mediated IFN-α/β production depends on DNA-PK (FIGS. 2A-D and FIGS. 3A-C). Recently, it was suggested that the induction of IFN-α/β via TLR9 requires the formation of a complex consisting of MyD88, TRAF and IRF-7 as well as TRAF6-dependent ubiquitination of IRF-7 (Honda et al. (2004) *Proc Natl Acad Sci USA* 101:15416-1542114; Kawai et al. (2004) *Nat Immunol* 5:1061-106). As shown in FIG. 3C, ubiquitination of IRF-7 was detected in RAG$^{-/-}$ but not in SCID BM-MDC. These data further indicate the involvement of DNA-PK in the translocation of IRF-1/IRF-8 and in the ubiquitination of IRF-7 upon TLR9 signaling.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for treating a gastrointestinal inflammatory disorder in an individual, the method comprising administering to a subject suffering from a gastrointestinal inflammatory disorder an effective amount of Type I interferon activating agent that increases the level of a Type I interferon and/or activates a Type I interferon signaling pathway, wherein said Type I interferon activating agent is a chimeric toll-like receptor (TLR) ligand comprising a TLR9 agonist moiety and a TLR8 agonist moiety, a chimeric TLR ligand comprising a TLR9 agonist moiety and a TLR7 agonist moiety, or a chimeric TLR ligand comprising a TLR7 agonist moiety and a TLR8 agonist moiety.

2. The method of claim 1, wherein the TLR7 agonist moiety selected from an imidazoquinoline compound, a C8-substituted guanine ribonucleotides, and an N7, C8-substituted guanine ribonucleotide.

3. The method of claim 2, wherein the TLR7 agonist moiety is a selective TLR7 agonist.

4. The method of claim 1, wherein the TLR8 agonist moiety is an amide substituted imidazoquinoline amine.

5. The method of claim 4, wherein the TLR8 agonist moiety is a selective TLR8 agonist.

6. The method of claim 1, further comprising administering at least one additional therapeutic agent that treats a gastrointestinal inflammatory disorder.

7. The method of claim 6, wherein the at least one additional therapeutic agent is selected from an immunosuppressant, an anti-malarial agent, a TNF-α antagonist, an aminosalicylate, a corticosteroid, and a non-steroidal anti-inflammatory drug.

8. The method of claim 7, wherein the at least one additional therapeutic agent is an immunosuppressant selected from azothioprine, tacrolimus, cyclophosphamide, and cyclosporine.

9. The method of claim 7, wherein the at least one additional therapeutic agent is hydroxychloroquine.

10. The method of claim 7, wherein the at least one additional therapeutic agent is a TNF-α antagonist selected from etanercept, infliximab, and adalimumab.

11. The method of claim 7, wherein the at least one additional therapeutic agent is selected from 5-aminosalicylate, sulfasalazine, olsalazine and mesalamine.

12. The method of claim 7, wherein the at least one additional therapeutic agent is a corticosteroid selected from prednisolone, dexamethasone, hydrocortisone, and prednisone.

13. The method of claim 1, wherein said administering is by an oral route.

14. The method of claim 1, wherein said administering is by a subcutaneous route.

15. The method of claim 1, wherein said administering is by a rectal route.

16. The method of claim 1, wherein the gastrointestinal inflammatory disorder is chronic gastrointestinal inflammation.

17. The method of claim 1, wherein the chronic gastrointestinal inflammation is caused by inflammatory bowel disease.

18. The method of claim 1, wherein the inflammatory bowel disease is ulcerative colitis.

19. The method of claim 1, wherein the inflammatory bowel disease is Crohn's disease.

20. The method of claim 1, wherein the gastrointestinal inflammatory disorder is acute gastrointestinal inflammation.

21. The method of claim 1, wherein the gastrointestinal inflammatory disorder is pouchitis.

22. The method of claim 1, further comprising administering an effective amount of an IFN-α.

23. The method of claim 1, further comprising administering an effective amount of an IFN-β.

24. The method of claim 1, wherein the individual is a human.

* * * * *

SEQUENCE LISTING

<160> NUMBER OF SEQ ID NOS: 5

<210> SEQ ID NO 1
<211> LENGTH: 10
<212> TYPE: DNA
<213> ORGANISM: Artificial Sequence
<220> FEATURE:
<223> OTHER INFORMATION: synthetic DNA
<220> FEATURE:
<221> NAME/KEY: misc_feature
<222> LOCATION: 1, 2, 6, 7
<223> OTHER INFORMATION: n = A,T,C or G

<400> SEQUENCE: 1 nntcgnntcg                                                              10

<210> SEQ ID NO 2
<211> LENGTH: 24
<212> TYPE: DNA
<213> ORGANISM: Artificial Sequence
<220> FEATURE:
<223> OTHER INFORMATION: synthetic DNA

<400> SEQUENCE: 2
tcgtcgtttt gtcgttttgt cgtt                                              24

<210> SEQ ID NO 3
<211> LENGTH: 22
<212> TYPE: DNA
<213> ORGANISM: Artificial Sequence
<220> FEATURE:
<223> OTHER INFORMATION: synthetic DNA

<400> SEQUENCE: 3
tgactgtgaa cgttcgagat ga                                                22

<210> SEQ ID NO 4
<211> LENGTH: 22
<212> TYPE: DNA
<213> ORGANISM: Artificial Sequence
<220> FEATURE:
<223> OTHER INFORMATION: synthetic DNA

<400> SEQUENCE: 4
tgactgtgaa ggttccagat ga                                                22

<210> SEQ ID NO 5
<211> LENGTH: 20
<212> TYPE: DNA
<213> ORGANISM: Artificial Sequence
<220> FEATURE:
<223> OTHER INFORMATION: synthetic DNA

<400> SEQUENCE: 5
ggtgcatcga tgcagggggg                                                   20